United States Patent
Strabala et al.

(10) Patent No.: US 6,359,198 B1
(45) Date of Patent: Mar. 19, 2002

(54) COMPOSITIONS ISOLATED FROM PLANT CELLS AND THEIR USE IN THE MODIFICATION

(75) Inventors: Timothy J. Strabala, Auckland; Nicolaas J. Nieuwenhuizen, Mt. Eden, both of (NZ)

(73) Assignee: Genesis Research & Development Corporation Ltd. (NZ)

( * ) Notice: Subject to any disclaimer, the term of this patent is extended or adjusted under 35 U.S.C. 154(b) by 0 days.

(21) Appl. No.: 09/228,986

(22) Filed: Jan. 12, 1999

(51) Int. Cl.$^7$ ............................. A01H 5/00; C12N 15/82
(52) U.S. Cl. ....................... 800/298; 800/278; 435/415; 536/23.6
(58) Field of Search ................................ 536/23.1, 23.2, 536/23.6, 24.1; 435/468, 410, 419; 800/278, 283, 295, 298, 319

(56) References Cited

U.S. PATENT DOCUMENTS

| | | | |
|---|---|---|---|
| 5,484,905 A | 1/1996 | Nasrallah et al. | 536/23.6 |
| 5,650,553 A | 7/1997 | Ecker et al. | 800/205 |
| 5,689,055 A | * 11/1997 | Meyerowitz et al. | 800/205 |
| 5,766,878 A | 6/1998 | Wallis | 435/69.1 |

OTHER PUBLICATIONS

Smith et al. Nature 1988. vol. 334: 724–726.*
Martin et al. Science, 1993. vol. 262: 1432–1436.*
Bork, "Go hunting in sequence databases but watch out for the traps", 1996, TIG vol. 12, No. 10 pp. 425–427.*
Smith et al, The challenges of genome sequence annotation or "The devil is in the details", 1997, Nature Biotechnology vol. 15 pp. 1222–1223.*
Brenner, "Errors in genome annotation", 1999, TIG vol. 15 No. 4 pp. 132–133.*
Chang et al, "Arabidopsis Ethylene–Response Gene ETR1: Similarity of Product to Two–Component Regulators", 1993 Science vol. 262 pp. 539–544.*
Doerks, "Protein annotation" detective work for function prediction, 1998, TIG vol. 14 No. 6 pp. 248–250.*
Bugos, Robert C., et al., "cDNA Cloning, Sequence Analysis and Seasonal Expression of Lignin–Bispecific Caffeic Acid/ 5–Hydroxyferulic Acid O–Methyltransferase of Aspen," *Plant Molecular Biology*, vol. 17, pp. 1203–1215 (1991).

Dwivedi, Upendra N., et al., "Modification of Lignin Biosynthesis in Transgenic Nicotiana Through Expression of an Antisense O–Methyltransferase Gene from Populus," *Plant Molecular Biology*, vol. 26, pp. 61–71 (1994).

Sakai, Hajime et al., "ETR2 is an ETR1–like gene involved in ethylene signaling in Arbidopsis," *Proc. Natl. Acad. Sci.*, vol. 95, pp. 5812–5817 (May, 1998).

Brandstatter, Ingrid et al., "Two Genes with Similarity to Bacterial Response Regulators Are Rapidly and Specifically Induced by Cytokinin in Arabidopsis," *The Plant Cell*, vol. 10, pp. 1009–1019 (Jun. 1998).

Kakimoto, Tatsuo, "CKI1, a Histidine Kinase Homolog Implicated in Cytokinin Signal Transduction," *Science*, vol. 274, pp. 982–985 (Nov. 8, 1996).

Song, Wen–Yuen, et al., "A receptor Kinase–Like Protein Encoded by the Rice Disease Resistance Gene, Xa21," *Science*, vol. 270, pp. 1804–1806 (Dec. 15, 1995).

He, Zheng–Hui, et al., "Requirement for the induced expression of a cell wall associated receptor kinase for survival during the pathogen response," *The Plant Journal*, vol. 14(1), pp. 55–63 (1998).

Maeda, Tatsuya et al., "A two–component system that regulates an osmosensing MAP kinase cascade in yeast," *Nature*, vol. 369, pp. 242–245 (May 19, 1994).

Alex, Lisa A. et al., "Hyphal development in Neurospora crassa: Involvement of a two–component histidine kinase," *Proc. Natl. Acad. Sci, USA*, vol. 93, pp. 3416–3421 (Apr., 1996).

Chang, Caren et al., "Arabidopsis Ehtylene–Response Gene ETR1: Similarity of Product to Two–Component Regulators," *Science*, vol. 262, pp. 539–544 (Oct. 22, 1993).

* cited by examiner

Primary Examiner—Elizabeth F. McElwain
(74) *Attorney, Agent, or Firm*—Janet Sleath; Ann W. Speckman; Susan J. Friedman

(57) ABSTRACT

Novel isolated polynucleotides that encode polypeptides involved in plant cell signaling are provided, together with DNA constructs comprising such polynucleotides. Methods for using such constructs for the modulation of cell signaling in plants are also disclosed, together with transgenic plants comprising such constructs.

18 Claims, No Drawings

COMPOSITIONS ISOLATED FROM PLANT CELLS AND THEIR USE IN THE MODIFICATION

FIELD OF THE INVENTION

This invention relates to the field of modifying the responses of plant cells to external signals, such as environmental changes, and developmental cues. More specifically, this invention provides isolated polynucleotides encoding polypeptides that are integrally located in plant cell membranes and that mediate cellular signaling processes.

BACKGROUND OF THE INVENTION

Plants progress through set developmental programs throughout the course of their lifetimes. This is particularly evident in embryogenesis and floral development. There are a variety of signal molecules produced by certain cells in the plant to which other cells, particularly in the meristematic regions, are poised to respond. These signal molecules trigger distinct sets of developmental programs at specific times that lead to the formation of, for example, flowers or cotyledons. In addition to the programmed developmental pathways, plants are exposed to a variety of environmental stimuli such as changes in temperature and amount of sunlight, availability of water, wounding from mechanical injury and attack by pathogens. Environmental factors, such as exposure to light, heat, cold, drought, etc., activate the expression of genes and synthesis of proteins and other compounds essential for an appropriate response to the environmental signal and thereby, the healthy development of the plant. These responses, like the developmental pathways, are mediated by signal molecules.

To respond to these signal molecules, plant cells produce surface receptor proteins that serve as sensors, regulators and/or transducers of cell signals. The intracellular transduction of a signal is often transmitted via a phosphorylation cascade of molecules that culminates in the transcription of genes to elicit the appropriate cellular response either for normal development or against environmental challenge.

One major class of receptor proteins is the single-transmembrane family, of which there are several subclasses. These proteins are characterized by three domains: an extracellular signal molecule (or ligand) recognition/binding domain, a single cell membrane-spanning domain and an intracellular signal transduction domain which is usually a protein kinase. Many, but not all, plant single transmembrane proteins belong to the subclass known as receptor-like kinases (RLKs). The intracellular kinase domains of plant RLKs are all serine/threonine protein kinases, while the extracellular domains of RLKs are of different types. One type of RLK is characterized by the presence of the extracellular S-domain, originally described in self-incompatibility-locus glycoproteins that inhibit self-pollination. The S-domain is recognized by an array of ten cysteine residues in combination with other conserved residues. Another class of RLKs has an extracellular domain distinguished by leucine rich repeats (LRR) that are involved in protein-protein interactions. Binding of ligands to the extracellular domain is followed by receptor dimerization, autophosphorylation and the activation of a series of intracellular proteins which serve to transduce the signal to the nucleus. The structure of plant RLKs is very similar to receptors found in cell signaling pathways in animal systems.

One example of a plant RLK is the Xa21 gene, which confers resistance to the plant pathogen *Xanthomonas oryzae* pv. oryzae race 6. This gene was cloned using genetic means comparing Xanthomonas-sensitive and resistant strains of rice (Song et al. *Science* 270:1804–1806, 1995), and has been subsequently shown to confer resistance to Xanthomonas in Arabidopsis. The 1025 amino acid protein shows a number of features with similarity to known protein domains including a $NH_2$-terminal 23 amino acid residue signal peptide, indicating that the protein is directed to the plasma membrane. Amino acids 81 to 634 contain 23 imperfect copies of a 24-amino acid LRR. Amino acids 651 to 676 encode a 26-amino acid hydrophobic segment that is likely to form a membrane-spanning domain. The C-terminal amino acids contain a putative intracellular serine threonine kinase domain carrying 11 subdomains with all 15 invariant amino acids that are typical of protein kinases. Subdomains VI and VIII are indicative of serine-threonine phosphorylation specificity. Xa21 has strong similarities to other RLKs, such as the Arabidopsis receptor-like kinase proteins RLK5 and TMK1, showing conservation of both the LRR and protein kinase domains. It is not yet known to what protein Xa21 transduces its pathogen recognition signal.

Another kind of membrane receptor molecules expressed by plant cells is histidine kinases (HKs). HKs have been known for some time in bacterial signal transduction systems, where they form one half of a two-component signaling system. The bacterial HK serves as a sensor molecule for extracellular signals, such as changes in osmoticum, nutrients and toxins. The HK autophosphorylates on a histidine residue in response to ligand binding. This phosphohistidine donates its phosphate group to an aspartate residue of the second member of the two component system, known as the response regulator (RR). The phosphorylated RR then binds DNA in a sequence-specific manner, serving to directly activate specific genes which code for proteins that mediate the response to the extracellular stimulus.

Like bacteria, plant cells have a two-component signaling system which consists of a sensor element HK and a RR. The two components may be separate molecules or may exist as a hybrid molecule (hereinafter referred to as hybrid HK/RR proteins). The HK proteins are distinguished by well-conserved amino acid motifs that occur in a specific order. From the amino terminus, the conserved regions are identified as the H, N, G1, F and G2 boxes. These motifs are usually found within a 200–250 amino acid span of the protein. The G1, F and G2 boxes are thought to be involved in nucleotide binding. As in bacteria, upon receiving the extracellular signal, the HK is autophosphorylated on the histidine residue contained in the H box. The phosphate group is subsequently transferred to the RR. All HKs are believed to phosphorylate a RR, as an obligate part of signal transduction. RRs are characterized by the absolute conservation of an aspartate which is phosphorylated by the phosphohistidine of the HK, and a conserved lysine residue. Unlike bacteria, RRs in plants have not been shown to bind DNA directly. Rather, all the plant RR's characterized to date appear to transduce the signal into protein kinase cascades, which eventually phosphorylate and either activate or inactivate transcription factors, and thereby gene expression.

The ethylene receptor (ETR1; Chang et al. *Science* 262:539–544) is the best known two-component signaling system in plants. Ethylene is a well known signal molecule that is involved in the regulation of plant development as well as the coordination of fertilization, senescence, skoto/photomorphogenesis and responses to pathogens and mechanical injury. The ethylene receptor is a hybrid HK/RR protein. The signal is transduced through the protein CTR1, which is a Raf-like protein kinase. CTR1 is a negative regulator of downstream steps in the signaling pathway. While the details of this pathway remain unclear, it appears that the HK is constitutively active in the absence of ethylene, thereby constantly phosphorylating CTR1, which in turn represses other genes in the ethylene response pathway. Binding of ethylene to ETR1 inhibits the HK function of the receptor, resulting in the inhibition of the negative regulator CTR1, thereby allowing the activation of downstream proteins in the ethylene signal transduction cascade. This culminates in activation of ethylene response genes.

Recently, two RR genes, IBC6 and IBC7, which are induced in response to the plant growth regulator cytokinin, have been cloned from *Arabidopsis thaliana* and characterized (Brandstatter and Kieber, *The Plant Cell* 10:1009–1019, 1998). It is likely that IBC6 and IBC7 are involved in the transduction of the cytokinin signal in plants. This is particularly interesting in light of the fact that a gene encoding the hybrid HK/RR protein CKI1 (Kakimoto, *Science* 274:982–985, 1996) causes cytokinin-like effects when it is ectopically expressed in transgenic plants. Thus it appears likely that a two-component HK/RR system is involved in cytokinin signal transduction. Cytokinin is known to regulate plant growth and development, including such physiological events as nutrient metabolism, expansion and senescence of leaves, and lateral branching.

While polynucleotides encoding proteins involved in plant cell signaling have been isolated for certain species of plants, genes encoding many such proteins have not yet been identified in a wide range of plant species. Thus, there remains a need in the art for materials which may be usefully employed in the modification of cell signaling in plants.

SUMMARY OF THE INVENTION

Briefly, the present invention provides polynucleotides isolated from eucalyptus and pine which encode polypeptides involved in cell signaling, together with methods for the use of such polynucleotides and polypeptides. Such polypeptides function as sensor-regulators or receptor kinases. The isolated polynucleotides and polypeptides may be usefully employed in the modification of plant cell responses either during the growth and development of a plant, or under conditions of stress resulting from pathogens or environmental factors.

In a first aspect, the present invention provides isolated and purified polynucleotides obtainable from eucalyptus and pine which encode RLKs, HKs, RRs or hybrid HK/RR proteins. In one embodiment, the isolated polynucleotides comprise a DNA sequence selected from the group consisting of: (a) sequences recited in SEQ ID NO: 1–67; (b) complements of the sequences recited in SEQ ID NO: 1–67; (c) reverse complements of the sequences recited in SEQ ID NO: 1–67; (d) reverse sequences of the sequences recited in SEQ ID NO: 1–67; and (e) sequences having either 40%, 60%, 75% or 90% identical nucleotides, as defined herein, to a sequence of (a)–(d).

In a further aspect, isolated polypeptides encoded by an inventive DNA sequence are provided. In one embodiment, such polypeptides comprise an amino acid sequence selected from the group consisting of SEQ ID NO: 68–130.

In another aspect, the invention provides DNA constructs comprising a polynucleotide of the present invention, either alone, in combination with one or more other polynucleotides disclosed herein, or in combination with one or more known DNA sequences, together with transgenic cells comprising such constructs.

In a related aspect, the present invention provides DNA constructs comprising, in the 5'–3' direction, a gene promoter sequence; an open reading frame coding for at least a functional portion of a polypeptide encoded by an inventive polynucleotide or a variant thereof; and a gene termination sequence. The open reading frame may be orientated in either a sense or antisense direction. DNA constructs comprising an untranslated, or non-coding, region of a gene coding for a cell membrane polypeptide encoded by the above polynucleotides or a nucleotide sequence complementary to a non-coding region, together with a gene promoter sequence and a gene termination sequence, are also provided. Preferably, the gene promoter and termination sequences are functional in a host plant. Most preferably, the gene promoter and termination sequences are those of the original genes but others generally used in the art, such as the Cauliflower Mosaic Virus (CaMV) promoter, with or without enhancers such as the Kozak sequence or Omega enhancer, and *Agrobacterium tumefaciens* nopaline synthase terminator may be usefully employed in the present invention. Tissue-specific promoters may be employed in order to target expression to one or more desired tissues. The DNA construct may further include a marker for the identification of transformed cells.

In a further aspect, transgenic cells, preferably plant cells, comprising the DNA constructs of the present invention are provided, together with organisms, preferably plants, comprising such transgenic cells, and fruit and seeds of such plants.

In yet another aspect, methods for modifying cell signaling in a target organism, such as a plant, are provided, such methods including stably incorporating into the genome of the plant a DNA construct of the present invention. In a preferred embodiment, the target plant is a woody plant, preferably selected from the group consisting of eucalyptus and pine species, most preferably from the group consisting of *Eucalyptus grandis* and *Pinus radiata*. In a related aspect, a method for producing a target organism, such as a plant, having modified cell signaling is provided, the method comprising transforming a plant cell with a DNA construct of the present invention to provide a transgenic cell and cultivating the transgenic cell under conditions conducive to regeneration and mature plant growth.

In yet a further aspect, the present invention provides methods for modifying the activity of a polypeptide in a target organism, such as a plant, comprising stably incorporating into the genome of the plant a DNA construct of the present invention. In a preferred embodiment, the target plant is a woody plant, preferably selected from the group consisting of eucalyptus and pine species, most preferably from the group consisting of *Eucalyptus grandis* and *Pinus radiata*.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

DETAILED DESCRIPTION

The present invention provides isolated and purified polynucleotides that encode proteins involved in plant cell signaling. As discussed above, cell signaling is known to play a critical role in the growth and development of plants, and in cellular responses to external stimuli, such as environmental factors and disease pathogens. Transformation of plants with polynucleotides that encode proteins involved in cell signaling may thus be employed to modify properties such as cell proliferation, differentiation, elongation and survival; resistance to disease; and nutrient metabolism.

For example, the HK ETR1 is known to be involved in ethylene signal transduction. Modulation of ETR1 expression will thus lead to a modification of physiological properties regulated by ethylene, such as fruit ripening, and senescence of leaves and flowers. Modulation of the expression of this protein in transgenic plants may therefore be employed to prolong the useful life of cut flowers by delaying senescence. Additionally, modulation of the expression of ETR1 could be used to selectively enhance the senescence of reproductive organs, resulting in engineered sterile plants.

The HK protein CKI1 has been implicated in cytokinin signal transduction. Its over expression is known to result in cytokinin-like effects in mutant plants. Cytokinin has been shown to play critical roles in lateral branching, leaf expansion, cell division, nutrient distribution, and delaying senescence, among other physiological phenomena. Therefore, modulation of the expression of CKI1 may result in, for example, the delay of senescence in selected cell types or organs. This would result in prolonged shelf life for fruits and vegetables between harvest and consumption. Alternatively, modulation of CKI1 expression may be used to decrease branching frequency in forest tree species, resulting in long stretches of valuable knot-free clear wood for use in solid timber furniture and veneers.

Using the methods and materials of the present invention, the amount of a specific plant cell polypeptide may be increased or reduced by incorporating additional copies of genes encoding the polypeptide into the genome of a target organism, such as a plant. Similarly, an increase or decrease in the amount of the polypeptide may be obtained by transforming the target organism with antisense copies of such genes.

In one embodiment, the present invention provides isolated polynucleotides encoding, or partially encoding, plant polypeptides that are involved in cell signaling, the polynucleotides being derived from eucalyptus and pine. Specifically, the present invention provides isolated polynucleotides encoding RLKs from *Eucalyptus grandis* (SEQ ID NO: 2, 8, 9, 11, 15, 18, 19, 21–25, 33, 34 and 38) and *Pinus radiata* (SEQ ID NO: 1, 3–7, 10, 12–14, 16, 17, 20, 26–32, 35–37, 39–41), and isolated polynucleotides encoding at least one member of a two-component signaling system (HKs, RRs or hybrid HK/RR proteins) from *Eucalyptus grandis* (SEQ ID NO: 42, 48–52, 55–58 and 67) and *Pinus radiata* (SEQ ID NO: 43–47, 53, 54 and 59–66). Complements of such isolated polynucleotides, reverse complements of such isolated polynucleotides and reverse sequences of such isolated polynucleotides are also provided, together with variants of such sequences, as defined below.

In another embodiment, the present invention provides isolated polypeptides encoded by the DNA sequences of SEQ ID NO: 1–67. In specific embodiments, such isolated polypeptides include an amino acid sequence of SEQ ID NO: 68–130. The present invention also encompasses DNA sequences that differ from the disclosed sequences but which, due to the degeneracy of the genetic code, encode a polypeptide which is the same as that encoded by a DNA sequence disclosed herein.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al. (1995), Antisense techniques, *Methods in Enzymol.* 254(23): 363–375; and Kawasaki et al. (1996), *Artific. Organs* 20 (8): 836–848.

The term "polypeptide", as used herein, encompasses amino acid chains of any length including full length proteins, wherein amino acid residues are linked by covalent peptide bonds. Polypeptides of the present invention may be purified natural products, or may be produced partially or wholly using recombinant or synthetic techniques.

All of the polynucleotides and polypeptides described herein are isolated and purified, as those terms are commonly used in the art.

The definition of the terms "complement", "reverse complement" and "reverse sequence", as used herein, is best illustrated by the following example. For the sequence 5' AGGACC 3', the complement, reverse complement and reverse sequence are as follows:

| | |
|---|---|
| complement | 3' TCCTGG 5' |
| reverse complement | 3' GGTCCT 5' |
| reverse sequence | 5' CCAGGA 3'. |

As used herein, the term "variant" covers any sequence which has at least about 40%, more preferably at least about 60%, more preferably yet at least about 75% and most preferably at least about 90% identical residues (either nucleotides or amino acids) to a sequence of the present invention. The percentage of identical residues is determined by aligning the two sequences to be compared, determining the number of identical residues in the aligned portion, dividing that number by the total length of the inventive, or queried, sequence and multiplying the result by 100.

Polynucleotide or polypeptide sequences may be aligned, and percentage of identical nucleotides in a specified region may be determined against another sequence, using computer algorithms that are publicly available. Two exemplary algorithms for aligning and identifying the similarity of polynucleotide sequences are the BLASTN and FASTA algorithms. The similarity of polypeptide sequences may be examined using the BLASTP algorithm. Both the BLASTN and BLASTP software are available on the NCBI anonymous FTP server (ftp://ncbi.nlm.nih.gov) under/blast/executables/. The BLASTN algorithm version 2.0.4 [Feb. 24, 1998], set to the default parameters described in the documentation and distributed with the algorithm, is preferred for use in the determination of variants according to the present invention. The use of the BLAST family of algorithms, including BLASTN and BLASTP, is described at NCBI's website at URL http://www.ncbi.nlm.nih.gov/BLAST/newblast.html and in the publication of Altschul, Stephen F., et al. (1997), "Gapped BLAST and PSI-BLAST: a new generation of protein database search programs", *Nucleic Acids Res.* 25:3389–3402. The computer algorithm FASTA is available on the Internet at the ftp site ftp://ftp.virginia.edu/pub/fasta/. Version 2.0u4, February 1996, set to the default parameters described in the documentation and distributed with the algorithm, is preferred for use in the determination of variants according to the present invention. The use of the FASTA algorithm is described in W. R. Pearson and D. J. Lipman, "Improved Tools for Biological Sequence Analysis," *Proc. Natl. Acad. Sci. USA* 85:2444–2448 (1988) and W. R. Pearson, "Rapid and Sensitive Sequence Comparison with FASTP and FASTA," *Methods in Enzymology* 183:63–98 (1990).

The following running parameters are preferred for determination of alignments and similarities using BLASTN that contribute to E values (as discussed below) and percentage identity: Unix running command: blastall -p blastn -d embldb -e 10 -G 1 -E 1 -r 2 -v 50 -b 50 -i queryseq -o results; and parameter default values:
-p Program Name [String]
-d Database [String]
-e Expectation value (E) [Real]
-G Cost to open a gap (zero invokes default behavior) [Integer]
-E Cost to extend a gap (zero invokes default behavior) [Integer]
-r Reward for a nucleotide match (blastn only) [Integer]
-v Number of one-line descriptions (V) [Integer]
-b Number of alignments to show (B) [Integer]
-i Query File [File In]
-o BLAST report Output File [File Out] Optional
For BLASTP the following running parameters are preferred: blastall -p blastp -d swissprotdb -e 10 -G 1 -E 1 -v 50 -b 50 -i queryseq -o results
-p Program Name [String]
-d Database [String]
-e Expectation value (E) [Real]
-G Cost to open a gap (zero invokes default behavior) [Integer]
-E Cost to extend a gap (zero invokes default behavior) [Integer]
-v Number of one-line descriptions (v) [Integer]
-b Number of alignments to show (b) [Integer]
-I Query File [File In]
-o BLAST report Output File [File Out] Optional The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" or E values for alignments. The E value indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a 90% probability of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the parameters discussed above.

Variant polynucleotide sequences will generally hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

As used herein, the term "x-mer," with reference to a specific value of "x," refers to a polynucleotide comprising at least a specified number ("x") of contiguous residues of any of the polynucleotides identified as SEQ ID NO: 1–67. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 1–67 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NO: 1–67 or a variant of one of the polynucleotides identified as SEQ ID NO: 1–67.

The inventive polynucleotides may be isolated by high throughput sequencing of cDNA libraries prepared from *Eucalyptus grandis* and *Pinus radiata* as described below in Examples 1 and 2. Alternatively, oligonucleotide probes based on the sequences provided in SEQ ID NO: 1–67 can be synthesized and used to identify positive clones in either cDNA or genomic DNA libraries from *Eucalyptus grandis* and *Pinus radiata* by means of hybridization or PCR techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art, and include those taught by Sambrook et al., Ibid. Positive clones may be analyzed by restriction enzyme digestion, DNA sequencing or the like.

In addition, the DNA sequences of the present invention may be generated by synthetic means using techniques well known in the art. Equipment for automated synthesis of oligonucleotides is commercially available from suppliers such as Perkin Elmer/Applied Biosystems Division (Foster City, Calif.) and may be operated according to the manufacturer's instructions.

In one embodiment, the DNA constructs of the present invention include an open reading frame coding for at least a functional portion of a polypeptide encoded by a polynucleotide of the present invention or a variant thereof. As used herein, the "functional portion" of a polypeptide is that portion which contains the binding site or the catalytic signal transduction site of the protein. The functional portion can be determined by targeted mutagenesis and screening of modified protein products with protocols well known in the art. Normally, the functional portion is 10–20 amino acids in length, but can be shorter or longer. The active site may be made up of separate portions present on one or more polypeptide chains and will generally exhibit high substrate specificity. The term "polypeptide encoded by a polynucleotide" as used herein, includes polypeptides encoded by a nucleotide sequence which includes the partial isolated DNA sequences of the present invention.

The open reading frame is inserted in the DNA construct in a sense or antisense orientation, such that transformation of a target plant with the DNA construct will lead to a change in the amount of polypeptide compared to the wild-type plant. Transformation with a DNA construct comprising an open reading frame in a sense orientation will generally result in over-expression of the selected gene, while transformation with a DNA construct comprising an open reading frame in an antisense orientation will generally result in reduced expression of the selected gene. A population of plants transformed with a DNA construct comprising an open reading frame of the present invention in either a sense or antisense orientation may be screened for increased or reduced expression of the gene in question using techniques well known to those of skill in the art, and plants having the desired phenotypes may thus be isolated.

Alternatively, expression of a gene involved in plant cell signaling may be inhibited by inserting a portion of an open reading frame of the present invention, in either sense or antisense orientation, in the DNA construct. Such portions need not be full-length but preferably comprise at least 25 and more preferably at least 50 residues of an inventive DNA sequence. A longer portion or even the full length DNA corresponding to the complete open reading frame may be employed. The portion of the open reading frame does not need to be precisely the same as the endogenous sequence, provided that there is sufficient sequence similarity to achieve inhibition of the target gene. Thus a sequence derived from one species may be used to inhibit expression of a gene in a different species.

In a second embodiment, the inventive DNA constructs comprise a DNA sequence including an untranslated region of a gene coding for a polypeptide encoded by a polynucleotide of the present invention, or a DNA sequence complementary to such untranslated region. Examples of untranslated regions which may be usefully employed in such constructs include introns and 5'-untranslated leader sequences. Transformation of a target plant with such a DNA construct may lead to a reduction in the amount of the polypeptide expressed in the plant by the process of cosuppression, in a manner similar to that discussed, for example, by Napoli et al. (*Plant Cell* 2:279–290, 1990) and de Carvalho Niebel et al. (*Plant Cell* 7:347–358, 1995).

Alternatively, regulation of polypeptide expression can be achieved by inserting appropriate sequences or subsequences (e.g. DNA or RNA) in ribozyme constructs (McIntyre C L, Manners J M, *Transgenic Res.*, 5(4): 257–262, 1996). Ribozymes are synthetic RNA molecules that comprise a hybridizing region complementary to two regions, each of which comprises at least 5 contiguous nucleotides of a mRNA molecule encoded by one of the inventive polynucleotides. Ribozymes possess highly specific endonuclease activity, which autocatalytically cleaves the mRNA.

The DNA constructs of the present invention further comprise a gene promoter sequence and a gene termination sequence, operably linked to the DNA sequence to be transcribed, which control expression of the gene. The gene promoter sequence is generally positioned at the 5' end of the DNA sequence to be transcribed, and is employed to initiate transcription of the DNA sequence. Gene promoter sequences are generally found in the 5' non-coding region of a gene but they may exist downstream of the open reading frame, in introns (Luehrsen, K. R., *Mol. Gen. Genet.* 225:81–93, 1991) or in the coding region, as for example in a plant defense gene (Douglas et al. *EMBO J.* 10:1767–1775, 1991).

A variety of gene promoter sequences which may be usefully employed in the DNA constructs of the present invention are well known in the art. The gene promoter sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the Cauliflower Mosaic Virus 35S (CaMV 35S) promoter, will affect the activity of the enzyme in all parts of the plant. Use of a tissue specific promoter will result in production of the desired sense or antisense RNA only in the tissue of interest. With DNA constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the gene in question, or promoters from a specific tissue-targeted gene in the organism to be transformed, such as eucalyptus or pine, are used. Other examples of gene promoters which may be usefully employed in the present invention include mannopine synthase (mas), octopine synthase (ocs) and those reviewed by Chua et al. (*Science*, 244:174–181, 1989).

The gene termination sequence, which is located 3' to the DNA sequence to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. In one embodiment, terminator sequences are those from the original enzyme gene or from the target species to be transformed.

The DNA constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al. in *Methods for Plant Molecular Biology*, A. Weissbach and H. Weissbach, eds., Academic Press Inc., San Diego, Calif. (1988)). Transformed cells can thus be identified by their ability to grow in media containing the antibiotic in question. Alternatively, the presence of the desired construct in transformed cells can be determined by means of other techniques well known in the art, such as Southern and Western blots.

Techniques for operatively linking the components of the inventive DNA constructs are well known in the art and include the use of synthetic linkers containing one or more restriction endonuclease sites as described, for example, by Sambrook et al., (*Molecular Cloning: A Laboratory Manual*, Cold Spring Harbor Laboratories, Cold Spring Harbor, N.Y., 1989). The DNA construct of the present invention may be linked to a vector having at least one replication system, for example *E. coli,* whereby after each manipulation, the resulting construct can be cloned and sequenced and the correctness of the manipulation determined.

The DNA constructs of the present invention may be used to transform a variety of target organisms, including plants, both monocotyledonous angiosperms(e.g. grasses, corn, grains, oat, wheat and barley), dicotyledonous angiosperms (e.g. Arabidopsis, tobacco, legumes, alfalfa, oaks, eucalyptus, maple), and Gymnosperms (e.g. Scots pine (Aronen, Finnish Forest Res. Papers, vol. 595, 1996), white spruce (Ellis et al., *Biotechnology* 11:94–92, 1993), and larch (Huang et al., *In Vitro Cell* 27:201–207, 1991)). In a preferred embodiment, the inventive DNA constructs are employed to transform woody plants, herein defined as a perennial tree or shrub whose stem increases in diameter each year by the addition of woody tissue. Preferably the target plant is selected from the group consisting of eucalyptus and pine species, most preferably from the group consisting of *Eucalyptus grandis* and *Pinus radiata.* Other species which may be usefully transformed with the DNA constructs of the present invention include, but are not limited to: pines such as *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana;* other gymnosperms, such as *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata;* Eucalypts, such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus novaanglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo* and *Eucalyptus youmanni;* and hybrids between any of the above species.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by Agrobacterium Ti plasmid technology, as described, for example by Bevan (*Nucl. Acid Res.* 12:8711–8721, 1984). Targets for the introduction of the DNA constructs of the present invention include tissues, such as leaf tissue, dissociated cells, protoplasts, seeds, embryos, meristematic regions; cotyledons, hypocotyls, and the like. One method for transforming eucalyptus and pine is a biolistic method using pollen (see, for example, Aronen 1996, Finish Forest Res. Papers vol. 595, 53pp) or easily regenerable embryonic tissues.

Once the cells are transformed, cells having the inventive DNA construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., Somatic embryogenesis in woody plants. In: Thorpe, T. A. ed., 1995: *In Vitro Embryogenesis of Plants.* Vol. 20 in Current Plant Science and Biotechnology in Agriculture, Chapter 12, pp. 471–540. Specific protocols for the regeneration of spruce are discussed by Roberts et al., (Somatic Embryogenesis of Spruce. In: *Synseed. Applications of synthetic seed to crop improvement.* Redenbaugh, K., ed. CRC Press, Chapter 23, pp. 427–449, 1993). The resulting transformed plants may be reproduced sexually or asexually, using methods well known in the art, to give successive generations of transgenic plants.

As discussed above, the production of RNA in target plant cells can be controlled by choice of the promoter sequence. A target plant may be transformed with more than one DNA construct of the present invention, thereby modulating the activity of more than one polypeptide, affecting polypeptide activity in more than one tissue, or affecting polypeptide activity at more than one expression time. Similarly, a DNA construct may be assembled containing more than one open reading frame coding for a polypeptide encoded by a polynucleotide of the present invention or more than one untranslated region of a gene coding for such a polypeptide.

The polynucleotides of the present invention may also be employed in combination with other known sequences encoding polypeptides involved in plant cell signaling.

The isolated polynucleotides of the present invention may also be employed as probes to isolate DNA sequences encoding polypeptides involved in cell signaling from other plant species, using techniques well known to those of skill in the art, such as routinely used DNA hybridization and PCR techniques.

The inventive polynucleotides, polypeptides expressed by such polynucleotides and antibodies to such polypeptides may be used to screen for molecules that interact with such polynucleotides and/or polypeptides and that thereby modulate cell signaling. Techniques for performing such assays are well known in the art. Similarly, the polynucleotides and corresponding expressed polypeptides of the present invention may be employed in studies designed to elucidate the mechanism of cell signaling pathways.

The following examples are offered by way of illustration and not by way of limitation.

EXAMPLE 1

Isolation and Characterization of cDNA Clones from *Eucalyptus grandis*

*Eucalyptus grandis* cDNA expression libraries were constructed and screened as follows.

mRNA was extracted from specific plant tissues, such as trunk xylem, using the protocol of Chang et al. (*Plant Molecular Biology Reporter* 11:113–116 (1993)) with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spermidine*3 HCl) and extracted with chloroform:isoamyl alcohol, 24:1. mRNA was precipitated with ethanol and the total RNA preparate was purified using a Poly(A) Quik mRNA Isolation Kit (Stratagene, La Jolla, Calif.). A CDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 μl of sample DNA from the 5 μl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequence for positive clones was obtained using a Perkin Elmer/Applied Biosystems Division Prism 377 sequencer. cDNA clones were sequenced first from the 5' end and, in some cases, also from the 3' end. For some clones, internal sequence was obtained by designing primers to hybridise to the ends of known sequences, and using these as sequencing primers extending the amount of sequence information. This procedure was repeated iteratively until the complete sequence was obtained. Alternatively, internal sequence was obtained by generating "nested" deletion clones of the gene of interest using published methods (Henikoff, (1984) *Gene* 28 351–359).

The determined cDNA sequence was compared to known sequences in the EMBL database (up to end of August 1998) using the computer algorithms FASTA and/or BLASTN. Multiple alignments of redundant sequences were used to build up reliable consensus sequences. Based on similarity to known sequences from other plant species, the isolated DNA sequences were identified as encoding RLKs (SEQ ID NO: 2, 8, 9, 11, 15, 18, 19, 21–25, 33, 34 and 38) or at least one member of a two-component signaling system (HKs, RRs or hybrid HK/RR proteins; SEQ ID NO: 42, 48–52, 55–58 and 67). The sequences of SEQ ID NO: 2, 8, 9, 11, 15, 18, 19, 21–25, 33, 34 and 38 were found to have less than 10% identical residues (determined as described above) to known sequences.

EXAMPLE 2

Isolation and Characterization of cDNA Clones from *Pinus radiata*

A *Pinus radiata* cDNA expression library was constructed from xylem and screened as described above in Example 1. DNA sequence for positive clones was obtained using forward and reverse primers on a Perkin Elmer/Applied Biosystems Division Prism 377 sequencer and the determined sequences were compared to known sequences in the database as described above.

Based on similarity to known sequences from other plant species, the isolated DNA sequences were identified as encoding RLKs (SEQ ID NO: 1, 3–7, 10, 12–14, 16, 17, 20, 26–32, 35–37 and 39–41) or at least one member of a two-component signaling system (HKs, RRs or hybrid HK/RR proteins; SEQ ID NO: 43–47, 53, 54 and 59–66). The sequences of SEQ ID NO: 3–7, 10, 12–14, 16, 17, 20, 26, 28–32, 35–37 and 39–41 were found to have less than 10% identical residues (determined as described above) to known sequences.

EXAMPLE 3

Use of an Ethylene Receptor Gene to Modify Plant Growth

Transformation of tobacco plants with a *Pinus radiata* ethylene receptor gene homolog is performed as follows. DNA constructs comprising sense and anti-sense constructs containing a DNA sequence including the coding region of an ethylene receptor homolog (SEQ ID NO: 43) from *Pinus radiata* are constructed and inserted into *Agrobacterium tumefaciens* by direct transformation using published methods (see, An G, Ebert P R, Mitra A, Ha S B: Binary Vectors. In: Gelvin S B, Schilperoort RA (eds) *Plant Molecular Biology Manual,* Kluwer Academic Publishers, Dordrecht (1988)). The constructs of sense DNAs are made by direct cloning from PBK-CMV plasmid by cloning cDNA insert into pART7 plasmid, which is then cut by NotI enzyme and 35S-Insert-OCS 3'UTR put into pART27 plant expression vector (See Gleave, A. *Plant Molecular Biology* 20:1203–1207, 1992). The presence and integrity of the transgenic constructs are verified by restriction digestion and DNA sequencing.

Tobacco (*Nicotiana tabacum* cv. Samsun) leaf sections are transformed with the sense and anti-sense ethylene receptor constructs using a method based on that of Horsch et al. (*Science,* 227:1229–1231, 1985). Transformed plants containing the appropriate construct are verified using Southern blot experiments. Expression of the Pinus ethylene receptor homolog in transformed plants is confirmed by isolating total RNA from each independent transformed plant line created with the sense and anti-sense constructs. The RNA samples are analysed in Northern blot experiments to determine the level of expression of the transgene in each transformed line. The expression level of the ethylene receptor polypeptide, encoded by the Pinus ethylene receptor gene and by the endogenous tobacco ethylene receptor gene, for each transformed plant line created with the sense and anti-sense constructs is compared to that of wild-type control plants.

Although the present invention has been described in some detail by way of illustration and example for purposes of clarity of understanding, changes and modifications can be carried out without departing from the scope of the invention which is intended to be limited only by the scope of the claims.

What is claimed is:

1. An isolated polynucleotide consisting of the sequence recited in SEQ ID NO: 9 or its complementary sequence.

2. An isolated polynucleotide consisting of the reverse sequence of a polynucleotide of claim 1.

3. A DNA construct comprising a polynucleotide of claim 1 or claim 2.

4. A transgenic cell comprising a DNA construct according to claim 3.

5. A DNA construct comprising, in the 5'–3' direction:
(a) a gene promoter sequence,
(b) an open reading frame of an isolated polynucleotide of claim 1; and
(c) a gene termination sequence.

6. The DNA construct of claim 5 wherein the open reading frame is in a sense orientation.

7. The DNA construct of claim 5 wherein the open reading frame is in an antisense orientation.

8. The DNA construct of claim 5 wherein the gene promoter sequence and gene termination sequences are functional in a plant host.

9. The DNA construct of claim 5 further comprising a marker for identification of transformed cells.

10. A DNA construct comprising, in the 5'–3' direction:
(a) a gene promoter sequence,
(b) a untranslated region of an isolated polynucleotide of claim 1, and (c) a gene termination sequence.

11. The DNA construct of claim 10 wherein the untranslated region is in a sense orientation.

12. The DNA construct of claim 10 wherein the untranslated region is in an antisense orientation.

13. The DNA construct of claim 10 wherein the gene promoter sequence and gene termination sequences are functional in a plant host.

14. A transgenic plant cell comprising a DNA construct of any one of claims 5–13.

15. A plant comprising a transgenic plant cell according to claim 14, or fruit or seeds thereof.

16. The plant of claim 15 wherein the plant is a woody plant.

17. The plant of claim 16 wherein the plant is selected from the group consisting of eucalyptus, pine, acacia, poplar, sweetgum, teak and mahogany species.

18. A plant comprising a transgenic cell according to claim 4.

* * * * *

UNITED STATES PATENT AND TRADEMARK OFFICE
CERTIFICATE OF CORRECTION

PATENT NO.      : 6,359,198 B1
DATED           : March 19, 2002
INVENTOR(S)     : Timothy J. Strabala and Nicolaas J. Nieuwenhuizen It is certified that error appears in the above-identified patent and that said Letters Patent is hereby corrected as shown below:

<u>Title page,</u>
Item [54], Title, replace "[54] COMPOSITIONS ISOLATED FROM PLANT CELLS AND THEIR USE IN THE MODIFICATION" with
-- [54] COMPOSITIONS ISOLATED FROM PLANT CELLS AND THEIR USE IN THE MODIFICATION OF PLANT CELL SIGNALING --

Signed and Sealed this

Twenty-fourth Day of September, 2002

Attest:

Attesting Officer

JAMES E. ROGAN
Director of the United States Patent and Trademark Office

SEQUENCE LISTING

<160> NUMBER OF SEQ ID NOS: 130

<210> SEQ ID NO 1
<211> LENGTH: 2389
<212> TYPE: DNA
<213> ORGANISM: Pinus radiata

<400> SEQUENCE: 1

```
atctactggt agtgctaatc ccaatctcat tccagtgggt cattaacatg ggctgagagg      60
tttcaaaatc tttatatggt tgttgaagta tccacttcct gtgccaatct tattctcatt     120
ctctgccgtt acaatggaga ggctggagat ggcgatgttt ttaatgttac tgattatctt     180
tttctttaga gattgtgaag cccagggcaa atcggattat catgcactga tagctttcaa     240
ggcctcctct gatatcaata acactctggc gttctcatgg acacataaga atccatgcag     300
acgaaagtgg tatggagttg ggtgtgagaa tggccgggta gtgaggcttg tgctccagga     360
tctcgacctc gtgggtccga ttgatgcctt aacaggtctc catgagctca gaattctgag     420
cttgaagaga aattcactca atggcaccat tcctgatttt ttgaactgga gaagtcttaa     480
gttcctgttt ctctctgata actatttctc aggtcccttg ccttctacca ttgcttcttt     540
agatcatctc ttgagattgg atgtatcgaa caatcatctt ggcggtcaaa taccattgag     600
tattacttca atgacccatt tgcttactct gaggcttgag aacaatgagt tctctggcag     660
catttcagac ttgatgttgc ccaatactgt ggaagaattc aatgtttcag acaatagact     720
tagtggcatg atacctgcaa gtctgtctag gtttccaagc tctggatttg tgaataatga     780
agaactctgt ggaagtcccc tgcagagttg caatgaaagt aacaatgcaa gctctgcttc     840
taatccctac atggcttcca gcccctccat gatttcaggc tcactgccag tgcatagaaa     900
taatagctct acgcaactca gcaaaggtga tattatagca atagttgtgg gagatgttgc     960
agtgttatcg ctcataggtt gtgtaatctt ctgctactac tggaaaaaga agggtgtaaa    1020
acagaagaag cctaagccta agcctgccca gagatgtcca acagacaggt tagctgtgca    1080
ttcttcagat cagtgcccta ataatcagtc tattactgca ggaaaatgca agcttatctt    1140
ctttgatgat ggaagacctt ttgagctaga gcatctcttg cgagcttcgg ctgaaatgct    1200
aggaaagggt aactttggaa gcgcttataa ggctattatg gaagatggat ctgttgttgc    1260
tgtcaagaga ttgaaagatt tgtatggtat tggaaggaag gagtttgagc aacatatgga    1320
gctcatggga agtttgagac atcaaaatgt agttaattta agggcctatt attttgctag    1380
agatgaaaag cttctggtct atgactatat gccaaatggg agtctgtatg cacttcttca    1440
tggtagccga ggacctggta gaacaccct agactggaca actagaatga agatagcact    1500
tggtgcagct aaaggcttgg catttattca cagccactgc aagtcaccca agattggcca    1560
```

-continued

| | |
|---|---|
| cggaaacatc aagtcttcca atattttgtt agacagaaat gggaatgctt gcatttcaga | 1620 |
| ctttggcctt gcactgctgg tgagtccatc agttgctgct tcacgaatgg tgggctacac | 1680 |
| tgctcctgag caagctgcaa caaagaagat atcccagaaa gcggacgtgt acagctttgg | 1740 |
| agttttactg cttgaaatgc taactggcaa ggcccctgtt caagctcaca tgcaagagga | 1800 |
| ttatcattca gctatagatc ttcccaggtg ggtgcagtcc attgtcccag aagaatggac | 1860 |
| atcagaggta tttgatattg agttgatgag attcaaaaac attgaagagg aactagtaag | 1920 |
| catgcttcag attgctttgc tctgtgcctc acaatctcct cagcaacgcc ctaaaatgag | 1980 |
| ccatgtggtg agggtgattc aagacattag aggagatcac cactctccct ccatgcagaa | 2040 |
| ttctctatct caatctcctt ccatgcaaga accaggtcat tctatatcag attctccttc | 2100 |
| tgtatcagag gactcgggaa taagaggcct gtgagtttgt gtatttgttc tcattagaat | 2160 |
| ccaatttgct tgaatttaat tgcaggtatt ctttagcagc atccttttgg atgggcattt | 2220 |
| aactagctgt agcataagag tgtagcatat gcttaaatgg gcatttaagt atatgcagtg | 2280 |
| tgtaggagga ggtatatttt agaagacttg gatttggttt tttcttgaag tatccatatc | 2340 |
| catattaaaa gagttggtat tttggttaag atccaaaaaa aaaaaaaa | 2389 |

<210> SEQ ID NO 2
<211> LENGTH: 2568
<212> TYPE: DNA
<213> ORGANISM: Eucalyptus grandis

<400> SEQUENCE: 2

| | |
|---|---|
| agagagatgg gtttcgcttc cttgcgctcg cagtgtctct tcttcttcct cctctgggtc | 60 |
| ttcatcttct tcgccagccg aagcgacgtg cttgtctccg cagcaacgag cgcggagctg | 120 |
| agctctca tggacatgaa agccagccta gacccggaaa gcaggtatct ttcctcgtgg | 180 |
| accgtcgatg gcgatccttg cgacgggtcc ttccaaggcg tctgctgcga cgacgagggc | 240 |
| cgcgtcgcca acgtttcgct gcaggggaga cggctcaccg ggaggctctc tccggccatt | 300 |
| gctgggctca cccacttgac tggcctttac cttcactaca actccctgtg cggagagatt | 360 |
| ccgcgagagc tcggcaactt gagcgcgctc agcgacttgt atctgaacat gaacaatctc | 420 |
| tccggccaga ttcctcccga gatggctgac gtcgcaagct tgcaagttat gcagctctct | 480 |
| tacaaccagt tgactggaag tatacctaca aagctgggat ctctgaagaa gctcagtgtt | 540 |
| cttgctctgc aatctaatca gctcactggc gcaataccgg caagtttagg tgacctgggg | 600 |
| acgttgacga ggttatattt gagtttcaat cgcctctttg gctcgattcc catgaagata | 660 |
| gccgatctgc tccttctaga agtcttggat gtccaaaaca cactctctc tggcaatgta | 720 |
| cctcctgcgc tgaagagact gaacgaagga tttctgtacg aaaacaactt cgacttgtgt | 780 |
| gggactgggt cctctctttt aaggacttgt aatgctttgg agggtcgaaa gcctagtcaa | 840 |
| cctcaaccct atgggctgc acaacagta cctccacaa gtatacccga acggccaat | 900 |
| gtggtgttac catgtaacct gactgaatgt ctagtttgc caaatcagc gcatccctct | 960 |
| gcgcttattg gatcaatctt ggcaactgtt gcattgtcgg ccatagggtt ccttttgttc | 1020 |
| acacactacc gtcggaggaa acagaaactt ggcttttcgg ctgaggtttg tgatggccat | 1080 |
| ctgagcactg atcaacccaa gagtgcttat aagaaaaatg gctctccttt agctagcctg | 1140 |
| gagtattcca acggatggga tccgcttgct gatgctcgga tctttaatga gttttctgaa | 1200 |
| gaagctttcc agagcttcag attcaatctg gaagaggtta atccgccac tcagtatttc | 1260 |
| tcggagttga atgtgttggg taagagtaat ttctctacca catacagagg aatcctgaga | 1320 |

```
gacggttctg tagtctccat caaatgcatc aataagacta gctgcaaggc tgatgaatca    1380
gagttcttga agggtttgaa tatgttgacc tcactgagac atgaaaatct ggtgaggctg    1440
agaggattct gctgctcaac ggcccgtggt gagtgcttcc tgatatatga ttatgttccg    1500
aatgggactc tgctaagctt tttggatttg gaggaggggg acagtggcac tcttgagtgg    1560
tccactagag tttcgattgt gaagggaatc gctaaaggta ttgcctattt gcacgctcac    1620
aaaccaaaca aggccccccct ccttcaccaa acatctcag cagacaaggt gctcatagac    1680
cagcgattca atccgttgct ctaccaatct ggtctccaca ggctcctgac aaatgatgtt    1740
gtgttctcgt tgctcaaagc tagtgctgcc atgggctacc tagcgcctga gtacatgtcc    1800
acgggccggt tcacagagaa gagtgatgtc tacgcgtttg aatgatcgt gttccagatc    1860 ttgtcgggga agcagaaagt agatcactcc atgcgtctgg ctgctgaatc gtgtagattc    1920
caagaattca ttgatgcgaa tatccatgga aggttcttcg agtacgaggc agctaaactt    1980
gcaaaaatcg cctcgctctg caccaacgag tctccttatg acaggccatc catggacgcc    2040
gtgattcacg agctgagtaa ctgtagcagc tgtctctgat tgtgaggcct tattggagta    2100
aatgttccag gagctgttgc aaaagtcaat ggtagaagtt ggtctgaaaa agctccctgc    2160
gctgccacta atgttgtaac ctaccggctt tgacatcttt ttgatttggt gcctttgcct    2220
tagggccgtg ctttcttgtg tatgttcaag cctggtaggg atgaatgact ttaattcacg    2280
catgtatgat tgcttttcaa atatttttct ttagaagtag gttcatttcg gaattagatt    2340
ttcgatattt ctcgttgcgt gccgcagttg tgtgggtgaa aatggccgtg gacttccaac    2400
gccggtaact agccttgttg ccgtggtcgc attgcattag ccctgcctgg catctttaat    2460
tgctggttaa ttgaggcgat ttgttttttcc attggtggat ctgctggcat ctttaattgc    2520
tggttaatcg aggcgatttg ttttccgta aaaaaaaaa aaaaaaaa            2568

<210> SEQ ID NO 3
<211> LENGTH: 2686
<212> TYPE: DNA
<213> ORGANISM: Pinus radiata

<400> SEQUENCE: 3
gacgaggatc cccaaggccc attgctttat tgcctggaaa gaattttaaa gcttatatat     60
atattattgt tgctctataa tagtaatgat aaatttaggc ctaggcatag gtgtgtcatt    120
gccattctta gaagcaatgc ctggcactgg tcactgccca cagtccagct ctcaaagcct    180
gtcctgtagc tgttgtctca atgccttgtc ttactttgtg agctggtgtc tgtcatggag    240
gtagaggaag aatcatttgg cttttaagtt ttaccccatt tttcttcagt aagaagaagt    300
gcctccatgg tttgcagcag atcggagctt tgctgagacg cgattaggta acccgtctgc    360
gacaattttt tctctgcaat gtgggtttgt tgggcatttt acagaagcat gactggcaga    420 aagaatagc agcaagtata tatctctgtt tttggcttgc tgtgatgtat tggtcgcaga    480 tgggaatat acgcagctt tttaatggtt tcttcatgct ggtgctagta gtggccgtgg    540
ttaaggggga gccaacgggc gataaacagg cccttctcga ttttctcagc aaggttcccc    600
atgggcgaag gctaaactgg aatgccagca gctcagcttg tacttgggtt ggagtgacct    660
gcaatagtaa caaggatcgc atctgggaag ttagattgcc gggcgtggga ctctttggac    720
cgattccccc tggcactctg gggcgtctga cggagctcag agttctttcc ctgagatcaa    780
atttgctcac cggttctctg ccttcagacc ttgcaaatgc caaggctctg agaagtatct    840
```

```
atcttcagca taacttgttt tccggaccat tgcctccgtt tctgtctcaa tgggggcgct      900
tgagtcgact ggatctttcc ttcaatcgtt tgaatgggtc tattccctttt tccttgaata     960
acctcacgca tctcactggt ctcttgttgc agaacaattc gctgagtgga agcatacccca   1020
atctcaacat ccagaacttg actctgttga gtgtggccaa caatcagctc aacggttcga    1080
ttcctaggtc gcttcagaag tttcccaaga cttctttcca aggcaatgct cagctctgcg    1140
gggttccatt aaaactgtgc aaatcgtttt tcccgtcgcc ttctccctct cccaacggtt    1200
ctgctgtgcc ccggaggtcc aagaaatcga agctgagcac cggcgtggtc gtggctatca    1260
tcgtgggcgc cgttgctgtg ctcttcttgt tgctggcatg cctattttttg tgctgcgtta   1320
gaaagcacag gggcgagagt gcgacggaga agcctcagaa agacgagcgg accacggtcg    1380
agaagggcgg gccttctaag gaggaataca tggggactgc ccaggagaca gagcgcaata    1440
agctcgtatt cttcgagggc agccagtata ctttcgacct ggaagatctt ctccgcgctt    1500
ctgcagaggt tctggggaaa ggaagcgtgg ggacggccta caggcagtg ctggaagatg     1560
ggactactgt tgtggtcaaa cgcttgaagg acgtggctgt caacaggagg gattttgaac    1620
agcagatgga gctggtggga aggatccgtc acaggaattt ggtgcccttg agagccttct    1680
acttttccaa agatgagaaa ttactcgtct atgactatat gcccgctggc agcttatcag    1740
ccctttttgca tggtagcaga ggctctggcc gcacaccttt ggattgggaa accaggatgc    1800
ggattgcttt gggtgctgca agggcattt cccacatcca cgaagaaggc ggaggcaaat    1860
tcacccatgg aaacataaag tcatccaatg ttctgttaac gtccgatttg gatggctgcg    1920
tctcagactt cggcctcgtt ccattattta gcgctgctgc agcagcaaac cgcatcgctg    1980
gttacagagc cccggaggtc atagagactc gcaaggtcac acagaaatcc gatgtctaca    2040
gcttcggtgt gctactccta gaacttctca caggcaaggc tcccaaccag gcctctctca    2100
acgacgaggg catcgatctg ccaagatggg tacaatccgt ggttcgcgag gagtggacag    2160
cagaggtttt cgacgtggaa ttaatgaggt accaaaacat agaagaagag atggtccagt    2220
tgctgcagat tgccatggcc tgcgttgcta cagtgcctga tcagaggccc agaatgcaag    2280
acgtggtgaa gatgatcgag gacatgaggc agttcgaaac agacgaagga aatagacaat    2340
cctctgatga taaatcgaaa gaatccaatg gacaaactcc tccccagcaa gccacaccag    2400
aagcacgcac ccccacagca agaacaccgt gacagcaccc cctcagcaag cacactttga    2460
cagtcgaaat tcttctgtttt ctgtccatat tataacacag ttgccagtat catgggcttt   2520
tcgtgattga tttcatttat atccagtatt tcagtaaagt aatttcaccg cggaattgct    2580
tgctttatat tccggtttc gttcccctttt tcttggctcg ctggtgatct tcaagcattc    2640
ttgaaatagg caccacacta cactacattc gtgctcattt gattgg                   2686
```

<210> SEQ ID NO 4
<211> LENGTH: 2868
<212> TYPE: DNA
<213> ORGANISM: Pinus radiata

<400> SEQUENCE: 4

```
gaacacaatg cgggtctgat gtctctccgc gggttttgaag cctgacgagg ctgctcccta    60
gggttgagtt ggaggttgct gcgggagcgg gaggcggggg cgaggctgat catgagatct    120
ggattgtgaa tccgcgtgga tccgtggatg atttaacggg gcgaaagatc gagtctcgtc    180
cccgagggct aagcaggcgg ttgaaataaa gaggtgaagt tattttgagc ggagtcatgc    240
agcagccgta tgttgtactc gccctgttgt ggatgctgct gctgcatcac ccgctctggc    300
```

-continued

```
gagttttgc taatacagaa ggtgatgctt tacatagcct tcggtcgaac ttactggacc    360
caaacaatgt gcttcagagt tgggatccaa ccctcgtcaa tccatgtaca tggtttcatg    420
ttacatgcaa caatgataac agtgtgataa gagtggactt gggaaatgca caactttctg    480
gttcattggt tccccagctt ggcctactga acaatctgca gtacttggag ctttatagca    540
acaatataag tggtcccatc cccagtgatt taggcaactt gaccaatctt gttagcctgg    600
atttatacct gaacaatttc actggtctaa tcccggagtc actgggcaaa ctgtccaggt    660
tacgcttcct tcggcttaat aacaacagtc ttgtaggacg gatcccaatg tctctcacaa    720
ccattactgc tcttcaagtc cttgatctgt caaacaataa tctcacagga gaggttccag    780
caaatggttc attctctcta tttactccta tcagtttcgg tggcaatcaa tacctgtgtg    840
gtccagtggc acaaaagcca tgtccgggat ctcctccttt ttctcctcct cctccgtttg    900
taccacccccc gccagtagct ggaagcaatg gagcaagggt gcagagctct tccagcacag    960
gagccattgc tgggggagta gctgcaggtg ctgccctctt atttgcagct cctgcaattg   1020
ggttcgcctg gtggcgtcgc agaaagccac aggagcactc ctttgatgta cctgctgagg   1080
aggatccaga agttcactta ggccaactta agaggttctc attacgggaa ttacaggttg   1140
caactgatgt ttttagcaat agaaacattc ttggcagagg tggttttgga aaggtgtaca   1200
aagggcgcct tgcagatggt tccttggtgg ctgtaaaacg tctgaaggaa gagcgtacac   1260
cgggtggaga gttgcagttt caaacagaag tggagatgat aagcatggca gtacatagga   1320
acctccttcg actacgtgga ttctgcatga cacccactga acggctgctt gtttatccct   1380
acatggccaa tggaagtgtt gcttcatgcc tacgagagag ggcacaaaat gacccaccct   1440
tagattggcc aactcgcaag cgcatagcat tgggttctgc aagaggtctc tcctacttgc   1500
atgatcattg tgatcctaag attattcacc gggatgtcaa ggctgctaac atcttactgg   1560
atgaagaata tgaggcagtg gtgggggatt ttggcttggc aaaacttatg gattataagg   1620
acacacatgt tacgacggct gttcgtggaa ccattggcca catagcacct gagtacctttt   1680
ctactggaaa gtcttcggaa aagacagacg tatttggata tggaatcatg ttgctggaac   1740
ttattacggg acaacgggca tttgaccttg cacgtttagc aaatgatgat gatgtcatgt   1800
tgcttgactg ggttaaaggc ctactaaaag agagaaggct tgatatgcta gttgatcctg   1860
atcttaagaa caattatgtt gaagcagagg tggaacaact tattcaagtt gcattacttt   1920
gtacacaagg gtcaccaatg gatagaccaa agatgtctga agtggtaagg atgttggaag   1980
gggatggctt agctgagaga tgggaggaat ggcaaaaggt ggaagtcgta cggagccaag   2040
aagttgaact tgttcctcat agaaattcag aatggattgt cgactcaaca gataatcttc   2100
atgcagttga attgtctggt ccaagatgat aagagttgaa ttgtttattc aatcttttgca   2160
aatccataat tttattgagt ccaaattaca atgtcaatat gtatcgaggt tgaatcgatg   2220
tatcattttc aagcatattt tagtagatgc gtcaatgtgc gaatgtagag aatattcgtt   2280
gcaagtcctt agatggctat gctgggtttt gtcccatgag aatttctgtc gggttgcagt   2340
caaacccgaa agttagaagg atttcttatg gtgcatccca tccaggcaaa gatctgggct   2400
cctgtattat gaatggtttg ctctaggaat cgaagctcca tttctgctat tgaagacttc   2460
cttttttcagt gctaatatgt atttaaacag tctgtccact tgacatatgc aactactttt   2520
cctgccgaga gtgtactttg ataagaccac aatcttttga gactagtact aaatttggtc   2580
tcagtttcaa atccagagtg gaaatgaag gaaaacaaat ttcatgaata ccaagattct    2640
```

-continued

| | |
|---|---|
| gctaaatccc ttgagctggg ctcttaattc tcgataatcc tccggagttt gagaaagatg | 2700 |
| tatgttgtca aaggtagatc tcaagctagt gaattcctta gtttcacaga attgttttct | 2760 |
| tagagccaga cacatgctcc tgaattacat taaatttact ttttgtggtg ttcaaattga | 2820 |
| aatacagaaa ctatgactgt tttaatgaca ttggcagcta acggaccg | 2868 |

<210> SEQ ID NO 5
<211> LENGTH: 3340
<212> TYPE: DNA
<213> ORGANISM: Pinus radiata

<400> SEQUENCE: 5

| | |
|---|---|
| gattaccata atgcttctcc tcgccactct ttctttcatt ctctttctca atccttttgc | 60 |
| cttttccaca cccatcgccc atttccctca ccatcctcct cgtctcacca atgcttccga | 120 |
| tcaacacgct ctgcttgcat tcaagtctgc aatcacatat gatccctcac agtccttggc | 180 |
| cacgtcttgg ttgccaaatg tgtcattctg ccagtggacg ggcatcatat gcagcaggcg | 240 |
| cagacagaga gttatttccc tcaatgtttc gagcatggga ttacaaggta caatctctcc | 300 |
| ccttctcgcc aatctctcct ttcttacagt actcgacctt cacaacaaca gtttcgactg | 360 |
| ccacattccc tatcaattgg gaaccctctt tcgcttaaag atgcttcgcc tgtctaagaa | 420 |
| tcaactccag ggttccattc cgcccactct ggctaattgt cgcagtttac ggaacttgac | 480 |
| tctctccttt aacaacctca cgggaaacat tcccccacaa ctatgccttc tcccaacct | 540 |
| aatatgtatg tccttgggaa ttaacaattt gacgggaaca atcccggact gcttgggaaa | 600 |
| catatcctct ttgcagtact tatctttgag tcaaggtaac cttcagggca gtgtcccttc | 660 |
| cgaattgggt aggctaagcc agctcatcgt tcttgatctg tttgggaacc atctcacggg | 720 |
| atgcattccg tcttcgttgt ccaactgcac caatcttgaa ctattggata taggtgataa | 780 |
| ccaattagtt ggccacattc cgtcgcattt gtgtaccaag aagaccaccc agttaatgta | 840 |
| tctccgtctg ggtgctaatc agctaagtgg cagcgttcct tcatccctct tcaattgtac | 900 |
| caagttacaa gagattgcct taccatataa ccagctcagc ggaatagtgc ctatggagtt | 960 |
| gggtaaattg acacatctcc agcggctttt ctttggcggg aattacttta ttagcggcaa | 1020 |
| caccatgaga tgccccattc ttactgctct tagtaactgt tctgatctac aatatgtaga | 1080 |
| cttatctgag aataacttca ctgggcaatt gccgttttct ataggccacc tctccaaaaa | 1140 |
| actctaccat ttagacttgg gtagcaacga attagctgga gaaatacctc cggctattgg | 1200 |
| aaatttaagt agcctaacat tccttaattt aggacgtaat tattttacag ggtcaatccc | 1260 |
| atcttcactt attatgcttc agaagttgga gaggttatat atggattcca ataatttaca | 1320 |
| aggaaacatt ccaatggaaa ttgggcagct aaagagctta ggtctcttat atctttctgg | 1380 |
| aaataatttg tctggaaaaa tccctgattt tgtggccaac ctccagcaat taagatattt | 1440 |
| atatcttaat cataaccagt tatcaggaga tataaatgca aatttaggga aatgtgtgaa | 1500 |
| cttactactg ctagatctat catacaacaa gcttagtggg cacataccct caagagctcgc | 1560 |
| aggccttgca aatttagcct tctatttcaa cttgtcaaac aatttattaa gtggccatgt | 1620 |
| accttagaa ctaggaaagt tcgatatgct tcaagccata gatatttcgg caaatcaaat | 1680 |
| aactggctac attccaagta tcgttggaag ctggaaagaa gtagcatatc tgaatctttc | 1740 |
| ttacaatgca cttgaaggtc caattccagt gtcaatcagt gaacttctaa gtcttcaaga | 1800 |
| cctagatctc tcctccaaca atttgtcggg tggaatacct atatcactag caaatctcac | 1860 |
| aatgctccat cacttgaatt tttcttttaa caagttgtca ggggaagtcc ctaaagaagg | 1920 |

-continued

```
agttttcaaa aatattggcg ccacagcatt tatgggaaat cttggtctat gtggaccttg      1980
ggtaaatcta ccaccgtgct atgctcataa acataaaagt gttttgaatc tcaaaagagt      2040
tatcatactg gttgttgttg tagcaattgt tgtattgtgt ttgtttcttg caatattgtg      2100
gagaaagaat tgtaggagaa atattcagag agacattggt ccatcattaa atgtggggca      2160
tcgaagaatc tcctatgcag agctcgtcat tgcaacaaat gaatttagtg atgcaaactt      2220
gttaggaatt ggtagttttg gaaagtgta caaagggatt ttgatgatg cacaatggt         2280 tgctgtcaag cttctcaatc tacaaaatga aggggctcaa aagagttttg atagagaatg      2340
caaagttttg ggtagagtta gacaccggaa tttgattcgg gtcataactt gctattcaga      2400
tctccaaatc aaagctttga tatttccatt aatgccaaaa ggaagcctag aaaagtggtt      2460
atatcccgat gatggagaac aaagttgttt gaatttgatt caaggttga atatagcaat      2520 agatatcgcc caaggcatga catatctcca tcatcattgc tttgtgcaag tgattcattg      2580
tgatttgaaa cccaacaatg tgttgttggg tgaagatatg actgcatatt aatagactt       2640 tggcattgct actatatgtt ttgcaaataa tgaagatgga gctctcactt ccacaaatgc      2700
actcaaagga tctaccgggt acattcctcc aggtattatt taaactatat cccatatgaa      2760
gcaatcttat gattttctta tgtttactta acattttcaa ttaaattaaa aaacttaaga     2820
tgaggatcta tgaatgcaga atatggagtg ggaggacaag ttacaaccaa aggtgatgtt     2880
tatagctatg gaatagtgct attggaaatg cttactagaa agaagcccac ccatgacata     2940
tttgtggaag gaatgaactt gcaaaaatgg gtgggtagta gttttccaag ccaagtacaa     3000
gaagtggtgg acatgggtct gttaacgagg actagtagat gcattgaaga agataaagat     3060
ctcaattgtc tcagtgcact gataaatgtg ggtttgcttt gcacaaatga atctcctcaa     3120
ggacgaccta caatgatggg cattttaggc acattgcaaa acatcaaaga ctctttttg     3180 agcactactt ccattcccaa attccaatca aatctaacac atttgttggg tagtacaagt     3240
gctactatca acaacatttg tgaaggtcaa agttcttcca catcttagtc tattgtaaca     3300
aagtagtggt tatatgcttt tttgtacata aaaaaaaaa                           3340
```

<210> SEQ ID NO 6
<211> LENGTH: 3396
<212> TYPE: DNA
<213> ORGANISM: Pinus radiata

<400> SEQUENCE: 6

```
ggaggaagcc tgagacgaaa tcattgcagg aggcggatgc ccaacaaata ggttgatgca       60
gggattgcac gcattcttca tttatttgct gtgaaaaatg aggtattcct ggacatgttc      120 tcccttctc agtctcctgt tcattctttc atgtttagat tctggaattt gtctcgataa      180
ccaacaaaca caggtgatga aaaaactgtc gtcctacaca ccctcatgga cgactgtaaa     240
gtctgataac ccatgtggat ggagtggtgt gaattgcact gccgaagaga gtaatgtgac     300
tgagcttcat atgtccggtt ttaggatgaa gggcaatgct tggcagacta tatgcaaact     360
tcaagccctt caagtgcttg acgtctctga taatttgctg tcaaccccgt ctgataatga     420
tatccaggct tgcaccaact tgttttccct taacatcagc tccaattttt tgccaggctc     480
ctcccttcct tcgcttgcac cgatgcgcaa actgcacttc cttgatgtct ctcacaatgg     540
atttgcaggg gaatttggcc cgcagattca gcatttgaca gacctcagag tgctcaattt     600
gacatacaat aacttcagtg gtccaatccc ttcatttta ggaaatctga cgactttaga     660
```

-continued

| | |
|---|---|
| aaaaatcgat ttctctcaaa attattttga gggtgaattt cccaaagagc ttgtgcgttg | 720 |
| cacaagtctg acttatctag acctcagctt caatagactg acaggccaaa tccctgataa | 780 |
| tattagcaac cttatccatt tagaaaccct gattctgtca tcaaataatt taactggaac | 840 |
| gattcctaaa acactggatc gacttgtcaa tttgactcac tttgcatcaa ataagaatca | 900 |
| gctcattgga cgaatacctg ttcagttagc taagctcaca gaattacatt ttcttgatct | 960 |
| gagctacaat gggttaaatg aaaccattcc tccagaactt tttgctttga gcaacttgca | 1020 |
| gactctggac cttacaaaga atttgctcac aggagagatt cctcagaatt tttcgagaaa | 1080 |
| attgataagg ttgcgaatag gccagaatct tcttaaagga acattcctt taacaattgg | 1140 |
| aaattggtct aacttgacat acttagaaat gaatgataac tcactagatg ggcagattcc | 1200 |
| gcagcagctg gtaaattgta tcaagcttca actacttgac ctcggcaaca ataatttgtc | 1260 |
| aggctcatta accaatcagc tgccttcact tctacagttg caagtgttga agttgcataa | 1320 |
| taataatttt gttggaagca ttccatatat actgtcatct ttctctaatt tgtcatatgt | 1380 |
| cgatttgagt gacaatactt taaatgggtc catacccctca aatattttca atctttcgaa | 1440 |
| gctccaaaat ttgcgcctac agaacaacaa gctaacagga gcgattccaa acactgttgg | 1500 |
| aggcagccag gtcttgttag agctccagtt gggtggcaac aacctaactg gaacaatgcc | 1560 |
| attggaaatt ggcttcgtca gaaagttgca aattcaactc aatctcagct gcaattctct | 1620 |
| agaaggggaa attccgaata ctctttctgg tttgtacatg ctagaaatct tggatctttc | 1680 |
| caacaataaa ttgacaggag aagttccagg ttctttgaca gctatgctca gtctcacact | 1740 |
| gttgaacatc tcaaacaata gtttaacagg cgtccttcca aaatttccaa attccacaag | 1800 |
| cgcgttgata attattgata caggaaaccc tggtctcact gctgggcaaa atggttccgc | 1860 |
| tcctgccgct tctgcaagga aaaaaatctc ggcaattttg atcattggag ttgctgttgc | 1920 |
| aggtgctgtc tttgcaattg tggctgttgg attgttcatt gtggccagca aatactttgg | 1980 |
| gcgtggtgat cagcaaatgc cagaagtgca actagcccgt aagattgaag gccattttat | 2040 |
| tcatccagat agtatccaca ggctaaggat tgactttgaa aagggtgttg aagccactct | 2100 |
| agatccggct aatgtcttcc taaagaacaa gtttagtacc tattacaaag ctgtcatgcc | 2160 |
| ttctggcatt agttattccg tgaagaagct caactggagt gacagaattt tcaaatctgg | 2220 |
| aagctaccga aagcttggtg cagaactgga gaaacagggg aagctaaggc atcccaacat | 2280 |
| cctgacaccc ttggcacatg ttctagacac agattctgct tacctttttct acgaatatgt | 2340 |
| tcataaaggc agcctctcag aattccttca cactagtaat gtttctgtat ggattggcc | 2400 |
| atctcgttgc agaattgcca taggtgtagc gcaaggtttg gcttttctac acgggtgtca | 2460 |
| gcatccaatc ttccatcttg atctcactac caaaaacatt ctcctaaagt ctttaacaga | 2520 |
| gccacaaata ggtgatattg agcttttgcaa gattgttgat ccttccaaga gcacagggag | 2580 |
| tatttctgca attgctggtt cagttggata cgttcctcca gaatatgcat acactatgag | 2640 |
| agtgacggct gctggtaatg tctatagctt tggcgtcatt ttgctagagt tactgactgg | 2700 |
| aaggactccc atcaccagtg gaatggatct tgcaaagtgg gttcagtcaa ctctctcagg | 2760 |
| ggaggaaaca tgggaacaaa ttcttgacac aggaatcaga aacttttccg tccaaataca | 2820 |
| gaatgagatg atcgcaatgc tgaaagtagc tctcagttgc gttagctcat ccccagagtc | 2880 |
| gagacccaaa atgagaaatg tagtgggaat gctccagatg gtcaggcaag ttgcagaata | 2940 |
| aggtttttact tcattcgaca atatatggat gagatttttac ttccctacaa tataggagtg | 3000 |
| ggaacggggt attctgtttt atatttttaa ggagactaaa tctgtatagt attgtcgata | 3060 |

-continued

```
tgattaggat tcacatgaat tcagacatgg atatatgagg ttgttaaaat gttggtattt    3120
tttgctcagg ttagcgtagt tatgcagtaa agtgcttatg ctagattatc atggttcata    3180
tcataaatct agtatacttc aagcacaaa tgtataaata tatgtgtttc tgatttgatt     3240
aacggggaag ttattgtctt cattggcatt caaccaaaat atcagttaaa ggtagcaagt    3300
ttatagaatg cttgtggctt tcaaacatgg tcctggcttg tggctaaatc atggtaattc    3360
aagaacacag tctatttgac taaaaaaaaa aaaaaa                              3396
```

<210> SEQ ID NO 7
<211> LENGTH: 2432
<212> TYPE: DNA
<213> ORGANISM: Pinus radiata

<400> SEQUENCE: 7

```
tctcaaagct ctcaatccca ccactattgg acaagaatgg cagaagtgaa gaaaattgtt      60
gagagtttgt cgcattgcac tgcacaatgt gtttcttgat gctctaaagt cccgctcatg     120
tgagttattt tcctgatacc ttatctgtac ttgatgttac ctgatgcatt tcaagatctt     180
gtttgatgca aaggaggaaa aaattaagtc ctctttcgat atgttgactg cctttctggt     240
attgtgcttc actaccactg ctgcgtctgc tacacaacta tctccttcgg gcctcaacta     300
tgaagttgca gctctaatgg cgataaagaa tagtttgaat gatccacata atgtcttaga     360
gaattgggac atcaattcgg tggacccatg cggttggagg atggtgacat gcacacttga     420
aggctctgtt tctatattag gaattcagtg tcagaatttg tctggtagtt tgtctccaag     480
cattcgaaac ctcaccaatc ttcagtctgt gctacttcaa ataacgcca tatcaggatc      540
aatcccagct gagttgggaa agctagataa gcttgatact cttgacctct ccaacaatca     600
tttcaatggg ttgatacca gttcactggg aaaattgaaa aacctaaatt acttgcggct      660
caacaacaac aacctatctg gaccaattcc cccatcactg gctactatca cagggcttac     720
tctcctggat ttgtcgtgca ataatctaag cggctctgtg ccaagaattt ctgctagaac     780
cttcaatatt gtgggcaacc ctttgatttg tggtccgaat tcaacatata agtgtcctgg     840
acaatttccc acgcctatcc cattagttgt tgagacaccg caaggtagag ttccttcaag     900
acaatctaaa accagaaagc tggctgttgc cttggtcgct agtcttggtt ttgtgtttgt      960
ggtttccatt ggacttctcc tttggtggcg caagagacac aatcagcaaa ttttcattga    1020
tgtcaatgaa cagcacaatg ttgatatttg tctagggcat ttgaagagat tctcattcaa    1080
agagttacgt gtttccacta taattttag tagcaagaat attttaggag taggaggata    1140
tggaattgtc tataaaggat tcctacaaga tggcactata gtagcaataa aaaggttgaa    1200
agatggtaat gtgggaggag gagaaattca atttcaaaca gaggtggaaa tgatcagctt    1260
ggctgtgcat aggaacctat tacgattgta tggattttgc acaacctcca gagagaggct    1320
tctggtctat ccctacatgc caaatggaag tgtggcctct tgtcttagag atcatattaa    1380
tggaaagctt gccctggact ggcctactcg caagcgtata gcccttggag cagctagggg    1440
actgttatat ttgcatgagc aatgtgatcc caagattatt caccgggatg tgaaagcagc    1500
aaatatatta ctgatgaat attttgaagc tgttgttgga gattttgggt tagcaaagct    1560
cttggatcac agggattctc atgtgactac tgctgttcga gggacggtag gtcacattgc    1620
cccagaatac ctttcaacgg gacaatcttc agagaaaact gatgtatttg ctttgggat     1680
attactgttg gaactcatta caggacaaag ggctttagat tttggccagg ctgcaaagca    1740
```

-continued

| | |
|---|---|
| aaaagttgta atgctggatt gggtaaagaa gcttcatcaa gagaagaagt tgcacctcct | 1800 |
| tgctgataaa gatcttaagg gcaatttga tagagttgag ctagaagaga tggttcaggt | 1860 |
| ttctttgcta tgcacccaat tcagcctgg acatcgtcca aaaatgtgtg atgttttgag | 1920 |
| aatgttggaa ggtgatggat tgacagaacg gtgggaaaca ttgcaaaaaa ttgaaccccc | 1980 |
| ccgatacaga gtaactgaga tacccataac atattccgag ttggttgaag aagattcttc | 2040 |
| ttggcttgtc caggcaattg agctatctgg tccccgttga tttcacaggc ttgctaacat | 2100 |
| tctaatatca atgcttccat agcttgttgt ctttgcatct tttgttggtg cccatggaaa | 2160 |
| catatgctgg ttcgttgtat aggtagcttt ggtacagtca aaatatttcg ccatgcacca | 2220 |
| aaaaatacgg ataccttat aattgtctct ctatgtaatc tcaggcaaac ttaagcatat | 2280 |
| tcagtatttt ttattgataa gttggtagct ttgcttgtaa tggctatgct gtatcctcgc | 2340 |
| ttgacacttc atcagcagcc tagcttattt gatagtgaag ggttttcaca agaactttct | 2400 |
| cagatggttg taaatggttg ttgagatatt tc | 2432 |

<210> SEQ ID NO 8
<211> LENGTH: 2638
<212> TYPE: DNA
<213> ORGANISM: Eucalyptus grandis

<400> SEQUENCE: 8

| | |
|---|---|
| cgaggaccaa ccgccaagaa ccatgcattt acactctctt ttactccatt cataacctcc | 60 |
| gctccccagg gcagagcaat ccaagaatac ccatctcatt cttttgcagc tgctgcattt | 120 |
| cttgatctcc ccgccacaat gcatttccga attctagccc tcctgggctt cttcttcttg | 180 |
| gccgtcctct tcccctccgc ggagccagat ctcgcgtccg accgcgccgc cctcctcgcg | 240 |
| ctgcgatccg ccgtcggcgg ccgcacccctg ctctggaacg ccaacctccc gagcccctgc | 300 |
| tcgtgggcgg cgtccagtg cgaggggaac cgggtcaccg ccctccgcct ccccggcgtc | 360 |
| gccctgtccg gccaaatccc cgacggcgtc ctgggcaact tgacccagct ccgcaccctc | 420 |
| tcgctccggt tcaacgcgct ctccggcacg ctccccctcag atctcgcgtc ctgcgccgac | 480 |
| ctgaggaacc tctacgtgca aggtaacctg ttctctggcc cgatccctgc gtcgctgttc | 540 |
| ggcttgagtg atctcgtgag gctcaatctc gcgtccaata agttctcggg ggactttccc | 600 |
| gctggtttcg gcaacttgac taggctcaag actctcttgc ttgagaacaa ccagctctct | 660 |
| gggtcgatcc cagctgacct gaagcaactc aagctcgagc agttcaatgt ttctaacaac | 720 |
| ttgttaaatg ggtcgatacc tgagggcttg ggggcttttg ctacctcttc gttttccggt | 780 |
| aactctctgt gcgggaagcc gctggcttct tgctctcaag atattgctct gcctgccggc | 840 |
| gagccttctg gtagtccagg gcagccagga ggaaagaaaa agaagctttc gggggctgtg | 900 |
| gtcgcgggca ttgtgattgg gtgcgtgttc gggttcatat tcctcgtcat actgttgatc | 960 |
| tatctgtgcc ggaagaaggg tagcaagaag tctagatctg tggacgtcgc gaccttcaag | 1020 |
| caccaggaat tggagattcc aggtgagaaa ccggtcgggg aggtcgagaa tggcggtttc | 1080 |
| agtaatgggt actccgtggc ggcagctgcg gctgcggcca tgacaggaag tggaaagggg | 1140 |
| gaagtgaatg ggagtgctgg tgccgcggca aagaagttga tcttcttcgg taattctgca | 1200 |
| agggcgtttg atttggagga cttgttgagg gcttcggcgg aagttctcgg gaaagggacc | 1260 |
| ttcggaacgg cttacaaggc ggttttggag gccgggatca cggtggccgt gaagaggcta | 1320 |
| aaggatgtca acgtggctgc aaaggaattc aaggagaaga tcgaagcagt cggggcaatg | 1380 |
| gatcaccaga gtctggttcc tctgagggca tactattaca gcaatgatga gaagcttctt | 1440 |

```
gtctatgatt atatgcctat gggaagcttg tctgcacttt tacatggaaa caaaggagca    1500
ggaaggactc cgctgaactg ggaaatcagg tctgccattg cgcttgggc  tgcccgtggc    1560 atagagtacc tacattccca aggtccaatc gtctcccatg aaatatcaa  atcctccaac    1620 atccttctca cgacatcata tgatgcgcga gtgtcagact tcggcctagc ccaccttgtg    1680
gggccttcct ccactccaaa ccacgtcgcc ggctaccgag caccagaagt caccgaccct    1740
cgtaaagttt cccaaaaggc cgatgtctat agctttgggg tgttgcttct ggagctcctg    1800
actgggaagg cacctattca ctctcaactc aacgaggaag gtgtggacct tcctaggtgg    1860
gtccagtcca ttgttcgcga gggagtggact tccgaagtct tcgatctcga gctccttagg    1920
taccagaaca tcgaggagga gatggttcag ttattgcagc tcgcgataga ttgtgccgcc    1980
caatatcctg ataagcgtcc ttcaatgtcc gaagtgagga gccaaatcga gagctatgt     2040 cattctagct cgcagaaaga tcgtgccccg cagcttgacc aggtcaatga agtgaacgat    2100
gacacgtctt ctcggtgagt tgatttccga gattggcgag cgaaattccc gaaggatcat    2160
cttgcaacat catgttcaca tttagcgtca taagctgggt tttcttgtct ttttttctgt    2220
tctatgtcca tttgggcctc tttctaatgt cattacgagg caaatagtct ctcccctttt    2280
ttcccctcat cattttctgt aattccccat tgtgctacat tttttcatct tttctttcat    2340
ttatgctttt tggggtggat atcagttact ttgttcttgt tggtaagtat gttggatcat    2400
ggtttcttgt aattattact catgcttttg cttttgcttt ccacttttgc ttttgatgca    2460
acttctcatc tgttcagact gagatgtttc agttgcttct taggatgctt ggtgtaattg    2520
tgttttcaag tgtaccgatc caccaaactt tgtttaaagt ttcctggacc ttttgaaaaa    2580
tcagattgag atgtatacct gaagtctaag tttattttgt gaaaaaaaaa aaaaaaa      2638

<210> SEQ ID NO 9
<211> LENGTH: 3239
<212> TYPE: DNA
<213> ORGANISM: Eucalyptus grandis

<400> SEQUENCE: 9
gcaacacccc ccctcctgct gaattttcaa cacatcaaca tcatattcac gttctcatta     60
tgctctgcaa gtcgtcgcgg aggaccggga caatagcagc aggaggagcc ttggaggcaa    120
gacgagttct ttgacttgtt tttctccttg gcaagggaag gtatggagga ggccttcctg    180
aggttgatct tcctggtggc ggtgcttttg tttgggaagg atctgcagct ggttttttct    240
ttcaccaatc ccgatgactc cgtggctctc caatccctca agatgtcatg gcagaacacg    300
ccgcctagct gggaaaggtc gagtgacccg tgtggactcc cttgggaagg agtaacctgc    360
aatagcaatt cgagggtaac ttcattggga ttatcaacca tgggaatcaa gggccagcta    420
attagtgaaa tagcaggact cgctgaacta agatctctgg accttttcctt caacaaagag    480 ctcactggtc cgctcgctcg gcagttgggc aatctacaga agttgaacat actgatttta    540
gccggctgta gtttcaccgg tagtattccg gacgaactgg gcaaccttgc agagctatca    600
ttcttggcgc tgaactcgaa caacctcaca ggcaatatac ctgcttcatt gggtaacctc    660
tccaagcttt actggtttga cctggctgat aatcaattaa cggggcctat tccgatatcg    720
acggacacat cccctgggtt ggacctcctg ttaaaagcaa agcactttca tttcaacaag    780
aacaagcttt cagggcccat tccggaaaag ctattcaact cggcgatggt tctaatacac    840
gtcttattcg atggaaatca gcttaatggt tctataccgt cctcagtagg acttctaccg    900
```

-continued

```
gatcttgagg ttcttcgact tgacaggaac aagttatctg gaaaggtccc tctgaatctc    960
aacaacctga caaaccttag tgaactgaac tttgcccata atgcattgac tggcccttta   1020
ccagacttga cggatatgaa ttccctcaat tacgttgacc ttagcaacaa cttctttgac   1080
ccttcggaag ctccagattg gttctcaact ttacctactc taaccacgct ggttatagaa   1140
tatggaccgc ttaaggtggt tgtcccacaa aagcttttca gctttcctca gctacagcaa   1200
gtgaaattga agaacaatga attcaatggt acgctgaaca tgggagacaa catcagtccc   1260
cagttgcagc ttgtcgatct gcagaacaac caaatatcat cggtgacgct gggctcttcg   1320
ggttactcaa atacactgat gttaataggc aaccccgttt gcactaccga actctcgaac   1380
actaattact gccagctcca gcagcagaca gtgaagcctt attcgaccag cctcgccagc   1440
tgcggaagca agtcgtgccc tcccgacgaa aggctcaacc ctcagagctg cgagtgcgca   1500
tttccatacg aagggacctt atattttaga ggtccctcct tcagggaatt gtccaatgtg   1560
accttgtttc acatgctcga aatggacttg tggacgaagt tgaatctcac tcccggttcg   1620
gttctcttc agaacccctt cttcaatctt gacgactacc ttcaagtgca gctttcactc   1680
ttcccccga gcgggaaata tttcagtcgg tcggatattc agagcatcgg tttcgacttg   1740
acaaaccaaa cttttcaagcc tcccaaacca ttcggcccct attacttcat cgcctccccc   1800
tatgcttttc cagacaatgg aggaaccgcc ataagcaaag tgtgatagt tgggatcgct   1860
attggcggca cggttctggt tcttggcctt gttgtattag ggtatatgc tattcgacaa   1920
aagaaacggg cggagaaagc tctcgagttg agcagaccct cgcatcctg ggcacccagt   1980
gggaaagata gcggaggagc gccacaactg aaaggagcac gatggttctc ctatgatgaa   2040
cttaagaggt gcaccaataa tttctccgat agcaatgaat taggcttcgg aggatacgga   2100
aaggtgtaca ggggagttct tcctgatggt catatattag caatcaaaag agctcagcag   2160
gggtcgatga aggtgcaac cgagttcaag acagaaatcg agctgctttc gcgggttcat   2220
cacaagaatc ttgttggcct cataggattc tgtttcgagc aaggagagca gatgttggtc   2280
tatgaatata tgcctaacgg gacgctcagg gatagcttga caggaaaatc aggcattttat   2340
cttgattgga agaggaggct tcgtatagct ctaggttcgg ctagaggact agcttatctg   2400
cacgaactcg cgaatcctcc aattatccac agagatgtca agtccaccaa tatcttgttg   2460
gacgaacatc tgacggccaa agtcgcggat ttcggtttgt ccaaactggt atcggacagc   2520
gggaaggggc acgtttcgac gcaagtgaaa ggcacgctgg gctatttgga tcccgaatac   2580
tacatgagtc aacagctgac agaaaagagc gatgtgtaca gcttcggggt ggtcatgctt   2640
gagctcatca ctgcaaagca accgattgag aagggcaagt atgtcgtccg cgagattcgc   2700
accgccatgg acaagaacga ccaggactac tacggcgtga gggaaatgat ggacccgtcc   2760
atgaggagca tgggctacct cgtcgggttc agcaggttct tggatttggc gatgcgatgt   2820
gtcgaggagt cggctgcgga ccgccccaca atgagcgagg tggtgaaggc gatcgagacc   2880
atgttgcaga acgatgggat acaccaccaac tcgacgtccg catcgtcgtc ggcgacggac   2940
tttgggtcga cgaagggcgc tcctcggcat ccgtacaacg atgccttacc caagaaggaa   3000
gttagctata gcgattcctt tgattatagt ggtggatatg gactatctac aaaaattgaa   3060
cccaagtgaa aaacatgatc aattgatctg ctcagtcact tgttttttctt tttcctttgt   3120
ttctgctcag gtttgcttg gtcctcttca caatttctgc aagtgagtaa cctgtcttac   3180
atgtgtaata gttttgatca gccgcatcaa gtgaaggaag ttcttgtgca aaaaaaaaa    3239
```

-continued

<210> SEQ ID NO 10
<211> LENGTH: 2336
<212> TYPE: DNA
<213> ORGANISM: Pinus radiata

<400> SEQUENCE: 10

| | | | | | |
|---|---|---|---|---|---|
| attcgattcg | cgatgctatt | tccatggcgc | agcctcgttc | tgatagcctt | cacctccctc | 60 |
| gtcgtacaac | ttattcctgc | gcaggccgtg | gaggatcgtc | gacatgacac | cactttcctg | 120 |
| ttcgacggat | tcaatggaac | caacttgatc | ttggaggcta | atgcttcagt | catcggctct | 180 |
| gaatccgtac | tctcccttac | aaatcactcg | catgagttca | tgctcgggcg | cgcgctgtat | 240 |
| gcagctcctg | tgcaaatgaa | aaacaaccat | acggtttcct | ccttcagcac | taccttcgtt | 300 |
| ttctccattg | tgcctcctcc | ctctaacgaa | ggggacacg | gattagcctt | catcatgacg | 360 |
| ccttacacat | ctccgatggg | cgctcagccg | gtccagtatt | tgggcttgct | taacctcacc | 420 |
| agtaacgggc | agccatacaa | tcatttattc | gcagtggagt | tgataccat | catgaatgta | 480 |
| gaattcaaag | atccagaccg | caaccacgtg | ggcgtggata | tcaacagtct | catctcagtc | 540 |
| cagacagaga | ccgccggcta | ttggaatggt | gaggaattcc | atgaactcaa | cctcaggagt | 600 |
| ggacggaaca | tacaggcctg | gatcgattac | gatcatcttg | agagcagtct | caatgttacc | 660 |
| attacggtgg | ccggggttgcc | gagaccgcag | aggccgttga | tatctctgca | aatcgatctg | 720 |
| cagaatattg | tagaagagaa | gatgttggtg | ggcttttcag | cggcaacggg | gctgttagtg | 780 |
| gaagaccatt | acattctcgc | gtggagcttc | accaccgaag | acacggcgcc | gcctctcgat | 840 |
| gtttcttgcc | tctcttcatt | tgccaacatg | tattccgaac | ctctgagccg | ggattcata | 900 |
| gccggtgtca | ccgtggtttc | tgtggttctt | tctggctgg | tgattgcggc | ggccatgttt | 960 |
| ctgagaagaa | cactaaacag | ggaaacggtc | gaagaatggg | agcaggagta | ctggccccat | 1020 |
| agattcgatt | acaaggagct | gcgtatcgcc | acgcgagggt | ttcgggacga | aaaccttttg | 1080 |
| gggtacgggg | gatttggcat | ggtttacaag | ggttttctcc | ccaggagcgg | ccaagaagtc | 1140 |
| gcagtgaaat | gtataacgac | ggagttcaag | gaaggaataa | aggggtttgt | tgcagagatc | 1200 |
| tcaagcatgg | ggcggctaca | gcaccggaac | ctggttcaac | tccgaggatg | gtgccgaagg | 1260 |
| catacacagc | tattcatcgt | ttacgactac | atgcccaacg | gaagcctgca | taaactcatc | 1320 |
| ttcggtagtc | cgacaacagt | cctgccgtgg | catcggcgat | acgcgatcct | aaagggcgta | 1380 |
| gcagcggggc | tgctgtatct | gcacgagcaa | tgggagaaga | gggtcgtcca | cagggacatt | 1440 |
| aagtcgagca | acgtgctgtt | ggattcggag | ttcaacgggc | ggcttagtga | cttcgggctc | 1500 |
| gctcggctgt | atgatcacag | tgagaatccg | gagacgacat | atgtggtagg | aacgttgggg | 1560 |
| tacatagcac | cggagttgat | acaaacgggg | aaggcaactc | ctagctcgga | cgtgttcagc | 1620 |
| ttcggtgttc | tgctgttgga | ggtggcttgc | gggaagagtc | cagtggattc | gttggaggac | 1680 |
| tctgagcgca | tgattttagt | ggagtgggcg | tgggagctct | acacgagggg | gaggttgctg | 1740 |
| gaggcgtcgg | atccgaagct | ggccgcaaag | ggtggatatg | atgaaggcga | gatggagaag | 1800 |
| gtgttgaaat | tggggttact | gtgttctcat | ccagagccgg | agagcaggtt | gagcatgcgc | 1860 |
| caggtttgcc | aagtactgaa | cggcgaagct | ccagttcctt | gtagatggta | gggacggggc | 1920 |
| aattccggag | gtcaggatta | tccatgtttg | attaaagaat | ataatacttt | tatttattat | 1980 |
| atattatttt | atgttcccat | gcgggcccag | cgaggacact | gctattgttg | ctggtcagtg | 2040 |
| gttcaaatcc | gggaaagaga | gcatgccgtt | actcaagtta | ttgctagcta | tgcggggat | 2100 |
| ttaagtagta | gtctactgtt | acaaaacata | gatctgccct | atctacttcc | tgtgacaaag | 2160 |

-continued

| | |
|---|---|
| cagagttgaa tgctcagaga gcaggaattt gaaatccaaa ttcctttgta ttaaacattt | 2220 |
| tagttaattt tatgatgcgt aggcttcatt tgtcaccgta ttcgattcgt aaagggcgac | 2280 |
| actaacaata attttataat atttgtaaaa tttttggtgt taaaaaaaaa aaaaaa | 2336 |

<210> SEQ ID NO 11
<211> LENGTH: 3097
<212> TYPE: DNA
<213> ORGANISM: Eucalyptus grandis

<400> SEQUENCE: 11

| | |
|---|---|
| tttgttctct tgcaatgcca tatatacacc tgaaattctg atcgctctca ctcatctgtc | 60 |
| gcattcaaag cctcaaagcc gcttgtttct tgaactttgc cttggcttca agaagaaag | 120 |
| tcctcaaata gaagatcgac catatgggac tgaagatatt ctcagtcggc tttgctcttc | 180 |
| tttgttgctt ctgttcactt ggcttctgtg atcaagacgg ttttctgagt ttagcttgtg | 240 |
| gtggaactac caattacacg gattcatcca acatctggtg gattaccgac agtgatttca | 300 |
| taagcacagg aaagactacc tatgttgaca atatcgaggg caattcatct ggtgtttcgc | 360 |
| ttcggttctt cccagattcc aaagtccata actgttacag attgcctgtg aggaatatat | 420 |
| cctccttaat tctcgtaaga agccaatttg tgtacaagaa ctacgatgga cgagggaagc | 480 |
| caccggcatt ttctgtttct cttgggacag caatggctag tactattaac ctgaccacta | 540 |
| atgatccttg gactgaagaa ttcatatggc cggtcgacaa ggacacactc tcttttttgct | 600 |
| tgcatcgtat tcggaacggt gggactccag taatttcttt gctcgaagtg cggcctcttc | 660 |
| ctcctgaagc ttacaaaagt ggaatggggg attacccgaa taagttactc aggaagtctt | 720 |
| atcgaattga tagcggttac accaatggct cgttgaagta ccctgcagat ccctatgatc | 780 |
| gaatatggga tgctgataag agcttcacac cattccatgt gactactggg ttcaaaattc | 840 |
| aagtcgagtt taatctctcg gggctctcgg agagtcctcc tcccgctgtt cttcaaactg | 900 |
| ccagagtttt ggcacgaaaa gaagtcctga cgtataactt ccctctcgac tcacttggcg | 960 |
| actattacgt cgtcctctat ttcgctggga tccttcctat ttccccatct tttgatgtga | 1020 |
| taattaacgg ggacatagtg caatctaact atacagtgaa aacctcagca gccagtgctc | 1080 |
| tatatgttac gaggaagaaa attaagtcgc tgaacgtgac gttgaagagc aaacgtttct | 1140 |
| ttcctcaggt taatgcaatt gaggtgtatg aacttgttga cattcccca gaagcttcat | 1200 |
| caaccacagt ttcagcactt caggttatcg agcagtttac tggcctggac ctgggatggg | 1260 |
| aagatgatcc ttgctcacca aaaccgtggg atcatgtcgg atgtgaagga agcctagtaa | 1320 |
| catcactgga tctttcagac atcaatctga ggtctatcag tccaacatttt ggggacttgt | 1380 |
| tggatctcaa aacactggat ttgcataacg cgtcacttgc tggtgagata cagaacttgg | 1440 |
| acagcctgca aaatctcgag aaattgaacc tgagtttcaa taaactgaca tcgtttggct | 1500 |
| ctgattggga gaacttgatt agcctgcaag ttctggacgt ccaaacaac agcttagacg | 1560 |
| gagttgttcc cgacggcttg ggagagctga agaccttca cctactggac ttggagaata | 1620 |
| acctgctaca aggtacctta ccagattcct tgaacagaca gagcttggag gtcagaacct | 1680 |
| caggaaactt gtgtctttcc ttctccacaa ccgcgtgcgg tgatgcatca tctagtcctt | 1740 |
| caattgaggc accgcaagtt acaatagttc ccgagagaaa caaggggga cataatcgtt | 1800 |
| tagccattat actcggagca gtcggaggag tatcactagc tattttactc atcccgctct | 1860 |
| tcgtattcat gtacagaagg agaggaagaa ctgaaatgtc atatacggaa agggcagtcg | 1920 |
| cagacgtgag aaactggaat gcagctaaga ttttttccta caaagagatc aaaacagcta | 1980 |

```
caaacaactt taaagaagtc attggtcatg gaagttttgg atccgtgtac ctgggaaacc    2040
ttccagttgg aaaactagtt gctgtgaaag tgcggtttga taaaacccaa cttggtgcag    2100
attctttcat aaatgaggtt cgtctcttat cacaagtccg ccatcagaac cttgtcagtc    2160
tggaaggatt ttgttatgag tcgcagcgtc agattttagt ctatgaatat ctaccgggtg    2220
gatcactggc tgatcaactg tatggtccaa acagtaggaa attctcacta agctgggttc    2280
gtagactcaa gattgctgtt gatgctgcaa aaggactgga ctatctacat aatgaaagca    2340
atcctcgaat catacaccga gacatcaagt gcagtaatat actattggac aaggagatga    2400
atgcaagact ttgcgacttt gggctctcta agcaaatgat ccagccagac gcaactcacg    2460
tgaccactgt cgtcaagggc acagctggtt acctcgaccc tgaatattac tccacccaac    2520
aacttacaga gaaaagcgac gtctatagct ttggagttgt gcttttggag ctcatctgtg    2580
gacgagagcc gttaaatcat tcaggaactc cagattcctt caatttggtt ttatgggcaa    2640
agccctactt gcaggcaggt gcatttgaga tagtggatga gagtttaggg ggaagtttcg    2700
atgtggaaag catgaggaaa gtggcaaaaa tcgctgtgag gtctgtagag agggatgcat    2760
cactaaggcc aaccattgca cagatactgt ctgtgctcaa agaggcttac agcattcagc    2820
tctcttatct tgcagcctct ggacatgtga actgaatcta ctcgtattac aaccaagaca    2880 agatttttt ctttcggcc caaagagata aaaagaggtc gtttgtcctg ataacaaggc    2940
tgtttatcat tcgtttgagt ggaacctatg tacagagaga gttttgggtg caattatcat    3000
atttatcgta cttaaatgta tgatactgtt ttatttcata ttcatttgtg caagagaaat    3060
taagcaagtt tttgttccta aaaaaaaaaa aaaaaaa                             3097

<210> SEQ ID NO 12
<211> LENGTH: 2649
<212> TYPE: DNA
<213> ORGANISM: Pinus radiata

<400> SEQUENCE: 12
gttggaagac cctgtaagca tttggcttcc atattgctat ttggcaaaga gagaaacatg      60
ggttgtcgga aagctgtgag atctgtgagc ccacagaacc catcttcctc tctgatgcat     120
ctcagactgt taggtgtttt gctcatgctt cattgcattg atgggctgat cctaaatcct     180
gaagtttcta ctcttctcac actgaaacca acgttgtctg aacaggggt taacgttgta     240 ctggcctcgt ggagtgcctc tcgccctctg tgtggatgga aaggagttat gtggatgtac     300
aatggtatac ctgtcaactg ttctgttccc aaatttaggc acagtgtggc tttggcttac     360
agtcgcaagg tctcagtgct ggggattgat ttggaagcaa caggttgaa gggtacagtc     420 ccaaaggagt tgggctcctt tatatatctg cagcagctga atctgaataa caatagtctt     480
acaggaggga tgcctccaga gttgggaaat gtgcctaatt tgagcagtct gcaactcaag     540
aacaatgggc tgaatggagg cattcctact gctatttgga atctgtgcga taacattact     600
gagctggaat tgggattcaa tgagctatca gggagcatcc ctgaacccgg aaatgggtct     660
aatataggtt gcccacaact ccggagattt gaggtgaata caacagtct aacaggtaca     720 atccctagct tccttgctaa ttgtatttct cttcaagagc ttgatttgag tgggaattct     780
ttcaccggcg aaatacccaa tgagcttgca aatctgccaa acctgacaac tctcaacctt     840
gcccacaaca atctaagtgg tcgtataccg agttttcggc agaaatttga taagaattcc     900
tttgtagaaa atagtggatc cctgtgtggg cagcctctgt taaacccatg tggcgtagct     960
```

-continued

```
ccaaatgctg ctagtgctgc ttctgcaaat gtgactgcag cccagttcaa tgtgaccaaa      1020
gcccatttca aatctatgag cactggagct attgctggaa tcatcattgg atcaattgct      1080
gttgtagtca ttgccagttc tttgttaatt ggatgctacc ataggttcag cacagatgcc      1140
actgacaagt cttcgtcttc gtctgcccct tcgaagaaag ataaggaaga agacatggac      1200
aatgtgagtg ggaaattaat aaacttccaa ggaggtgagc atttgaccgt ggatgatgtt      1260
ctgaatgcaa cgggagaagt cttgggcaaa tccagttatg aactgtcta  caaggccagg      1320 ttaagtagtg gttgtatgat cgcactccgt cttctccgag atgggtgtct cagaagcaca      1380
gacgaattca tgcctgccat tcaggagttg ggtaccatca ggcataagca tcttgtttct      1440
ctaagagcat tttattcagg acaagaggc  gagaaactgc ttgcctatga ttaccttccc      1500
agaggaagcc tcgcagaatt gctacacagt acaaacaggc ctgctcctgg atgggctaga      1560
agacataaaa ttgctctggg agctgctaga ggtcttgcct accttcacac tggattccac      1620
aaatccatca tacacggcaa tatcaagtca aaaaacatac ttgtggatga caattatgtt      1680
gctcatcttt ctgactatgg tcttaacaag ctaatgaact caacagcaaa tattgagatg      1740
ttagaagctg ctgcttccca gggatacaaa gcacctgaac ttatcaagat gaaaagggcc      1800
aatgcaaaga ctgatatata cagctttggt attggtttac ttgaaattct cacaggcaga      1860
agacctggta gaacaagctc atccaatcat attgttgatt gccaacagt  cgtgaagaat      1920 gcagtgcttg aagagaggat ttcagaactc tttgaccttg agcttttgcg tgcaatgaga      1980
agtccagcag atgaaggtct tctgcaagtt ctgcagcttg caatggggttg ttgtgctcct      2040 tctccatcag tcaggccaca tataaaagag gtagtccgtc aacttgagga gattaggcca      2100
aaacctcaat ctccgcatct tgcccttttcc ccacaataca attcagatga caagagtagt      2160
agggagtttt tgttggatgg cggacaaaat taaagatgga atttactcgt ctttcctccc      2220
tagttccgac acttatttag gttctacata tgctataaac tactaccgta gttacagata      2280
cgggaacata ttaagggatc tatttttctt ttcttgcaag atatgtctca gattataatt      2340
tatgcccatt gggaggggct ttcttttgtc agatcatttg gtgttctgag aggctgtaag      2400
agaaacatca atttagtccc ctgcttctgt acgatttcct atttgtaaat catactgata      2460
gttgtgagga ctctcagttt ctgtttgtgt ttttcatacc agagtagatt tcctttttgtt      2520 gtcaaagtca tgacatagta aaaatcatga caaaaattga catgtagacg tgtaaactta      2580
gtggtaaaga tatgcttata tgtatatgaa ggatatgcac ttgcgtttaa aaaaaaaaa       2640 aaaaaaaa                                                               2649
```

<210> SEQ ID NO 13
<211> LENGTH: 2513
<212> TYPE: DNA
<213> ORGANISM: Pinus radiata

<400> SEQUENCE: 13

```
gaaatgaaga tttgagttct ccggaaacac actaaggata tcgtagctct ttgaaaatgg       60
gaaagaaaat tttgcaatgt ttgcggttaa ttattgctat attgacggcg tctattgcga      120
tatcgcacgg aactacggat ccagacgacg tttctgcgct caaaggcata tatagcagtc      180
taaattctcc ccagcaactt tctggatgga gtgcaaatgg aggagatcca tgtggtcagt      240
cctggaaagg ggtttcatgt tctggatcat cagttacatt aatcaagctc tcaggcttag      300
gattgtcagg atcattatat taccagcttt cagacctttc atcattgaca accttggatt      360
tgagcaacaa caacattcag ggcaacattc cttatgcact tccacagaaa ctccaggagt      420
```

```
taaaccttgc tagcaatggc ctcagtggta ctataccgta ttcaatttcg aacatgactg    480
gcctcacaga tttgaagttg agtcacaatc aactttcagg tcagatccaa gatatatttg    540
gacagctttc cagcctctct actctggatc tatccttcaa tactttgact caaaatctgc    600
cccagagttt cagctcattg tcgagtctca gtgtgctata tttgcaaaat aatcagcttg    660
ctggttctgt taatgttctt gccaatctgc cactcacaga tttgaatatt gaaataacc    720 gttttagtgg ttgggtaccc aatgcctgga ggtccaacca aaactttaaa tatagcagtg    780
gtaatagttt cgccactggt cctgctcctc ctcccccacc atatactcca cctccacctt    840
ctaacaatcg gccacccaag tcctcaaatg tggtcccttc atcaggtggc tcaaagggtg    900
ggaacagcaa taagaaatct ctgagtggtg gtgccatagt gggtataata tttgcagtta    960
ttttgactgt tgttgctgct atattaggag ttattttata tgcacgtaag tctcctagaa   1020
gagagcagga tgaagaaaaa ctaagcaatc gtgtgtcttt caccccccta tctcccctcg   1080
atgctgaatt attgaaagag agtccagagc aaaaagtcag ctcatcacct cttgaaatcg   1140
ctcttaagcc tccccttct gaacgcaaca agtctacagg ggacaaaggc ttcggaagta   1200
ttttttcaag taagaggact aaaaacccaa tatcagcaac tgaatattct attgcagacc   1260
tgcaaatggc aacaaatagt tttagtcaag ataatcttat tgcggagggt gctcttggac   1320
gaatctaccg agcagagttt ccagatggaa agattttggc agtgaaaaaa ttggacactt   1380
ctacgctgtc cctacaaagg cctgaagact tcctggacgc agtatctaat atatcgcgcc   1440
tacatcatcc taacattaca gaactagtgg gttattgcac agaacatgag caataccttc   1500
ttgtgtatga atatttcgac aatggatcac tctatgacgt attgcacatg gcagatgaga   1560
ctactagaaa tttgtcttgg aacattcgtg taaagattgc gctgggttca gctcgagttt   1620
tagagtattt gcatgaagtt tgctctccat ctattgtgca taaaaaattc aagtcgtcta   1680
atattttgct tgatgatgat ttcaaccctc gtctgtccga ctgtggaatt gcggccctca   1740
atccaaattc tgagcgtcag gttcaggtgc tgggttcatt tgggtacagt gctcctgaat   1800
atgtcatgtc aggaatctat acaatgaaga gcgatgtgta tagttttgga gtggtaatgc   1860
ttgagctttt gacaggccgg aagcccttgg atagttcaag aacaaggtca gaacagtcat   1920
tagtaagatg ggccacccct cagcttcatg atattgatgc attggcaaag atggttgatc   1980
cagctttgaa gggaagttat cctgcaaaat ctctctcgcg ctttgctgat attattgccc   2040
tctgcattca gcctgaacca gaattccgtc ctccaatgtc tgaagtggtg caagcattgg   2100
ttcgtatgat gcaacgggct agcctcaata gaggatgac aggagatgaa actgcagacc   2160
acgatcctgc agattattaa atgcagtgat attgctttgg tggtactcca gaagaaaata   2220
tttaattcta aaaagctcgt accgccttct ttggactttc caaaacagtt gaagagttga   2280
taacttcatt atttagctcc taaggccttc gttggacttc cacaacagtt gaaagagttg   2340
ttagcatcat ccttcgttgg acttccacaa cagttgaaag agttgatagc atcattattt   2400
tcataaattg aatctgttca agatttttt tagtccacgt tgtggtgaaa acaatgtaat   2460
tggaatatta ataaaatatt aatactggtt tgctcaaaaa aaaaaaaaaa aaa          2513
```

<210> SEQ ID NO 14
<211> LENGTH: 374
<212> TYPE: DNA
<213> ORGANISM: Pinus radiata

<400> SEQUENCE: 14

-continued

```
gttaggggtt taaaacctga ggaggctgct gtgtagggtc gagtttgagc ttgctggcgg      60
acgggagggg gcgaggctca taacacaatg cgacacaatg cgggttggat gtctgtcaag     120
ggttttaaag cctgaggagg ctgctgcgta gggttgagtt cgagcttact cgaggacccg     180 aggggcgaa gctgatgatg aggcttggag tgtgaatccg tggatgtttt agcgggacga     240
aggatcgagt ctcgtccgtg aggggaaatc aggcagttga aacaaagagg tgaagaaatt     300
tgcagcagag tcatgcagca gccgtatgta gtactggccc tgtggtggat attggtactg     360
cgtcacccgc tctg                                                       374
```

<210> SEQ ID NO 15
<211> LENGTH: 490
<212> TYPE: DNA
<213> ORGANISM: Eucalyptus grandis

<400> SEQUENCE: 15

```
gtctaaagaa gcttgaggga tagacaagcc aaagtaagag agatagagag aaccagttga      60
tccaataaag gtcagatttt tatgctttgc tcacacacac ccatctgaag ctactttgtg     120
tcatgtcatt cccctatcct tctcctcaaa cccagcaaca tacaattgct ttgtctaaac     180
actagtggtc tatgtctgaa agcaacattt tctttgagaa tcaatgaggg tcctattcat     240
tgttctgggg gttgtacttc tgtgcactgt aattcctggt tcatcttctt ctgtcagtga     300
tgttgatgtc ctacttgcgc tgaagcaagg attccagtcc cctgaaccgg ctttaatcac     360
ttggagttct tcaaactcga gctcagtttg cttatgtgat gggattagat gctcaagggg     420
acgcgtggtt tcgctccagc tgacggattt gaatctgggc ggctctgtct cccctcctgt     480
ttcaaggctc                                                            490
```

<210> SEQ ID NO 16
<211> LENGTH: 468
<212> TYPE: DNA
<213> ORGANISM: Pinus radiata

<400> SEQUENCE: 16

```
gtttttctca tgctgctgtg ctttgtgctc gttgcaggga cctctgctgc tgtagacgat      60
catcaatatc tgtatcatcc ttctcattat gttatgaatg agcgccagga atctggaagc     120
tccatggccc gccacgagaa aagggatgtg gaagctcttc tctccttcag aaacgccata     180
acggccgacc cacatggatt gttgtccaac tggacggccc acaactctgc caacatatgc     240
tcgtggaatg ggatcggctg cagaaaacag agcagaagag ttgtttccat ataccttcgt     300
ttctcacacc tagaagggac gctttcgcct tctgtgggta atatctcttt actgcacacc     360
ttcgtactta ctgtcaataa attgacaggg agaattccgc cagagtttgg gcaacttaaa     420
gccctccaaa cgcttgactt gtaccgtaat cttttatcaa gttctggt                  468
```

<210> SEQ ID NO 17
<211> LENGTH: 518
<212> TYPE: DNA
<213> ORGANISM: Pinus radiata

<400> SEQUENCE: 17

```
atagagtgag aaatacagag cctaatctga aggaagttgg agtgatagag tgagaaatgg      60
atcttcttct tctcctgctt gtgatgatgg gtgtagcaat gcctactcat tctcaacaca     120
cgggtggatt cacttctgtt caacgttttc cttttaatga acggagtatg atggggaaac     180
cctccatagc cgggtatcat gaaaaaggg atgtggaggc acttctcagc ttccggaagg     240
```

```
gcatcacatt ggatccatat ggatggctct ccaactggac ggccaataac tcacataacg      300
tctgcctgtg aacggaatt tcgtgcagcc caaacacgaa tcgagtggtt gaaatttctc       360
tccgttacgg ccggttgaat ggtacgctct ccccgtatat tgggaacctc tctcttttgc      420
ggcatttaga tctttcttcg aatgctttga gtgggagaat ccagcaaaa tttgggcagc       480 tgaaagcgct acgaatactt gacctctcca ataatgct                              518
```

<210> SEQ ID NO 18
<211> LENGTH: 630
<212> TYPE: DNA
<213> ORGANISM: Eucalyptus grandis

<400> SEQUENCE: 18

```
tgggtctctc tctctctctt tctctgtgtg tctcggtcct tgtgctcgcg ggctgtttcg      60 ctttacccte ctctacttca ccgccaatga cttgcggaga gatcattctg ggtctgtgcc      120
tgtgacgtcc cttcttggga ttttcgtgct tcattcttct ggtacactcc tcgtttgtaa      180
aatcccggtt ggcgagctgg gtggagtgtt ctttgcgtt ttgtggtctt ttaggctctt       240
gggtcgtcgt tgttttggcc attgaggccg tttcttgtcc gtttcctggg agagtgaggt     300
gcgcagacga gaacggaagg aaaaaggtgg gaactttgaa gcgtggactg tacggagcgt      360
cgtgggctct gcgaaattga agatggtttt ccgacgattc gtggtgatgc tcttcatttg      420
cacggcgtcg gtctgcgctg gcctcactga tcctcgcgat gtggcggcaa tcaatagctt      480
gtatgtttca ctgggctatc cgcctctacg tgggtggtta cttgttggag gcgatccctg      540
tgttgacaat tgggaaggtg tcgagtgtgt tatctcaaac ataacgggac taaatctgag      600
cggagccaat ttgggtggag aattgggcga                                       630
```

<210> SEQ ID NO 19
<211> LENGTH: 385
<212> TYPE: DNA
<213> ORGANISM: Eucalyptus grandis

<400> SEQUENCE: 19

```
ggcagaaatc ctaagctagg cagagtctcc gacgatacca aacgattat agttcctgct       60 tctcttgttt cgtgatgggt ttcttctacc aagtctttct catatttctg gcggtcgcgc      120
cgtctgctct gtgccaagtt actgagttcg tcagcataga ctgcggagga tccagcaact      180
acacagaccc gacaacaggg ctcgcatgga tcccggacac gggtctcatg agctatggcc      240
agtcttcgaa ggtgcagaat cccaacgtaa gctcggtgca gtattcgacg cgcagggact      300
tcccaataga cggccagaag tactgttaca ccctccggac cgaagagaga aggagataca      360
tcgtccgtac gacgttcttg tacgg                                            385
```

<210> SEQ ID NO 20
<211> LENGTH: 496
<212> TYPE: DNA
<213> ORGANISM: Pinus radiata

<400> SEQUENCE: 20

```
ctctcctcgt ctctgcattt caagcaccat ggcgtttcca tgttttatt ttcctttccg       60 tatcttgttt ttcctcttcg tatgctcttt ttccttctcc ttctccttct ctgcgcacaa      120
atttcatgac ggtcggaaat ggctcttgtc attcaagatc gatattacca atgatcctca      180
tgcttccatg gccaactgga gtcctgcagt ccacctgtgc aactggactg ccgttacgtg      240
```

```
cagtcgcagg cacgcagata gggtggtctc tctcgaccta agtggcatgg atctgagcgg    300
ctccatatct ccttccctcg gcaatttgtc atttcttcat acccttaatc tcagtgccaa    360
tgctctccat ggtcatattc caccacaact gggacgcctc tttcgtttga gaaacctctg    420
gttacgcaac aattttctgc aaggaaatat ccctacagag ttcgcctccc tcaaacattt    480
gcaacagctt tacttg                                                    496

<210> SEQ ID NO 21
<211> LENGTH: 352
<212> TYPE: DNA
<213> ORGANISM: Eucalyptus grandis

<400> SEQUENCE: 21
gagaactgaa ctgacccaga gacccacttt ttctctcatc atcatcccctt caggatcatg    60 agattttcgt ctctcaaaag aagaaggtgg atcatgagga cagcaatcat cattaccagt    120
ctgatgtgtt gttcttccgc tagagacagc atgacgctca gcagcccgct cagcgatgag    180
cacggagaca ctctggtttc tgatggaggg accttccaac ttggcttctt cagccccaac    240
ggaagctcgg gctctgacca cagaaggtac cttggaatat ggtactacga ctccgacccg    300
cagaccgtag tttgggtagc taacagagac caccctgtgt tggatgtgac tg            352

<210> SEQ ID NO 22
<211> LENGTH: 635
<212> TYPE: DNA
<213> ORGANISM: Eucalyptus grandis

<400> SEQUENCE: 22
ccggtctgaa aaccgacact tttgagtgag aaccggttcc ttttgcggag ttttggaggg    60
acgggaagtg taatgggggct cgcacgtttg ctcctggttg gcttcgtcct gctcgtgctt    120
ggctcgagag cgctcgtgtg cgggaatgcg gagctggagg cgctcatgga gatcaaggcc    180
tccttggacc cggagaacaa ggtcctcact tcgtggacca gcaatggcga cccctgcggc    240
ggctcgtttg acggggtggc gtgcaacgag catcagaaag tggcgaacat ctcgctgcaa    300
gggaagggcc tgtcggggaa ggtccctccc gcagtggctc agctgaagtg cttatcgggc    360
ttgtacctgc actacaatta cttgaccgga gagattccaa gagaaatctc tagtctgacc    420
gagctgacag atctctacct cgacgtgaat aatttaactg ggagtatacc ttctgaaatt    480
ggaagcatgc ctagccttca aggtgagttt tgtttgttgc tccaagggca ggggtgaatg    540
ctttcttgtg tatgatttca ctcccaaggg taccttatcg caatatcttg atttagaaga    600
tggaagcatc caggttcttg attggtccac aaggg                               635

<210> SEQ ID NO 23
<211> LENGTH: 580
<212> TYPE: DNA
<213> ORGANISM: Eucalyptus grandis

<400> SEQUENCE: 23
cccaggagac atcacccatt ttcctaagta ttaccagatc aagagaataa cctgaagctg    60
tgttctttgc tactccgcat ccgttatttt cttcggactc tgctccgatg ggagtgaaga    120
gagcgaattc ctctctgtgc tgcgtggttt tgctcggctt gtgggcttgc gtacatgggt    180
tgctctctcc tagtggtgtc aatattgaag ttctagcttt gatggacata aggaatttgc    240
tagtggatcc tcatcaagtt ctgaacaatt gggacgcaaa cgaggttact ccttgtacct    300
ggactgcgat cacgtgtgag gctgatgtcg tcactaatct agaaattcca agacagaact    360
```

```
tatctggaac gctttcgcat agcattggga acttgattaa tcttaaatat ttgttccttc    420
aggacaacaa catttcagga tttattcctc ccgagcttgg gaagctccag aaacttgaaa    480
tgctcgacat ttccagtaac tcattctctg gtgaaattcc taccgagcta tcccatctca    540
agaacctcca acaactgaga atgaactaca ataacctttc                          580
```

<210> SEQ ID NO 24
<211> LENGTH: 457
<212> TYPE: DNA
<213> ORGANISM: Eucalyptus grandis

<400> SEQUENCE: 24

```
ctcacctccc aaagaccaaa catccccaaa aatcatggtt tcttccttat tgctgtccag     60
ccagcctaat ttagtggtcg gcttcctctt cttgctcctc ttagttgaca ccactccatt    120
tcacggagca ggcgatatgg cttcctccac ttccttttc accatcaaca tgaccaagag     180
taaggatgaa gtagaggctc tcttgaattg gaaatctact cttgacaact atagccagtg    240
tctcctctct tcatggcatg acaacaatcc ttgcggcttt agcggtgtca cttgtgacga    300
ctccaaagct gtcaacaatc taaatctttc caatcttggt ttgagaggaa ctctagacgg    360
tcttgacttc tcgtgcttaa ccaatttggt tacctttgat cttccctaca acgcaatcta    420
tggctccatc ccctcaagta ttggtaaccct ttccaaa                            457
```

<210> SEQ ID NO 25
<211> LENGTH: 481
<212> TYPE: DNA
<213> ORGANISM: Eucalyptus grandis

<400> SEQUENCE: 25

```
ggaagagtgt aacttcttct tcttctccat ttgaattgtt tggcgctgtt tacagatgaa     60
gattggagtg acgagacaca tctttttgct gaggaaggag tgtgaaggtg cttcaatctt    120
ccccagaagc cggggaggct agaagagctg ctcgttcttc ttcgagccta actattctcc    180
aagtatattg ctgtgaactg gctgtagaaa atggaaggga agcacctcgt ttttctgaca    240
attctcttgt tggaatcgat ttgctcgaat gtctcggcga tacccaacga ggataagcaa    300
gcattactgg atttcttgg caatgtttcc ctctcgcgcc ctctcaattg gaacaaggat    360
tcttctgtgt gccggtcctg gacagggggtc aagtgtaata acgaccaatc gagggttgtc    420
gccctccagt tgcccggagt ggggatcaaa ggtcgaatac cgccgaacac actgagtcgc    480
t                                                                    481
```

<210> SEQ ID NO 26
<211> LENGTH: 648
<212> TYPE: DNA
<213> ORGANISM: Pinus radiata

<400> SEQUENCE: 26

```
tgattccatt gcgctgaaac caagaactct gtctgtctga tcaggctgta tcatggccta     60
caagcttttg agattttggc ttgaatttca ggccttacta gtcctctttc cattggctct    120
gagtgtctct caggagggct tggttttgct ggaagtgaag aaagaactga gtgaccccaa    180
tggatttctt ggtaactgga aggcagagga cgattctccc tgcaaatgga ggggtatctc    240
atgcgaccag aggtcaaaat cggtggtggg gattgaccta agcagcggag gtttagttgg    300 ggttttttcct agtgtcgttt gcaatcttcc acagctgaaa aatctgtcgt tgggggataa    360
```

```
caatattggc tcaatattac ctcgcaacct ttccatgtgc aggcagcttc agcgcttgaa    420
tttatcgcag aatcttttg tggggaacct tccggacttt atttcagagc tcgcagagct    480
ggaatacttg gatctctcga gtaacaattt ctctggttcg attcctgcag gcattgggaa    540
actgccaagg cttcaagtac tgaacctgtg ctgcaatctg ctaaacgaga caatcccaac    600
atttctggga aatctcagca atctgcagca attattgctg gcatacaa               648

<210> SEQ ID NO 27
<211> LENGTH: 427
<212> TYPE: DNA
<213> ORGANISM: Pinus radiata

<400> SEQUENCE: 27
atacattagt tctgcaaatc aagaatggga tcgtcggcct ccccttttat ggtgttgtta    60 ctccttttcca ctttgattct tgaaatattg ccaatgtatg ttgcaacaaa tagaagcgaa    120
gctgatctcc aaggtctcat agcattcaag gcatcaatca ccagtgaccc cttgaatgct    180
ttagctgatt ggactgcttc tgctcatcac tgtaattggt ccggtgtggc ctgcgatccc    240
ctccacaacg ttatctccat tagcttacca gagacacaaa tccaaggcct catctctccg    300
tttcttgcaa atatatctta tttggcttca ctagacctca ggtccaactt cttccatggt    360
gtcattcctc cgcagctcgc tctgtgctcc caacttatcg atctggagct ctttaacaat    420
tctttga                                                             427

<210> SEQ ID NO 28
<211> LENGTH: 516
<212> TYPE: DNA
<213> ORGANISM: Pinus radiata

<400> SEQUENCE: 28
gctgaacata actgttttgc ccattctgat tttgctgaag caccaaggct tcataagagc    60
aaaatggaag tacggatgat aaccataatg atattatgtg ctgctttact atgtgaaggg    120
agcggagagg tggatgttct gatggagatg aaagctgcat ggacccccaa ggggagata     180 ctctactctt gggtgaaggg aggagatccc tgcagtggga cttttgatgg agtggcctgc    240
aatgagcaag gaaaagtggc taatgtttct ctgcaaggga aaggattatc aggctcaata    300
ccctcaacca ttggcaagct caagtgtctc actggacttt atttgcatta caacagcctt    360
ggaggggaga tacccagaga gctttctaac ttaactgagc tgctggacct ttatcttaat    420
gtcaatgggc tctctggtcc cattcctaag gagctgggag ccatgtccag cttgcaagca    480
ctccagctgt gctgcaacaa gttgacaggg cctata                              516

<210> SEQ ID NO 29
<211> LENGTH: 418
<212> TYPE: DNA
<213> ORGANISM: Pinus radiata

<400> SEQUENCE: 29
ggaagttgga gtggtagagt gagaaactga cagcctaatc tgaaggaagt tggagtgata    60
gagtgagaaa tggatcttct tcttctcctg cttgtgatga tgggtgtagc aatgcctact    120
cattctcaac agacgggtgg attcacttct gttcaacgtt ttcctttaa tggacggagt    180 atgatgggga aaccctctct gttcccatcc tccatagccg ggtatcatga aaaagggat    240 gtggaggcac ttctgagctt ccggaaggc atcatatcag atccagttgg atcgctctcc    300
gactggacgg ccaataactc acataacgtc tgcctgtgga acggaatttc gtgcaggcca    360
```
aacacgaaac gagtggtttc aatttctctc cctgaatgct tgttgaatgg tacgctct         418

<210> SEQ ID NO 30
<211> LENGTH: 468
<212> TYPE: DNA
<213> ORGANISM: Pinus radiata

<400> SEQUENCE: 30
catgagggag agagagacca aggtctgtat cttcattttc tgtattttca catcatgggc         60
tctggtcgat tttggggttc ctgcagtttt tgcagcacaa gagactcaga tacaaatact        120
cctgaggatg aaagaggctc tggaggatcc cacaaatgca ctcagggatt gggatgggtc        180
tgaggattct ccatgtagat ggagagggat tgattgtaac gatgaaggtg ctgtgactcg        240
catacaactc catggaagtt ctctgagtgg tcgcattctg cctgatatct gcaatctcca        300
gagcctgata atctttgagc tagatcgaaa ttcccttat gggaatttcc ctccagaatt         360
ttcgaattgc agtcggttgg aacaattgaa tttgagctcc aatttgctga acgggtcatt        420
gcccgacctt tcaaaattga aggctctgaa atatctggac ctgtctaa                     468

<210> SEQ ID NO 31
<211> LENGTH: 409
<212> TYPE: DNA
<213> ORGANISM: Pinus radiata

<400> SEQUENCE: 31
ggcagttgga gtggtagagt gagaaataca cagcctaatc tgaaggaagt tcgagtaata         60
gactgagaaa tggatcttct tcttctcctc atcatgatgc ttgtgatgat gggtgtagca        120
atgcctactc attctcaacg tttccctt aatggatgga gtatgatggg gaaaccctct         180
ctgttcccat cctccatagc cgggtatcat gaaaaaggg atgtggaggc acttctgacc         240
ttccggaagg gcatcacatt ggatccatat ggatggctct ccaactggac ggccaataac        300
tcacataacg tctgcctgtg aacggaatt tcgtgcagcc caaacacgaa tcgagtggtt         360
tcaatttctc tccgttacgg ccggttgaat ggtacgctct ccccgtata                    409

<210> SEQ ID NO 32
<211> LENGTH: 518
<212> TYPE: DNA
<213> ORGANISM: Pinus radiata

<400> SEQUENCE: 32
gtagagtgag aaatacacag cctaatctga aggaagttcg agtaatagag tgagaaatgg         60
atcttcttct cctcatgatg atgcttgtga tgatgggtgt agcaatgcct actcattctc        120
aacgttttcc ctttaatgga cggagtatga tggggaaacc ctctctcttc ccatcctcca        180
tagccgggta tcatgaaaaa agggatgtgg aggcacttct gaccttccgg aagggcatca        240
cattcgatcc acatgaatgg ctctccaact ggacggccaa taactcacat aacgtctgcc        300
tgtggaacga atttcgtgc aggccaaaca cgaaacgagt ggtttcaatt tctctccctc         360
agcgctcgtt gaatggtacg ctctccccgt atattgggaa cctctctctt tgcagcaat        420
tagatctttc ctttaatgct ttgagtggga gaattccagc agagtttggg cagctgaaag        480
cgctacgaac atttgaagtc cgccataatg ctttgagt                                518

<210> SEQ ID NO 33
<211> LENGTH: 401
<212> TYPE: DNA

<213> ORGANISM: Eucalyptus grandis

<400> SEQUENCE: 33

| | |
|---|---|
| gttcttagat cctgaagaac ctatggcgtc ttgcggtggc cttgtgtcta ccttcttgtt | 60 |
| ggcaatcttt gtcactcaaa ttgtcgaatt cagtcattcc attgcttcga caaatgtaag | 120 |
| ttgtattggt gtggagaggg aagctcttct aaagttcaag catggtctca ctgatccttg | 180 |
| gaaacgcttg tcatcatgga ctggtgagga atgttgcaag tgggaaggag ttgaatgtaa | 240 |
| cgagaagaca ggccatgtcc tcaagctcga tcttcataat ccatgtattg aagagattga | 300 |
| tatgcttgaa ccttcatata agtgcaggtt gggaggtaac atagttcatt ctttaacaga | 360 |
| actgaagtat ctgaagcacc tggatcttag catcaacaac t | 401 |

<210> SEQ ID NO 34
<211> LENGTH: 434
<212> TYPE: DNA
<213> ORGANISM: Eucalyptus grandis

<400> SEQUENCE: 34

| | |
|---|---|
| ggagaaccca acattgcttt ctctgccact ctcactctcc ttctttcaat gtgttccaga | 60 |
| agagttgttt cttcaatgga gaccaaccca attcatctaa tctaccatgt atttttcatc | 120 |
| gtcatagggc ttgtctctgt ttctgcagcc gaacagagtg cttcctccag gaaaacggat | 180 |
| gcggaagccc tgatcctgtt caagaaaatg atccagaagg acccgagtgg agtgctatct | 240 |
| gggtggcagc tcgatcagga tctctgcgct tggtatggag tcacatgtta ctcagggagg | 300 |
| gtcactcaac tcgatcttca cggccaaagt cttgaagcga ccatgtcttt cgacccttttg | 360 |
| agttctttag acatgttaac tgtctcaatc tgtcatcaaa ctcgttcgcc atcgattcaa | 420 |
| cttccttgct tcaa | 434 |

<210> SEQ ID NO 35
<211> LENGTH: 442
<212> TYPE: DNA
<213> ORGANISM: Pinus radiata

<400> SEQUENCE: 35

| | |
|---|---|
| ggaagttgga gtggtagagt gagaaatact gaaggaagtt ggagtgatag agtgagaaat | 60 |
| ggatcttctt cttctcctgc ttgtgatgat gggtgtagca atgcctactc attctcaacg | 120 |
| ttttcctttt aatggacgga gtatgatggg gaaaccctct ctcttcccat cctccatagc | 180 |
| cgggtatcat gaaaaaaggg atgtggaggc acttctcagc ttccggaagg gcatcatatc | 240 |
| agatccacat ggatcgctct ccgactggac ggccaataac tcacataacg tctgcctgtg | 300 |
| gaacggaatt tcgtgcaggc caaacacgaa tcgagtggtt tcaatttctc tcccttactg | 360 |
| ccggttgagt ggtacgctct ccccgtatat tgggaacctc tctcttttgc ggtatttata | 420 |
| tctttcaaat aatgatttga gt | 442 |

<210> SEQ ID NO 36
<211> LENGTH: 493
<212> TYPE: DNA
<213> ORGANISM: Pinus radiata

<400> SEQUENCE: 36

| | |
|---|---|
| gctgctcggc actctcagac gaagttacga accatgaggt ccgtgtttcg aatctcgtcc | 60 |
| cttctcgtga tttctattct ggttctgctc acgctttctt ccgccattaa cgacgatgcc | 120 |
| gagatgctgc tcgcgttcaa gtcagccatg tcggatcccg acggcgccct ggccgggtgg | 180 |

-continued

```
actgagtccg acgccgccaa tttctgtggg tggactggag tcctgtgcaa cgaattcaac      240
agaacgagtt cgctggactt gaccaacatg aatctgtcgg gcatcattcc gccccggaca      300
ttatcgagcc tcgacagtct cgtgaatctc agcttggcgc tcaacaaatt cagcacgccg      360
ttcccgtcgg cgatcctcga catttccact ctgcgattcc tcaatatatc caacaataac      420
ttcagcggcg agatcccggc aaacattcct cggttagtga atctggagtt gctggacacc      480
tacaacaaca att                                                         493

<210> SEQ ID NO 37
<211> LENGTH: 536
<212> TYPE: DNA
<213> ORGANISM: Pinus radiata

<400> SEQUENCE: 37
ggagaagctg ctgctcatgg ctcccctgct gggaattctc cttcttcatg ctctcatttt       60
tagctatgga gaagaagctc acgtcgctgg ttcgaaccac acagaggttc gggcactcat      120
ggctctcaag gccgggattg ttgacacttc aggtcatctg agtgactggg aagtccatgg      180
cgatgaactt agtgcttcgc cttgttcttg gactggtgtg ttttgtgatt tggagtctga      240
gaacgtgacg gaactcgatc tctcacggat gaatctcact gggacgattt cagacgagat      300
tcgggagctg cagcacctga agtactgaa tattagcttc aatcagtttt ccggggcctt      360
tccagttgta atctttaatc tcaccaggct gcggagcctg acataaatc acaactcttt       420 cgaagggtat ttcccggccg ggatctcgaa gatgaagaat ctagtgaatt ttatagcttt      480
tagcaatagt ttcaaagggc ctctgccgct ggaattcgtg gagatgcttt tctgga         536

<210> SEQ ID NO 38
<211> LENGTH: 822
<212> TYPE: DNA
<213> ORGANISM: Eucalyptus grandis

<400> SEQUENCE: 38
ctctctcttc accaccactc ctcctcccct caccttaatc tctcctccga tcccacacca       60 aaaccccgc cccacctcca tggcggcccc ctcctcctcc gccgcctccg ccgccgtgtt      120
cgccctccac tcgctgctgc tgctgctgct gctcgccgcc gccgtcgagg acgacgtgct      180
ctgcctcgag ggcgtcaagc gctccctcgg cgaccccag ggttccctcg ccgactggac      240
cttcgccaac acctccgcct cccacatctg caacctcaac ggcgtcgcct gctggaacct      300
caacgagaac cgcatcatca gcctcagcct caccggcttc ggggtctccg gcggcctccc      360
cgagtccctc aagaactgcc acagcctcca gacgctggat ctctcccaga acaagctcga      420
cggccccatc cccgcccaaa tctgcgagtg gctgccttac ctcgtcaagc tcgatctctc      480
ctctaactcg ctcgccggcc ccatcccag ccagatcggc gactgtaagt tcctcaacaa      540
cttgattttg aacgacaaca agttgaccgg ccccattcct tacgaggtcg gtcgcctgga      600
ccggttgaag gtgttctccg tccggggcaa tgatctctcc ggatctatac cgtcggagct      660
gtccaaattc agttccgacg atttctccga caacgacgat ctgtgtggta ggcctcttgg      720
gtcgtgtggg gggttgagta agaaaagcct cgctataatt atcgctgcgg gtgttcttgg      780
agccgcagca tctttgttgc tagggtttgc gctctggtgg tg                         822

<210> SEQ ID NO 39
<211> LENGTH: 454
<212> TYPE: DNA
```

<213> ORGANISM: Pinus radiata

<400> SEQUENCE: 39

| | | | | | |
|---|---|---|---|---|---|
| ggagtggtag | agtcagaaat | ggatcttctt | ctgctcctcg | tcatgatgtt | tgtgtgctct | 60 |
| gtgatgatgg | gtgtagcaat | gcctacggat | ggattcactt | ctgttgaaag | cgttcctttt | 120 |
| aatggacgga | atcgccataa | aagggatgtg | gaggcgcttc | tgagcttcaa | agagagtatt | 180 |
| atatccgatc | catatggatc | gctcaccaac | tggacggcca | ataactcaca | taacgtctgc | 240 |
| ctgtggaacg | gaatttcgtg | caggccaaac | acgaaacgag | tggtttcaat | ttctctccct | 300 |
| gagtgctggt | tgaatggtac | gctctccccg | tatattggga | acctctctct | tttgcggcat | 360 |
| ttagatcttt | cttggaatgc | tttgagtggg | agaattccag | cagagtttgg | gcagctgaaa | 420 |
| gcgctacgaa | tacttgacct | ctctgctagt | catg | | | 454 |

<210> SEQ ID NO 40
<211> LENGTH: 504
<212> TYPE: DNA
<213> ORGANISM: Pinus radiata

<400> SEQUENCE: 40

| | | | | | |
|---|---|---|---|---|---|
| caaaccctct | gaaatatttt | tgtaattcct | tcattttatc | gatcgcccat | ctgaggagcc | 60 |
| gatggcacct | tccacagatt | tcatcctcat | cacctccaca | ctcatgctca | tctttgtttc | 120 |
| tgcaaacgcc | catcttcttc | atcattatca | tgagaaaagt | cgtgaacgac | tgcaggtcga | 180 |
| tatagaagcc | ctgcaagcat | tcaaggcctc | cctcacatat | gatccttctc | acgccttggc | 240 |
| caactgggat | tttgtcgcca | atcatgtctg | caattggact | ggtgtcacct | gcaaccctca | 300 |
| caaactgcgc | gtatctgccc | taaatctcta | caacatgagc | ctgcaaggga | ctatacctcc | 360 |
| acatttgggc | aatatctcct | ttcttggcgt | gttgaacctc | actttgaaca | gtttctctgg | 420 |
| cataatccca | aacgaattgg | gcaagctgcg | tcggttaaaa | cgtctgtccc | tcaagcagaa | 480 |
| tcagttgatt | tcgtccattc | caga | | | | 504 |

<210> SEQ ID NO 41
<211> LENGTH: 403
<212> TYPE: DNA
<213> ORGANISM: Pinus radiata

<400> SEQUENCE: 41

| | | | | | |
|---|---|---|---|---|---|
| cattccttct | cttctcgttt | gtgcaatgag | aatgtttcta | ttactcgttt | atttgttccc | 60 |
| ccttgtcact | cccttcgcgt | tttccacagt | gcaattatct | aatggctcta | atgctgtcga | 120 |
| tcaagaggct | gtgcttggat | tcctgtctgc | aatcactaat | gatccctacc | aatcgttacc | 180 |
| cactaactgg | aaatcaaatg | tttcagtctg | cgagtggaca | attatcaaat | gcaatgggtc | 240 |
| cagagtggtg | tccctaaatg | tgtcgagcat | gggattagaa | ggtacaatct | ctcctcttct | 300 |
| cggcaatctc | tcatttctgg | aaaaactcga | ccttcgcaat | aacaattttc | atggtcccat | 360 |
| tccctatcaa | ttgggaagcc | tggtgcgctt | gcagatgctt | atc | | 403 |

<210> SEQ ID NO 42
<211> LENGTH: 595
<212> TYPE: DNA
<213> ORGANISM: Eucalyptus grandis

<400> SEQUENCE: 42

| | | | | | |
|---|---|---|---|---|---|
| gagagacggc | gatggaggat | gaggaagaag | agacgacgac | ggcgacgatg | atgcgcggac | 60 |
| catgccgatc | cagagacggc | ggcgcagcag | cggcggcggc | ggcggcggag | gcggcggggc | 120 |

```
cttccaccgt gtgttgattt ctctctcccg ccctcccga ctccgccttc gggctcggcg    180
gacttgatta gtcgggcatg tgaaaaagaa tctttgactg ctcagattgt tgaacaacgt    240
gatggagtcc tgcaactgcg ttgagccaca gtggccagct gatgagcttt tgatgaagta    300
tcagtacctc tcagatttct ttattgctct ggcgtacttt tccatccctc tagaactcat    360
ctactttgtc aagaaatctg ctgtatttcc ctatagatgg gttcttgttc agtttggtgc    420
cttcatagtt ctgtgcggag caacccacct gatcaactta tggacatttg ccattcactc    480
aagaactgta gcatatgtta tgaccattgc aaaggtttta actgctgcgg tatcatgtat    540
tacagctctc atgcttgtgc atatcatccc cgatctactt agtgtgaaaa ccagg         595

<210> SEQ ID NO 43
<211> LENGTH: 397
<212> TYPE: DNA
<213> ORGANISM: Pinus radiata

<400> SEQUENCE: 43
gttcgttagc aatgcccact tctacctcaa agtgcaggtt aaggactctg gctgtggcat     60
acagccacaa gatattcctc aaatatttac cagatttatt catcctcgaa gtggatctaa    120
tcgaggtaat ggcagcggag gacttggact tgccatttgc aaaagattta taatctcat    180 gggaggtcac atctccatcg agagtgaagg ccacgacaag ggcaccatcg tcacttttgt    240
cgtcaaacta cagaaatgca gcaatgcaaa tgactcggca gcccacgaga tcacatctag    300
agctcagtct attcatgaaa gcacccattt tgctcggcat aaacctctca tagacactga    360
cagaacggtc ccctccagct cccagtatca aagaagt                              397

<210> SEQ ID NO 44
<211> LENGTH: 415
<212> TYPE: DNA
<213> ORGANISM: Pinus radiata

<400> SEQUENCE: 44
ataaattctc tcaaagagat ggtatgcact tatggtcctt atgctgccct ctgatagtgc     60
tcgcagatgg catgttcatg agttggagct tgtggaggtt gttgcagatc aggtagcggt    120
ggctctctca catgcggcaa ttttggaaga atcaatgaga gcacgagacc tgctcatgga    180
gcaaaatgtt gcacttgaga tagctcgaca ggaggcagaa acagctattc gcgctcgcaa    240
tgatttctta gcagttatga accatgagat gcgtactccg atgcatgcaa ttattgcttt    300
gtcatcgctt cttcaggaga cagagttgac tcctgaacaa cgatccatgg ttgagaccat    360
cttaaggagt agtaatctcc ttgcaacact catcaatgat gttttagatc tttca         415

<210> SEQ ID NO 45
<211> LENGTH: 526
<212> TYPE: DNA
<213> ORGANISM: Pinus radiata

<400> SEQUENCE: 45
atggcgagtc caccctcgac tccaacaggt atcaccaacg tagctcgtct cacgatgcgt     60
gctgaagccg gtggtgatgg tgacagtcac gcccttgccc tcggtagcga tccgatcgcg    120
acccaatcgc catcgacgaa gcgtcgtgcc gcatccgcgc catggccatg ggcgtatacg    180
cgtgtaccca ttgtggcggc gaccgcgggt gcactggaag aagagcagaa agagtgtatc    240
caagcaggta tggatgatgt cttgacgaaa cccatcgaca ggtatcagct gcaaaggaag    300
```

-continued

```
ctggccaggt tctcaccgcg tttcacatcg ctcgtagtag catcatctgc accagcaagc    360
cagcaagccc atcagtgaca tgtggcaata tgacatgcac aacagcatat taaagtcctc    420
tagttggtca tcataaccag caatacaagg caacaacaag caaatgcatt tcaatgtcat    480
agtcactgtt acacatcgcc accttgtccc aacttatcac catacc                   526
```

<210> SEQ ID NO 46
<211> LENGTH: 255
<212> TYPE: DNA
<213> ORGANISM: Pinus radiata

<400> SEQUENCE: 46

```
gacaagagtg ttgctgattg atgaccatcc actgttccgg gagggactgg caggtgcgat     60
ccaggccgag ccagatttcg aagtcgtcgg ccaggccggg accgtggacg agctgcgcgg    120
gcttgcgccg cagatcgagc cggacgtcgc gatcgtcgac ctgttgatgc cgtcggtctc    180
cgggatcggc gtcacccgcg agctgtgcga gctgctggct aggtgccgag tgctgggct    240 gtcggtcttg gtcga                                                     255
```

<210> SEQ ID NO 47
<211> LENGTH: 3567
<212> TYPE: DNA
<213> ORGANISM: Pinus radiata

<400> SEQUENCE: 47

```
aggcaatgca aggcaggca tgaggactt tttaaggatc gtgtagttgt taatgatggt      60
tcaagtgggt gcatctcaaa attttaaaca attatattga aggacttttg ggactttgta   120
taatatttga ctactatggg aaggatgggg agaatgcatg aatgtaaact gtagtccatt   180
cccctcccaa gtatcgagaa ttctttggat ttggattaca tttacatgtc attctcatat   240
tctgtgggtt ggcaagacca ggcggtatgg aagttgctgt gggtggctgt actgttcatt   300
ttcattaaaa gaatacagag gccaaagtct gtattaatcc cacgaagtca agctcggcat   360
tcatattttt tcctcctggc atttggttgc ggtactaatc cacaaatggc aattctgaat   420
atatgaattc tttctcttgt ggaaacctgg aaggacagaa accctcgatg aggttaagtt   480
tggtctgtat tcgttgagag gttcttcatc tgatatggat tggaccagaa ctggggcaca   540
tcatgtttat gttcaaggag aggcaatggg tttggtcgat aatccccagt ctcctagatt   600
tgggtttttg tttcgtgtga atgtaaatac aaattaagtt aagaaattcc tttgaaaaac   660
ccatattagg gctttgggcc tacatgggta ccattggaca ccgatcagaa gggcggtttg   720
agtgcgctgt ataagtggtt tctgttttga ttcagaggag cccatgtgtg tgatccgagc   780
agattcaaac gcgtgacttt gtttgtgttt tttcaaaagg ccgctgctcc ctgttatcac   840
acagttcaca tgccgtaagg acttgacgag attgttgcaa tgatctgtct gggtgggatt   900
gtcattgttt cattcctcct ccagaacatt gcaatggcat cagaggatgg gggttccaga   960
tgcaactgtg acggggaagg atggtggaat gttgagaaca taatgcaatg ccagatggtc  1020 agtgatttc ttattgcctt agcgtacttt tccattcctc ttgagcttct gtacttttg   1080 agctgctcca atagtcttcc attcagatgg gtcatagttc agtttggagc attcattgtg  1140
ctttgtgggc taactcactt tatcaacatt tggacatatg gtcctcagtc tttccatgta  1200
atgctggcac taaccatctt caagttctta accgcccttg tttcttgtgc cacggccata  1260
actcttgtaa ctctaattcc tgaattgcta cgggtgaagg taagggaaat ttttcttaaa  1320
aacaaggcaa gggaacttga tagggaggta gacattgtga aaaggaagga ggaaactagt  1380
```

```
tggcatgtcc acatgctaac tcaagaaata cgaagttctc tagataggca cactattcta    1440
aatactactt tgatttcact agcaaagacg ttgaatttgg aaaactgcac tatatggatg    1500
ccactggcag atggtactgc catggaggta tcccatgagc tcaaacgacg gcatttgcaa    1560
gtaccattaa ctgttcccac aaccgaccca gatgtgaaaa agattatgca tagcgaggat    1620
gcaatccttt taagtcctga ttctgccttg ggaaaggaga gtaatcacca ctggtcatta    1680
gccgggcctg tggcagcaat aagggtgcct tgtggaagg catcaaattt caagagtgga     1740
gcatcggtag atagagaaga atcatatgca ataatggtgc tagtcttacc ttgtgaagat    1800
gaaaggcagt ggagttctca agaattatat attgtcaaag atgtggcaga acaagttgct    1860
gttgccctat ctcatgcagc tgttttagaa gaatcacaga agctgaaggc tccacttatt    1920
gataagaata aaacattaca acaggcaaaa caggatgcat tgagagcaag caaggcacga    1980
cattcttttc aattggcaat gaaccgtgaa atgaggcttc ccatgcatgc tatttctgca    2040
ctctcatcta ttttacaaag tgctagactg aatgttgaac aactggctat gacaaatatg    2100
ctagctaaaa gtagcagcct tctctcaact ctcataaatg acataatgga ttttcagaa     2160
ttggaggata cttctttggt tcttcagtta caccccttcc agctacatgg tatgctgaaa    2220
gatgcagcac acctcacaga gaccatgtct agaagcaagg tcttctatt aaatgttgaa     2280
ataggtgatg ggatgcctga ccatgtgata ggagatgaaa acgaattct acggattatt     2340
ttacatatgg ttgaaatgc aatcaattca accaaacaag gaacaatatc aattcgcatc     2400
tgtgtcgaag acagagctga aggttggtgg gaccccaaca atcgacgatg gagaccctca    2460
ctatgcgaag gttttacata tttaagattt gagatcagga catctggctc tggaagtatt    2520
caaaatgaca atcccagttt cctgactgtt gtacaagatg gtaaaagtga ttcgtcatca    2580
tcaactgggg aaggacttgg ttttgctatt tgtaaaaagt ttgtgcagct tatgcatgga    2640
aatatttggc ttgagcctaa ctccaagggt gaaggctctg ttgtgacctt tttaattaga    2700
gtacaactgc agacatcaac tgcaaacaaa cattggctgt ctccagatga gaagatttac    2760
aagtcttcat ttaaaggttt gaaagttctt gtagcagatg acaataatgt aagtcgttca    2820
gttacgagaa ggctgcttca agagctaggt tgtcaaacaa ctgaagtaga ttcaggttac    2880
aggtgcttaa tgactttgct tcagtctgga agtgcatttc aattggtctt tctggaagtt    2940
tgcttggccc agatggatgg atatgaggta gccttccgta tacgacagaa attcagatca    3000
agaaaccgtc ctttggttgt ggctttaaca gctagtacga caaggagac catggagagg     3060
tgccttcaaa ctgggatgga tggtgttata cggaagcctg ttacgttaag agaaatgagc    3120
aatgagcttt ttaaaattgt acatcagaca aataacatcc acgaatagtg actacaagtg    3180
tactttgttc tgaggtgcag tccatctggt gaagattgat tgctttgaca ggttcagagg    3240
agtgcaaatt atggtgacaa tgagaccatg ctacacagtc agttacgttg agattcctg     3300
tgcttaaatt caaaaggtcc atggtcttct ccgagtgtta agaaacacgg tactttgcca    3360
tgtactttt tccattgcta ctaaaatcat tctgtcacac acaggttctg tatgggtaat     3420
tacctcatct catgcatggc gatgttagaa gtcctgggac ccatttgaca agtcactgac    3480
tgttttagct caattcttac agaagatgaa atcaaaatta tattgatatg aagctcatga    3540
ttcttattg tgatcaaaaa aaaaaaa                                         3567

<210> SEQ ID NO 48
<211> LENGTH: 476
<212> TYPE: DNA
```

<213> ORGANISM: Eucalyptus grandis

<400> SEQUENCE: 48

| | |
|---|---|
| agacgatgcg agcgaaacaa atgctagcaa caatgtcaca tgagataagg tctcccttg | 60 |
| ctggggttgt tagcatggcc gagattcttg cacaaactag acttgatcat gagcagcggc | 120 |
| aattgttaga tgtcatgctt tcttcgggag atttggtcct tcaactaata atgacattc | 180 |
| ttgacctttc gaaggttgag tcagggtaa tgaagctgga agctacaaaa ttccggccga | 240 |
| gggaggtagt aaagcacgtg ctgcagactg ctgcggcatc attacggaag atattaacat | 300 |
| tggaaggaca tgtagcagat gatgttccta ttgaggtcat cggagatgtt ctaagaatta | 360 |
| gacaaattct caccaacttg atcagcaatg ccatcaaatt tacacatgaa gggaaggttg | 420 |
| gcataaatct atatgtggtt ccagaaccat ctgtcgagaa acagaagaa tgtcct | 476 |

<210> SEQ ID NO 49
<211> LENGTH: 513
<212> TYPE: DNA
<213> ORGANISM: Eucalyptus grandis

<400> SEQUENCE: 49

| | |
|---|---|
| gtaagattga gattgaggct gtgcagtttg atctaagggc catattggat gatgtcttgt | 60 |
| ccctcttctc ggggaaatct caagaaaaac gagtggagct agcagtttac atttctgaaa | 120 |
| atgttccgga aagttgatt ggtgatccag ggagatttcg gcagatcatc acaaatctta | 180 |
| tgggaactc aattaaattc acagagaaag gacatatctt ggtcacagtc catcttgttg | 240 |
| atgaggtgat gaactcaact gatgctgaga tggaatcagc aacaaggagt acgttgagcg | 300 |
| gcttcccagt accagacaga cgactcagct gggcaaaatt taggacattc agccaggaag | 360 |
| gccctgcgtc tccggtgccg tcatccttct ctaatccaat caatctcatt atttcagtgg | 420 |
| aggatacagg gataggtatt cctccagagg cgcaaccccg cgttttcact cgtttcatgc | 480 |
| aagtgggccc atcaatttct cgaacacatg ggg | 513 |

<210> SEQ ID NO 50
<211> LENGTH: 1995
<212> TYPE: DNA
<213> ORGANISM: Eucalyptus grandis

<400> SEQUENCE: 50

| | |
|---|---|
| cttgagcata aaatatccat ttcttcactt aagacaaagt tgaagcaaca tggtagtcac | 60 |
| gcaagaaggg catccaagaa agacaacaaa gtgaccctct ggttcgaagt tgatgacact | 120 |
| ggctgtggaa ttgatccaag caaatgggaa tccgtttttg aaagctttga gcaggccgat | 180 |
| ccatcaacaa ctcgattaca tggcgggact ggtcttggcc tatgcatcgt acgaaccttg | 240 |
| gtcaacaaaa tgggtggaga atcaaagtc atcaagaaga atgggcccggg aactctcatg | 300 |
| agactttact tactcctcaa tgcacctgtt gatggcacgg aacataactg ctcagtggat | 360 |
| tatgccgtgc acaacataag agtgctactc gcacaacatg gaagcacggg tagatttata | 420 |
| atgtctggat ggctgcgcag aaatggagtt tccactctgg aagcatctgg atggaatgaa | 480 |
| ttgacccaga ttcttcagga actctaccaa ggcagaaatt caggtgctcc atacaggact | 540 |
| gttaatacgg aacatgcaca tgaactcccg agatcagaag tgacaacttt cgatgatatt | 600 |
| caaagtgaga tcctcatcat agtcgtggat atagagctac ttgacctaaa cacagatata | 660 |
| tggaaggaac agctcaattt cctggacaag taccacagga aggcaaagtt cgcgtggatg | 720 |
| ctaaaccatg acaccttcaa tgccattaag gtggagctcc gaaggaaagg acacatgctg | 780 |

```
atggtcaaca agccgctata caaggccaag atgattcaaa ttctggatgc tgccataaag      840
gagaggaact ctgaactcct gaaaagggcc tccaattctt caaaaagcat gaataaagaa      900
gaggacttgc acgagtgtct agaaatcgac tctgagcact atgagggagc gagctctgat      960
gaactggaca cagttgaaac atcacgttct ggttgtacca atacatctcc tggtgaacaa     1020
aagcaacagg aagggatcaa aacccctcct gctctacaac acaggacatc gaactatcac     1080
tcattcaatt ctactctgct gtcttccgac tataacaatt tagggaacaa agaagaagcg     1140
tgtccaacta gtcccccttt ggaccaccca gataatgccg aaggcagatt caagtgcacg     1200
aggagcgtgt tttcttcaaa agaaaaggaa gatggaaatt cagaagcaca ggaacaactt     1260
ctgatcagca agcgtcctcc agccaaagtt gattcgtgtt ccagtaaaga attggaccag     1320
aaagggtctc tggagggcct gtgcatacta cttgccgaag acacgccagt gcttcagaga     1380
gttgctacga tcatgctgga aaagttgggg ctaaagtca ttgctgttgg agatggcttg     1440
caggcggtga atgccctgaa cagcagtcta gatgtagatg cagaagactt caggacgacg     1500
ttgcatttgc aaaacgcgaa caggatgcct caagcaggaa cacgaagttg caaccttac     1560
gacctgatcc ttatggactg tcaaatgccc cagatggacg ggtacgaagc aacgaaagca     1620
atcagaagat ccgaggccgg aagcggcctg cacattccga ttgttgcgct gaccgcgcat     1680
gccatgtcat cagatgaagc caagtgcttg gaggtgggaa tggacgcata cttgacgaag     1740
ccaatcgact ataagcttat ggtgtccaca attctgtcgc tcaccaaggg agtcaactga     1800
gagaacctgc taagacaact tagagagaac caaagaaagc cagattttaa agtttacaca     1860
gttttttgctt ttgaaatgtg aaagaatcag tatgattaac gaactgggca agtataccag     1920
tgacccccatc tgcaatctgt aaagacatct gagtttctct agcttatttc tgagcatatt     1980
cggaaaaaaa aaaaa                                                        1995
```

<210> SEQ ID NO 51
<211> LENGTH: 461
<212> TYPE: DNA
<213> ORGANISM: Eucalyptus grandis

<400> SEQUENCE: 51

```
ctctttctac cggcgcttct tcagcaacaa ctggcatggc gagcaacggc ttggtctcgc       60
cgcggaggag gtcgtcgggc cagtttgacg gcagcgaccc gtctccgtgc ggttccgagg      120
aggtccacgt cctcgccgtc gacgacagcc tcgtcgatcg gaaagtcatc gagcgcttgc      180
ttaagatcac ttcctgcaaa gtgacggcag tggatagtgg actcagagcc cttcgatatc      240
ttggtctgga tgaggagaaa acggctggag atttttaacgg gttgaaggtg gatatgataa      300
ttaccgacta ttgtatgccc ggaatgactg gttacgagct cctcaagaaa atcaaggaat      360
cctctgctct gagggaaatt ccggtggtga tcatgtcgtc cgagaacgtc ttggcgcgaa      420
tcgacaggtg tatggaggaa ggtgcggagg atttcatcgt g                          461
```

<210> SEQ ID NO 52
<211> LENGTH: 570
<212> TYPE: DNA
<213> ORGANISM: Eucalyptus grandis

<400> SEQUENCE: 52

```
atcatttctt cctgcgcttc ttcagtaaaa actggtatgg cgaggaacgg cgtggcctcg       60
tggcggagga ggtcgtcgga ccagttcgac gacccgtcgc cgtgcgggtc cgaggatgtc      120
```

-continued

```
cacgtcctcg ccgtcgacga cagcctcgtc gaccggaagg tcatcgagca cttgcttaag      180
atctcttcct gcaaagttac ggcagtggat agtggaatca gagcccttca atttcttggc      240
ctggacgagg agaaagcagc tggcgatttt aacgggttga aggtggattt gataataaca      300
gactattgta tgcctggaat gactggttac gagctcctca agaaaatcaa ggaatcctct      360
gctctgaggg aaattccggt ggtgatcatg tcgtccgaga acgtcttggc acgaatcgac      420
aggtgtttgg aggaaggtgc ggaggacttc atcgtgaagc cggtgaagct gtcggacgtg      480
aagcggttga gggatttcat gacgagagac gtcggagaaa gagtgaggag cgacggggag      540
ggcaccaccc acaagaggaa gctgcaagag                                       570
```

```
<210> SEQ ID NO 53
<211> LENGTH: 1489
<212> TYPE: DNA
<213> ORGANISM: Pinus radiata

<400> SEQUENCE: 53
```

```
gcggccgcgt cgacggagga tacagggatt ggaattcctc tgcccgcaca acatcgagtt       60
ttcaccccat ttatgcaggc agacagctct acatctcgaa cttatggggg tacaggaatt      120
ggcctcagta ttagccgatg cttgattgaa ttaatgggcg gtgagataag atttataagc      180
cgcccaggta ttggaagtac attttctttc actgctttgt tcaaagtggg ccaagcaggg      240
gctgatggtg acggtgattt actacgaggt gcaagactgc cgactcattt caagggcatg      300
aaggcacttg tattggatgg taacccagta tgttccctag tcacgaaata ccatttacag      360
aggtttggca tagaggtgga cagcattact agttctaaag tggctttatc tatgctgaat      420
ggaatggatg gttttccaac agaaggttgt agcgtaaaaa tggtatagaa tatggtgcta      480
atagagaagg atgcttgggg gtcccggcac tggcatctta tttccttcgc aagtacgagt      540
aggtctcttt ccaagaggac cctttctaca gtcaaagggt ttattaaaga tgattctttt      600
ggctacatcg ctgacagctg aagaaactca gaaagctaaa gctgcagggt ttgcagagac      660
agttattcta aagcctttac gtgctagcat gttggctgtt tgtcttcagc tagctcttgg      720
attttgcaac aggagagagc atctaagaga accttcgaag acctcctctc ctctaagtaa      780
tgtattgtct ggaaaatcca tacttgtggt agatgacaac atcgtcaatc gtcgagtcgc      840
tgctggtgca ctgaagaagt atggtgctaa tgttatttgc acagacagtg ggaaatctgc      900
aatatccatg cttcgacaac cacacaattt caatgcatgt tcatggatg tgcagatgcc      960 agaaatggat gggtttgaag ctacgcgaca gatcagagca gcagaacttg ctaacatgga     1020
gtgtacaagc aacggcggtg aaactctggc taccaacaat agatggcatg tgccaatctt     1080
agcaatgacg gccgatgtaa tacaggcaac ccatgaggaa tgcctgcgat gtggcatgga     1140
tgggtatgtc tcaaaacctt tgaagaaga acaactatac aaggccctag ctccattttt     1200
tgaggagtca ttatttagat attgtttaaa tattggcttt cagtgtttaa ggatttcata     1260
ttccccgtgt ataatatata gaataggatc caacgattcg ttttttgtct gaaagttaga     1320
cctccttgct tgaggccttg ttatggcatg tagattgatt gcaagcatgt agagttttat     1380
atgctgcggg tgaagtccgt gtaagatcaa tatttgtaaa tttgaagtta gggctgaatg     1440
gaaatttaaa ggcatttgct gtgcgggtat ttgcattaaa aaaaaaaaa                 1489
```

```
<210> SEQ ID NO 54
<211> LENGTH: 370
<212> TYPE: DNA
<213> ORGANISM: Pinus radiata
```

<400> SEQUENCE: 54

```
gtcaaagggt ttattaaaga ttattctttt ggctacatcg ctgacagctg aagaaactca      60
gaaagctaaa gctgcaggtt ttgcagagac agttattctg aagcctttac gtgctagcgt     120
gttcgctgtt cgtctgcagc tagctcttgg attttgctac agaagagagc atctaagaga     180
acctttgaag acctcctctc ctttaagtaa tgtattgtct ggaaaaggca tacttgtcgt     240
agatgacaac attgtcaatc gtcgagtggc tgctggtgca ctgaagaagt atggtgccaa     300
tgttatttgc acagacggtg ggaaatctgc aatttccatg cttcgacaac cacacaattt     360
aatcactagt                                                            370
```

<210> SEQ ID NO 55
<211> LENGTH: 398
<212> TYPE: DNA
<213> ORGANISM: Eucalyptus grandis

<400> SEQUENCE: 55

```
ggtaatcgaa agagagacgg aaaatacagc aaaaggaaga gcacgagttt cgcttcaact      60
atttctaccg gcgcttcttc agcaagtggt atggcgagca acggcttggt ctcgccgcgg     120
aggaggtcgt cggaccagtt tgacggcagc gacccgtctc cgtgcggttc cgaggaggtc     180
cacgtcctcg ccgtcgacga cagcctcgtc gatcggaaag tcatcgagcg cttgcttaag     240
atcacttcct gcaaagtgac agcagtggat agtggactca gagcccttcg atatcttggt     300
ctggatgagg agaaaacggc tggagatttt aacgggttga aggtggatat gataattacc     360
gactattgta tgcccggaat gactggttac gagctcct                             398
```

<210> SEQ ID NO 56
<211> LENGTH: 438
<212> TYPE: DNA
<213> ORGANISM: Eucalyptus grandis

<400> SEQUENCE: 56

```
tgttctttca ccctttcctc ctcctccccg ttgttcctcg ccgttgttct tggtcgatcg      60
ccgatcgaaa tgggtgtcac cgccgcgtcg caatttcatg tcttggcggt tgatgacagt     120
ctcatcgaca ggaagctgat tgagaggctc ctcaaaacct cctcttatca agttactgca     180
gttgattctg gaagtaaggc tctggagttt ctgggcctga atgagcagca gcccagaaat     240
gccaacgcta cctctgtctc tccaagctat catcatcagg agatagaagt gaatttgatc     300
atcacagact atttcatgcc agaaatgaca ggatatgatc tcttgagaaa gatcaaggaa     360
tcgaatagtt acaaggacgt accagttgtg atcatgtcgt ctgagaatgt tccctcaaga     420
atcagccaat gtttggaa                                                   438
```

<210> SEQ ID NO 57
<211> LENGTH: 1280
<212> TYPE: DNA
<213> ORGANISM: Eucalyptus grandis

<400> SEQUENCE: 57

```
gggaagttgg ctgtctatgt ctctgatcgg gtaccggaag ctgttattgg tgatcctggt      60
cgattccggc agataattac aaatcttgtt gggaactcaa tcaagtttac acatgaaggg     120
catatatttg tctcagttca tctgctagaa gaaggatgca gtcagcatga ttttagagat     180
gtggagaaga gactaagttc aaacttagtt gaagatacat cggacaaaac ttttaataca     240
```

-continued

```
ttgagtgggt tcaagtggt tgacagaagg aaaagctggg agcgctttaa gaagttaaat        300
cggtccgatc aaattgatgt gaatgaatca gttgaagtac ttgttactgt tgaggataca        360
ggtgttggaa ttgccagaga ggcacaaagc cgcatattca cacctttgt gcaggctgat         420 agctccacat cacgtacata tggtggcact ggaattggct tgagtattag caaatgtcta        480
gtggatctta tgcacgggga gatcgggttt gtaagtgaac cggcactgg aagtacattt         540 tcctttactg tacccttgc aaaatgtgaa atgaactgtc ttgaagtgaa ggggcaaaat         600
tacgattcaa tcatatcaga gttcagagga ttgagagcct tggtgataga taaaagacac        660
atccgagctg aggtcgcaag atatcatctt gagagactaa gaatatcagt ggacgtcgct        720
tgcagtttga agtcagcctg tacttaccttt ccaactctt ctagcccaag ggaactatcg        780
gattttgaca tggttctcat cgacaaagat gtttgggaca ggcaaacagg tttagaactc        840
aatatttcac tttggaaaca caggcaaaat ggcagcaatg gagtgtcaat acgtcccaag        900
atttttcttc tggctacatc cattagtcca attgagcaca gcgagctcaa attagccaac        960
ctggtagata tgtgctggc aaagcctctc agattgagtg tcttgatatc ctttctccag        1020
gaagccctcg gtaatggtaa aagaggcta tctgatagga gaaaagtatc aactcttggc        1080
agtttgctga aggaagaag aatcttggtt gtggatgaca acttggtaaa cagaagagta        1140
gcagagggtg ctttaaagaa atatggtgcc attgttacct gtgttgggag cggtaaggat        1200
gctgtggcca agcttcagcc gccccatgac ttcgctgctt gcttcatgga tttgcaaatg        1260
ccagagatgg acgggtttgc                                                    1280
```

<210> SEQ ID NO 58
<211> LENGTH: 582
<212> TYPE: DNA
<213> ORGANISM: Eucalyptus grandis

<400> SEQUENCE: 58

```
tcagcttcct cttcctcttc cccttataac cagacatcaa aaccccccca tttcctttct        60
tttcaaaact caccaggcca cccacagttc tttcccactt cagactctct ctctctctac        120
atctgcctct ggataatttt ccgttttcca cagaaagggt ccttttgttt cttgtcccta       180
gttgttcata catataggtt tgtatctctg ggaagcagag atttctggag gatcttttgt        240
tggccttcac ttttgattga tgatggagag cagcaaaggc ttctcttctc ctcggagcaa        300
cgggttcccc gccggattgc gcgtccttgt ggtcgatgac gacccacttt ggttgaagat       360
cctcgaaaag atgctcaaga aatgttctta tgaagttacc acatgtggtt tagcaagaga       420
cgccctgaaa ctgcttcggg aaaggaaggg tggatatgca attgttatta gcgatgttaa       480
catgccagac atggatggct tcaaactcct agaacttgtt ggcctcgaga tggatcttcc       540
tgtaataatg atgtctgtgg atggggagac gagcagagtt aa                         582
```

<210> SEQ ID NO 59
<211> LENGTH: 534
<212> TYPE: DNA
<213> ORGANISM: Pinus radiata

<400> SEQUENCE: 59

```
gctgaaactt gatagaagct gcagagttac acgagttgta tgattagtca gcattattga        60
aggaacggca ccttttggtt cttgcttcga gattttggag cccggattcc cgatgtacac       120
aatagcgcat gaaagtaaat acgcaactgc ataattttcc cttcagcagc catggttacc       180
tcacgaatgt cttcggcgat gagaatgaag aaggaaaaaa atgctgcatg tggtgagcat       240
```

```
ggggatgaac tggttcgatg cgacgaaatg catgtattgg cggttgatga ttgcctgata      300
gaacggaagg tcattgaaaa gcttttgaag actaactttt tcaaagttac ctctgtagat      360
agtgccgaaa gagcgctaga agtcttgggg tttcatgaag agcagtcgac atgtgcgacc      420
actaacgcgt tcaaggttaa tatgatcatt accgattatt gtatgccagg aatgacgggc      480
tatgatctgc tgaagaaagt caaggaaacc aaatgtctga aggagattcc tggt           534

<210> SEQ ID NO 60
<211> LENGTH: 584
<212> TYPE: DNA
<213> ORGANISM: Pinus radiata

<400> SEQUENCE: 60
caggaatgga tggatttgaa actacaaaaa gaatttgaca gatggaacaa agtccaagct       60
aggaattcct actgggacag tcatcctcag agccacgtga aaatatctcg aatttccacc      120
tactgatctt ggccatgact gcagatgtga ttcacgctac tcatgaataa tgcacaaagt      180
atggaatgga cggatatgtt tcaaagccct ttgaagcgga acaactttt agagaagttt       240 cgctcctttt cctggtcatc actgaatcaa aacttgtaga gaggccacca tagatggtta      300
attgttttgg tgagcaaaag tcttggttgt ttaggcactt tggcagcctt actggtgaac      360
tttcgaattc tttaacaaga gagttttctc tggcctctcc ttagctacac atttcttgat      420
tctcttgctt ttagagcagt tggatttcct tttgatagat gcaattgaaa ttcgctgaca      480
tatctcatgt gaaaccaaag ggattttctt cggaaaccat atacataaag aagctaaggt      540
cacctgctgg agttgaattt tcaaaaaaaa aaaaaaaaaa aaaa                       584

<210> SEQ ID NO 61
<211> LENGTH: 702
<212> TYPE: DNA
<213> ORGANISM: Pinus radiata

<400> SEQUENCE: 61
agaagggctg tttcagtttg agttgcccct gaacaaaatc ttctatgaat ttattcaaga       60
aaagattcaa gccagcaatg cttgggtttg agctgaaaaa aacagagaca gagacagaag      120
aactaaattt attagaaaga aaaaactaaa attactaaca ggtggataca gatgcagagg      180
gttaaagtaa tgaagaagat aaagagaggg tgattcaatt tgtttgtaga agccgacgca      240
gggcttcaac aacctcaacc tcaagacgac tacgggtttc tttcatggtt ggttggagaa      300
cgaagagcaa agcaccagaa ttagaagaag aaggatgttt agggttcaaa gagggtttgg      360
attaggtttc accaaccgag gtcgatctat ctcaagtatc tatgatggtt cccatcagat      420
agaagcttcc aagatttat acgagcttaa aacagtgaat tcaagcgaag gaaaaaagtt       480
catgcaaata aatggaaaac aggtggaggg aggagggtga tacgaattta atgaacaata      540
gaacatcaat gagccataag gcaaggtcga aggaagcata agagcagagc cataaggcaa      600
ggttgtagga agcattagag cagaacaaag cacaacatag aggaaataaa tacctggaat      660
tagaagaaaa gcagccctgt cggtacatca aattgtctta cg                        702

<210> SEQ ID NO 62
<211> LENGTH: 600
<212> TYPE: DNA
<213> ORGANISM: Pinus radiata

<400> SEQUENCE: 62
```

-continued

| | |
|---|---|
| gtcgacagac aggcaaagca aggaaggagg acagagggca gatggtttct gatgtcaatt | 60 |
| aatgagacag gcacagtaag gaaggaggac agagagaggg gttcatgtga aacccaacgg | 120 |
| acacagaagg aagaaggaca cagaaggaat aagggctgct tcagtttgag ttgccgttga | 180 |
| acaaaatctt cgatgagttt attcaagaat agattcaagc aagcaatgct tgggtttgag | 240 |
| cagagaaaaa acagagacag agacagaaag aactaaattt attagaaaga aaaagctaaa | 300 |
| attaataaca ggtggataca gatgcagggg gttaaagtaa tgaagaggat aaagagaggg | 360 |
| tgattcaatt tgttggcagg agccgacgca gggcttcaac aagctcaacc tcaagacgac | 420 |
| tacgggtttc tttcatggtt ggttgaagaa cgaagaagag caaagcacca gaattacaag | 480 |
| aaggaggatg tttagggttc aaagagggtt tggattgggt ttcaccaacc gaggtcgatc | 540 |
| tatctatcat ggttcccatc agatagaagc ttccaagatt ttatacaagc ttaaaacagt | 600 |

<210> SEQ ID NO 63
<211> LENGTH: 1656
<212> TYPE: DNA
<213> ORGANISM: Pinus radiata

<400> SEQUENCE: 63

| | |
|---|---|
| gcggccgcgt cgacctttat aaaccatatt ataagactga gtaatgtgac aattaccatt | 60 |
| accatatacc ccacagaaga agagagtcag tatttgggtt cccagcttct gcacaatctg | 120 |
| taatattttg ggtttattga gatggctgta tctcaacatc tgttttgag tgctcaacgc | 180 |
| ctaaatggga gagaggatga aggcagtctg tacctttga gagcagggt gaactgggac | 240 |
| ctgctgataa tgggtgttgc tctggtggcc tgtttggcta ttttagggat ggtttggaag | 300 |
| cgtaggagga catggtctta ttgtgagggt ttgcaggaag aagatgcagg ccagagagct | 360 |
| caggaaaccc aatgctctaa aggattcatg accaacgtgt tcacaatac aagagattgc | 420 |
| agatcagaac agattatttg ggatgatatc cacatttcat ctcagactga aaccagaagt | 480 |
| cagaaagtta gaactgtgaa gtcaaaaagt tccatgattt ctcgggattc ttgtagctcc | 540 |
| cccagacgaa tcttgctcgt ggaagacaca caaatcaaca gaataatttt cgggagggtg | 600 |
| cttcaaagcc ttaatcttta ctgtgaagaa gctgagaatg ggaaagtagc agtggactat | 660 |
| ttcaagcagg gcagaacata tgatcttgtg ttaatggaca aagagatgcc tgttatggat | 720 |
| gggcatgagg caacaaggca actgagatca atgggagtca agacacccat tgttgcactt | 780 |
| acagcaaata ccttgcaatc tgataaagac ctcttctttg aggctggtgt tgatgatttt | 840 |
| caatcaaagc ctctgtccag agacagactt gtacaattac tagatcaata tggtgtggat | 900 |
| ggttgtgctg gcaacagaag gggttgaaag agtttcaagg tttcattgta ttatacccat | 960 |
| ggcttcgtta tgaaaaaaa cagtgcagat tgcaggttgc ctgctttgta agtcttgatc | 1020 |
| tgcattattg cagtgatttg attaagccac gaggaatatg gttttagggt ttccagacat | 1080 |
| ttgcaatcct gcaatcctcc tgagcaacac tgaactttcc tacatcttgg ggaaggcagg | 1140 |
| taggctagag ctggaagtaa aatgtgaaca agttgtgaaa agtgcataaa ctggtataaa | 1200 |
| gcaaaacaat tgattttttt caagcagcag tgtcaaagct gaagttgcag cactattaaa | 1260 |
| aagctggaaa tgaatcttgg tggggagaga agaatttga agttcagca ctattaaaag | 1320 |
| gctggaaatg aatcttggtg ggggagagaa cgattctttc tctcgactat ccaagttata | 1380 |
| ctcaattgat cttcatcttc tgtgaaggac tttggtcaca ggaattcctt ctcaagatca | 1440 |
| atcaaaacgg ttttgagcca cacaaattgg caacaggctg ggatcaacaa gaagacttat | 1500 |
| gagagagctt ttagttttt cagtggagcc gaacagtggg actttgggaa atgcttgttc | 1560 |

```
aaagttctta actccttcgc ctatatgggt ggcctgcaca atttgtatct ataataagga    1620
tttcttaaaa aaaaaaaaaa aaaaaaaaaa aaaaaa                              1656

<210> SEQ ID NO 64
<211> LENGTH: 360
<212> TYPE: DNA
<213> ORGANISM: Pinus radiata

<400> SEQUENCE: 64
gggtatttgg gttctacgtc ttctgtgcaa cctgttaatt tctatctgtt ttggtttatt      60
gaggtggctg tacctcaaca tctggttttg ggtcatcaat acctaagtgg gacagaggga    120
ggagacggtc tgtactttct gagagcaggg ttgaactggg tccttctgat aatgggtgtt    180
gccctggtgg cctgtttggc tattttlggg atggtttgga agcgtaggag gacatggtct    240
tattgtgggc ctatgcagaa agaggatgca agccagagag ctcaggaggc ccaatgctct    300
aaaggatgca tgaccaatgt gttgccgaat acgagagctt gtagaggagc acacattata    360

<210> SEQ ID NO 65
<211> LENGTH: 466
<212> TYPE: DNA
<213> ORGANISM: Pinus radiata

<400> SEQUENCE: 65
aacagattgc agatcagcac gcattatttg ggatgatatc cacatttcat ctcagactga     60
aaccacaagt cagaaagtta gaactgtaaa gtcaaaaagt tccatgattt ctcaggattc    120
ttgtagctcc cccagacgaa tcttgctcgt ggaagacaca caaatcaaca gagtaagtta    180
taccaggact gattcgttgt tggttttag gatgctgctt gtggccatat aaggttaatt     240
ttcctggagc ttgctgctga ggtctcattc attattttac actgaatcaa cctcagataa    300
ttttcgggag ggtgcttcaa agccttaatc tttactgtga agaagctgag aatggaaagg    360
tagcagtgga ctatttcaag cagggcagaa catatgatct tgtattaatg gacaaagaga    420
tgcctgttat ggatgggcat gaggtatgca actgttaaat ctgtaa                  466

<210> SEQ ID NO 66
<211> LENGTH: 642
<212> TYPE: DNA
<213> ORGANISM: Pinus radiata

<400> SEQUENCE: 66
aagcgatttc tggagggcca cgagctgtct tatctccgag ccatcggtgt tattattctg     60
tccgctgtgc tgaagcggcg catgatcctg gcggacaagg cgaagagtct cttcatctcc    120
aacatatcac acgagttacg gacaccgctg catgggattc tcgcagcggc ggaactgctc    180
ggcgatagcc cgttaaatca ctcgcagctc tccttcctcg agactgtaca ggcgtgtggg    240
acttcgcttg tcgagacggt aaatcacgtg ttagatttca ccaagctgag cgggaactcc    300
aaggcgggcg gggtggagaa ggtgatcgtg ccgaccaggg tggatctgat gcagctcatc    360
gaggaggcgg tggatgggtg ctggattgga catcgggccc ggacagcgat catgggcgac    420
acgggcatcg gaagcgtgta ttcgccaccg gaggattat cttctcccaa gcagctcgtt     480
gagaccgtcg tcgacattgg atggcgcaaa aagggatggt cgctcaagtg cgagaaaggc    540
gggatccggc gggtgctgat gaatgtgttt ggaacagcc tgaagtttac tactaacgga    600
tacgtgcacg taattctgcg tgagctgcct cggagcggcg at                      642
```

```
<210> SEQ ID NO 67
<211> LENGTH: 909
<212> TYPE: DNA
<213> ORGANISM: Eucalyptus grandis

<400> SEQUENCE: 67
gttgaaaact cctcaacaag aaatcgtgcg ttcgtacagt ttcatctaca tcaggaaagg      60
ctctttgctc tgatcttttc cttgcgagtt aatcattatg acgatggccg gcgaaattct     120
ccggcggcag tcgccggcgg aggtcgactt gtgtggtggg tcgggtcagg agctgcatgt     180
tcttgcggtg gatgatagcc ttgtggatag gaaggtcatt gagaagctgc ttaagagatt     240
gtcttgtaaa gttacggctg ttgatagtgg attgagggct ttgcagtttc tgggattgga     300
tggagagaag agctctgttg gacttgatga tttgaaggtt aatctgataa tgactgatta     360
ctccatgccg ggcatgactg gatatgagct tctcaagaag atcaaggaat catcagcttt     420
cagagaaacg ccggtggtga tcatgtcctc cgaaagaatc ctcgcccgta ttaaccgatg     480
tctagaggaa ggagcagagg aatttcttgc gaagccagtg caactgtccg atgttcagcg     540
cctgaaaaat ttcgtgatgg gtgggggaga gtttgcccg acagaagaa tcaacaagag      600
aagactcgaa gaaataacg ataacgacga caacgaaaat catgccccat cgccggtgtc      660
gccctgtgc agtcgcgatt gggcagtgtg ctcatcttca tcgtccgatt cttcatcgcc      720
atctatagcc gtgtcttcat cgaagaggct taagatacat catcaagctt gaggatattc     780
attcgtatat accagaattt gatttattgt tgttttttgg ccgatgatcg gcatattcat     840
ggctaggaat ggcgcacctt ttgttcagta aatataatat gatctctttc ccctaaaaaa     900
aaaaaaaaa                                                            909

<210> SEQ ID NO 68
<211> LENGTH: 666
<212> TYPE: PRT
<213> ORGANISM: Pinus radiata

<400> SEQUENCE: 68

Met Glu Arg Leu Glu Met Ala Met Phe Leu Met Leu Leu Ile Ile Phe
  1               5                  10                  15

Phe Phe Arg Asp Cys Glu Ala Gln Gly Lys Ser Asp Tyr His Ala Leu
                 20                  25                  30

Ile Ala Phe Lys Ala Ser Ser Asp Ile Asn Asn Thr Leu Ala Phe Ser
             35                  40                  45

Trp Thr His Lys Asn Pro Cys Arg Arg Lys Trp Tyr Gly Val Gly Cys
         50                  55                  60

Glu Asn Gly Arg Val Val Arg Leu Val Leu Gln Asp Leu Asp Leu Val
 65                  70                  75                  80

Gly Pro Ile Asp Ala Leu Thr Gly Leu His Glu Leu Arg Ile Leu Ser
                 85                  90                  95

Leu Lys Arg Asn Ser Leu Asn Gly Thr Ile Pro Asp Phe Leu Asn Trp
            100                 105                 110

Arg Ser Leu Lys Phe Leu Phe Leu Ser Asp Asn Tyr Phe Ser Gly Pro
        115                 120                 125

Leu Pro Ser Thr Ile Ala Ser Leu Asp His Leu Arg Leu Asp Val
        130                 135                 140

Ser Asn Asn His Leu Gly Gly Gln Ile Pro Leu Ser Ile Thr Ser Met
145                 150                 155                 160

Thr His Leu Leu Thr Leu Arg Leu Glu Asn Asn Glu Phe Ser Gly Ser
```

-continued

```
                165                 170                 175
Ile Ser Asp Leu Met Leu Pro Asn Thr Val Glu Glu Phe Asn Val Ser
            180                 185                 190

Asp Asn Arg Leu Ser Gly Met Ile Pro Ala Ser Leu Ser Arg Phe Pro
        195                 200                 205

Ser Ser Gly Phe Val Asn Asn Glu Glu Leu Cys Gly Ser Pro Leu Gln
    210                 215                 220

Ser Cys Asn Glu Ser Asn Asn Ala Ser Ala Ser Asn Pro Tyr Met
225                 230                 235                 240

Ala Ser Ser Pro Ser Met Ile Ser Gly Ser Leu Pro Val His Arg Asn
                245                 250                 255

Asn Ser Ser Thr Gln Leu Ser Lys Gly Asp Ile Ile Ala Ile Val Val
            260                 265                 270

Gly Asp Val Ala Val Leu Ser Leu Ile Gly Cys Val Ile Phe Cys Tyr
        275                 280                 285

Tyr Trp Lys Lys Lys Gly Val Lys Gln Lys Lys Pro Lys Pro Lys Pro
    290                 295                 300

Ala Gln Arg Cys Pro Thr Asp Arg Leu Ala Val His Ser Ser Asp Gln
305                 310                 315                 320

Cys Pro Asn Asn Gln Ser Ile Thr Ala Gly Lys Cys Lys Leu Ile Phe
                325                 330                 335

Phe Asp Asp Gly Arg Pro Phe Glu Leu Glu His Leu Leu Arg Ala Ser
            340                 345                 350

Ala Glu Met Leu Gly Lys Gly Asn Phe Gly Ser Ala Tyr Lys Ala Ile
        355                 360                 365

Met Glu Asp Gly Ser Val Val Ala Val Lys Arg Leu Lys Asp Leu Tyr
    370                 375                 380

Gly Ile Gly Arg Lys Glu Phe Glu Gln His Met Glu Leu Met Gly Ser
385                 390                 395                 400

Leu Arg His Gln Asn Val Val Asn Leu Arg Ala Tyr Tyr Phe Ala Arg
                405                 410                 415

Asp Glu Lys Leu Leu Val Tyr Asp Tyr Met Pro Asn Gly Ser Leu Tyr
            420                 425                 430

Ala Leu Leu His Gly Ser Arg Gly Pro Gly Arg Thr Pro Leu Asp Trp
        435                 440                 445

Thr Thr Arg Met Lys Ile Ala Leu Gly Ala Ala Lys Gly Leu Ala Phe
    450                 455                 460

Ile His Ser His Cys Lys Ser Pro Lys Ile Gly His Gly Asn Ile Lys
465                 470                 475                 480

Ser Ser Asn Ile Leu Leu Asp Arg Asn Gly Asn Ala Cys Ile Ser Asp
                485                 490                 495

Phe Gly Leu Ala Leu Leu Val Ser Pro Ser Val Ala Ala Ser Arg Met
            500                 505                 510

Val Gly Tyr Thr Ala Pro Glu Gln Ala Ala Thr Lys Lys Ile Ser Gln
        515                 520                 525

Lys Ala Asp Val Tyr Ser Phe Gly Val Leu Leu Leu Glu Met Leu Thr
    530                 535                 540

Gly Lys Ala Pro Val Gln Ala His Met Gln Glu Asp Tyr His Ser Ala
545                 550                 555                 560

Ile Asp Leu Pro Arg Trp Val Gln Ser Ile Val Pro Glu Glu Trp Thr
                565                 570                 575

Ser Glu Val Phe Asp Ile Glu Leu Met Arg Phe Lys Asn Ile Glu Glu
            580                 585                 590
```

```
Glu Leu Val Ser Met Leu Gln Ile Ala Leu Leu Cys Ala Ser Gln Ser
        595                 600                 605
Pro Gln Gln Arg Pro Lys Met Ser His Val Arg Val Ile Gln Asp
        610                 615                 620
Ile Arg Gly Asp His His Ser Pro Ser Met Gln Asn Ser Leu Ser Gln
625                 630                 635                 640
Ser Pro Ser Met Gln Glu Pro Gly His Ser Ile Ser Asp Ser Pro Ser
                645                 650                 655
Val Ser Glu Asp Ser Gly Ile Arg Gly Leu
            660                 665

<210> SEQ ID NO 69
<211> LENGTH: 690
<212> TYPE: PRT
<213> ORGANISM: Eucalyptus grandis

<400> SEQUENCE: 69

Met Gly Phe Ala Ser Leu Arg Ser Gln Cys Leu Phe Phe Leu Leu
 1               5                  10                  15
Trp Val Phe Ile Phe Ala Ser Arg Ser Asp Val Leu Val Ser Ala
            20                  25                  30
Ala Thr Ser Ala Glu Leu Arg Ala Leu Met Asp Met Lys Ala Ser Leu
            35                  40                  45
Asp Pro Glu Ser Arg Tyr Leu Ser Ser Trp Thr Val Asp Gly Asp Pro
 50                  55                  60
Cys Asp Gly Ser Phe Gln Gly Val Cys Cys Asp Asp Glu Gly Arg Val
 65                  70                  75                  80
Ala Asn Val Ser Leu Gln Gly Arg Arg Leu Thr Gly Arg Leu Ser Pro
                85                  90                  95
Ala Ile Ala Gly Leu Thr His Leu Thr Gly Leu Tyr Leu His Tyr Asn
                100                 105                 110
Ser Leu Cys Gly Glu Ile Pro Arg Glu Leu Gly Asn Leu Ser Ala Leu
            115                 120                 125
Ser Asp Leu Tyr Leu Asn Met Asn Asn Leu Ser Gly Gln Ile Pro Pro
130                 135                 140
Glu Met Ala Asp Val Ala Ser Leu Gln Val Met Gln Leu Ser Tyr Asn
145                 150                 155                 160
Gln Leu Thr Gly Ser Ile Pro Thr Lys Leu Gly Ser Leu Lys Lys Leu
                165                 170                 175
Ser Val Leu Ala Leu Gln Ser Asn Gln Leu Thr Gly Ala Ile Pro Ala
            180                 185                 190
Ser Leu Gly Asp Leu Gly Thr Leu Thr Arg Leu Tyr Leu Ser Phe Asn
        195                 200                 205
Arg Leu Phe Gly Ser Ile Pro Met Lys Ile Ala Asp Leu Pro Leu Leu
210                 215                 220
Glu Val Leu Asp Val Gln Asn Asn Thr Leu Ser Gly Asn Val Pro Pro
225                 230                 235                 240
Ala Leu Lys Arg Leu Asn Glu Gly Phe Leu Tyr Glu Asn Asn Phe Asp
                245                 250                 255
Leu Cys Gly Thr Gly Phe Leu Ser Leu Arg Thr Cys Asn Ala Leu Glu
            260                 265                 270
Gly Arg Lys Pro Ser Gln Pro Gln Pro Tyr Gly Ala Ala Thr Thr Val
        275                 280                 285
Pro Ser Thr Ser Ile Pro Glu Thr Ala Asn Val Val Leu Pro Cys Asn
```

```
                  290                 295                 300
Leu Thr Glu Cys Ser Ser Leu Pro Lys Ser Ala His Pro Ser Ala Leu
305                 310                 315                 320

Ile Gly Ser Ile Leu Ala Thr Val Ala Leu Ser Ala Ile Gly Phe Leu
                325                 330                 335

Leu Phe Thr His Tyr Arg Arg Arg Lys Gln Lys Leu Gly Phe Ser Ala
                340                 345                 350

Glu Val Cys Asp Gly His Leu Ser Thr Asp Gln Pro Lys Ser Ala Tyr
                355                 360                 365

Lys Lys Asn Gly Ser Pro Leu Ala Ser Leu Glu Tyr Ser Asn Gly Trp
                370                 375                 380

Asp Pro Leu Ala Asp Ala Arg Ile Phe Asn Glu Phe Ser Glu Glu Ala
385                 390                 395                 400

Phe Gln Ser Phe Arg Phe Asn Leu Glu Glu Val Glu Ser Ala Thr Gln
                405                 410                 415

Tyr Phe Ser Glu Leu Asn Val Leu Gly Lys Ser Asn Phe Ser Thr Thr
                420                 425                 430

Tyr Arg Gly Ile Leu Arg Asp Gly Ser Val Val Ser Ile Lys Cys Ile
                435                 440                 445

Asn Lys Thr Ser Cys Lys Ala Asp Glu Ser Glu Phe Leu Lys Gly Leu
                450                 455                 460

Asn Met Leu Thr Ser Leu Arg His Glu Asn Leu Val Arg Leu Arg Gly
465                 470                 475                 480

Phe Cys Cys Ser Thr Ala Arg Gly Glu Cys Phe Leu Ile Tyr Asp Tyr
                485                 490                 495

Val Pro Asn Gly Thr Leu Leu Ser Phe Leu Asp Leu Glu Glu Gly Asp
                500                 505                 510

Ser Gly Thr Leu Glu Trp Ser Thr Arg Val Ser Ile Val Lys Gly Ile
                515                 520                 525

Ala Lys Gly Ile Ala Tyr Leu His Ala His Lys Pro Asn Lys Ala Pro
530                 535                 540

Leu Leu His Gln Asn Ile Ser Ala Asp Lys Val Leu Ile Asp Gln Arg
545                 550                 555                 560

Phe Asn Pro Leu Leu Tyr Gln Ser Gly Leu His Arg Leu Leu Thr Asn
                565                 570                 575

Asp Val Val Phe Ser Leu Leu Lys Ala Ser Ala Met Gly Tyr Leu
                580                 585                 590

Ala Pro Glu Tyr Met Ser Thr Gly Arg Phe Thr Glu Lys Ser Asp Val
                595                 600                 605

Tyr Ala Phe Gly Met Ile Val Phe Gln Ile Leu Ser Gly Lys Gln Lys
                610                 615                 620

Val Asp His Ser Met Arg Leu Ala Ala Glu Ser Cys Arg Phe Gln Glu
625                 630                 635                 640

Phe Ile Asp Ala Asn Ile His Gly Arg Phe Phe Glu Tyr Glu Ala Ala
                645                 650                 655

Lys Leu Ala Lys Ile Ala Ser Leu Cys Thr Asn Glu Ser Pro Tyr Asp
                660                 665                 670

Arg Pro Ser Met Asp Ala Val Ile His Glu Leu Ser Asn Cys Ser Ser
                675                 680                 685

Cys Leu
    690
```

<210> SEQ ID NO 70

```
<211> LENGTH: 655
<212> TYPE: PRT
<213> ORGANISM: Pinus radiata

<400> SEQUENCE: 70
```

| | | | | | | | | | | | | | | |
|---|---|---|---|---|---|---|---|---|---|---|---|---|---|---|
|Met|Tyr|Trp|Ser|Gln|Met|Gly|Asn|Ile|Arg|Gln|Leu|Phe|Asn|Gly|Phe|
|1| | | |5| | | | |10| | | | |15|

Met Tyr Trp Ser Gln Met Gly Asn Ile Arg Gln Leu Phe Asn Gly Phe
1               5                   10                  15

Phe Met Leu Val Leu Val Val Ala Val Lys Gly Glu Pro Thr Gly
            20                  25                  30

Asp Lys Gln Ala Leu Leu Asp Phe Leu Ser Lys Val Pro His Gly Arg
        35                  40                  45

Arg Leu Asn Trp Asn Ala Ser Ser Ala Cys Thr Trp Val Gly Val
50                  55                  60

Thr Cys Asn Ser Asn Lys Asp Arg Ile Trp Glu Val Arg Leu Pro Gly
65                  70                  75                  80

Val Gly Leu Phe Gly Pro Ile Pro Pro Gly Thr Leu Gly Arg Leu Thr
                85                  90                  95

Glu Leu Arg Val Leu Ser Leu Arg Ser Asn Leu Leu Thr Gly Ser Leu
            100                 105                 110

Pro Ser Asp Leu Ala Asn Ala Lys Ala Leu Arg Ser Ile Tyr Leu Gln
        115                 120                 125

His Asn Leu Phe Ser Gly Pro Leu Pro Pro Phe Leu Ser Gln Trp Gly
    130                 135                 140

Arg Leu Ser Arg Leu Asp Leu Ser Phe Asn Arg Leu Asn Gly Ser Ile
145                 150                 155                 160

Pro Phe Ser Leu Asn Asn Leu Thr His Leu Thr Gly Leu Leu Leu Gln
                165                 170                 175

Asn Asn Ser Leu Ser Gly Ser Ile Pro Asn Leu Asn Ile Gln Asn Leu
            180                 185                 190

Thr Leu Leu Ser Val Ala Asn Asn Gln Leu Asn Gly Ser Ile Pro Arg
        195                 200                 205

Ser Leu Gln Lys Phe Pro Lys Thr Ser Phe Gln Gly Asn Ala Gln Leu
    210                 215                 220

Cys Gly Val Pro Leu Lys Leu Cys Lys Ser Phe Phe Pro Ser Pro Ser
225                 230                 235                 240

Pro Ser Pro Asn Gly Ser Ala Val Pro Arg Arg Ser Lys Lys Ser Lys
                245                 250                 255

Leu Ser Thr Gly Val Val Val Ala Ile Ile Val Gly Ala Val Ala Val
            260                 265                 270

Leu Phe Leu Leu Leu Ala Cys Leu Phe Leu Cys Cys Val Arg Lys His
        275                 280                 285

Arg Gly Glu Ser Ala Thr Glu Lys Pro Gln Lys Asp Glu Arg Thr Thr
    290                 295                 300

Val Glu Lys Gly Gly Pro Ser Lys Glu Glu Tyr Met Gly Thr Ala Gln
305                 310                 315                 320

Glu Thr Glu Arg Asn Lys Leu Val Phe Phe Glu Gly Ser Gln Tyr Thr
                325                 330                 335

Phe Asp Leu Glu Asp Leu Leu Arg Ala Ser Ala Glu Val Leu Gly Lys
            340                 345                 350

Gly Ser Val Gly Thr Ala Tyr Lys Ala Val Leu Glu Asp Gly Thr Thr
        355                 360                 365

Val Val Val Lys Arg Leu Lys Asp Val Ala Val Asn Arg Arg Asp Phe
    370                 375                 380

Glu Gln Gln Met Glu Leu Val Gly Arg Ile Arg His Arg Asn Leu Val

-continued

```
385                 390                 395                 400

Pro Leu Arg Ala Phe Tyr Phe Ser Lys Asp Glu Lys Leu Leu Val Tyr
                405                 410                 415

Asp Tyr Met Pro Ala Gly Ser Leu Ser Ala Leu Leu His Gly Ser Arg
                420                 425                 430

Gly Ser Gly Arg Thr Pro Leu Asp Trp Glu Thr Arg Met Arg Ile Ala
                435                 440                 445

Leu Gly Ala Ala Arg Gly Ile Ser His Ile His Glu Glu Gly Gly Gly
                450                 455                 460

Lys Phe Thr His Gly Asn Ile Lys Ser Ser Asn Val Leu Leu Thr Ser
465                 470                 475                 480

Asp Leu Asp Gly Cys Val Ser Asp Phe Gly Leu Val Pro Leu Phe Ser
                485                 490                 495

Ala Ala Ala Ala Ala Asn Arg Ile Ala Gly Tyr Arg Ala Pro Glu Val
                500                 505                 510

Ile Glu Thr Arg Lys Val Thr Gln Lys Ser Asp Val Tyr Ser Phe Gly
                515                 520                 525

Val Leu Leu Leu Glu Leu Thr Gly Lys Ala Pro Asn Gln Ala Ser
                530                 535                 540

Leu Asn Asp Glu Gly Ile Asp Leu Pro Arg Trp Val Gln Ser Val
545                 550                 555                 560

Arg Glu Glu Trp Thr Ala Glu Val Phe Asp Val Glu Leu Met Arg Tyr
                565                 570                 575

Gln Asn Ile Glu Glu Met Val Gln Leu Leu Gln Ile Ala Met Ala
                580                 585                 590

Cys Val Ala Thr Val Pro Asp Gln Arg Pro Arg Met Gln Asp Val Val
                595                 600                 605

Lys Met Ile Glu Asp Met Arg Gln Phe Glu Thr Asp Glu Gly Asn Arg
                610                 615                 620

Gln Ser Ser Asp Asp Lys Ser Lys Glu Ser Asn Gly Gln Thr Pro Pro
625                 630                 635                 640

Gln Gln Ala Thr Pro Glu Ala Arg Thr Pro Thr Ala Arg Thr Pro
                645                 650                 655

<210> SEQ ID NO 71
<211> LENGTH: 630
<212> TYPE: PRT
<213> ORGANISM: Pinus radiata

<400> SEQUENCE: 71

Met Gln Gln Pro Tyr Val Val Leu Ala Leu Leu Trp Met Leu Leu Leu
1               5                   10                  15

His His Pro Leu Trp Arg Val Phe Ala Asn Thr Glu Gly Asp Ala Leu
                20                  25                  30

His Ser Leu Arg Ser Asn Leu Leu Asp Pro Asn Asn Val Leu Gln Ser
                35                  40                  45

Trp Asp Pro Thr Leu Val Asn Pro Cys Thr Trp Phe His Val Thr Cys
                50                  55                  60

Asn Asn Asp Asn Ser Val Ile Arg Val Asp Leu Gly Asn Ala Gln Leu
65              70                  75                  80

Ser Gly Ser Leu Val Pro Gln Leu Gly Leu Leu Asn Asn Leu Gln Tyr
                85                  90                  95

Leu Glu Leu Tyr Ser Asn Asn Ile Ser Gly Pro Ile Pro Ser Asp Leu
                100                 105                 110
```

```
Gly Asn Leu Thr Asn Leu Val Ser Leu Asp Leu Tyr Leu Asn Asn Phe
            115                 120                 125

Thr Gly Leu Ile Pro Glu Ser Leu Gly Lys Leu Ser Arg Leu Arg Phe
        130                 135                 140

Leu Arg Leu Asn Asn Asn Ser Leu Val Gly Arg Ile Pro Met Ser Leu
145                 150                 155                 160

Thr Thr Ile Thr Ala Leu Gln Val Leu Asp Leu Ser Asn Asn Asn Leu
                165                 170                 175

Thr Gly Glu Val Pro Ala Asn Gly Ser Phe Ser Leu Phe Thr Pro Ile
            180                 185                 190

Ser Phe Gly Gly Asn Gln Tyr Leu Cys Gly Pro Val Ala Gln Lys Pro
        195                 200                 205

Cys Pro Gly Ser Pro Pro Phe Ser Pro Pro Pro Phe Val Pro Pro
    210                 215                 220

Pro Pro Val Ala Gly Ser Asn Gly Ala Arg Val Gln Ser Ser Ser Ser
225                 230                 235                 240

Thr Gly Ala Ile Ala Gly Gly Val Ala Ala Gly Ala Ala Leu Leu Phe
                245                 250                 255

Ala Ala Pro Ala Ile Gly Phe Ala Trp Trp Arg Arg Arg Lys Pro Gln
            260                 265                 270

Glu His Phe Phe Asp Val Pro Ala Glu Glu Asp Pro Glu Val His Leu
        275                 280                 285

Gly Gln Leu Lys Arg Phe Ser Leu Arg Glu Leu Gln Val Ala Thr Asp
    290                 295                 300

Gly Phe Ser Asn Arg Asn Ile Leu Gly Arg Gly Gly Phe Gly Lys Val
305                 310                 315                 320

Tyr Lys Gly Arg Leu Ala Asp Gly Ser Leu Val Ala Val Lys Arg Leu
                325                 330                 335

Lys Glu Glu Arg Thr Pro Gly Gly Glu Leu Gln Phe Gln Thr Glu Val
            340                 345                 350

Glu Met Ile Ser Met Ala Val His Arg Asn Leu Leu Arg Leu Arg Gly
        355                 360                 365

Phe Cys Met Thr Pro Thr Glu Arg Leu Leu Val Tyr Pro Tyr Met Ala
    370                 375                 380

Asn Gly Ser Val Ala Ser Cys Leu Arg Glu Arg Ala Gln Asn Asp Pro
385                 390                 395                 400

Pro Leu Asp Trp Pro Thr Arg Lys Arg Ile Ala Leu Gly Ser Ala Arg
                405                 410                 415

Gly Leu Ser Tyr Leu His Asp His Cys Asp Pro Lys Ile Ile His Arg
            420                 425                 430

Asp Val Lys Ala Ala Asn Ile Leu Leu Asp Glu Glu Tyr Glu Ala Val
        435                 440                 445

Val Gly Asp Phe Gly Leu Ala Lys Leu Met Asp Tyr Lys Asp Thr His
    450                 455                 460

Val Thr Thr Ala Val Arg Gly Thr Ile Gly His Ile Ala Pro Glu Tyr
465                 470                 475                 480

Leu Ser Thr Gly Lys Ser Ser Glu Lys Thr Asp Val Phe Gly Tyr Gly
                485                 490                 495

Ile Met Leu Leu Glu Leu Ile Thr Gly Gln Arg Ala Phe Asp Leu Ala
            500                 505                 510

Arg Leu Ala Asn Asp Asp Val Met Leu Leu Asp Trp Val Lys Gly
        515                 520                 525

Leu Leu Lys Glu Arg Arg Leu Asp Met Leu Val Asp Pro Asp Leu Lys
```

```
              530                 535                 540
Asn Asn Tyr Val Glu Ala Glu Val Glu Gln Leu Ile Gln Val Ala Leu
545                 550                 555                 560

Leu Cys Thr Gln Gly Ser Pro Met Asp Arg Pro Lys Met Ser Glu Val
                565                 570                 575

Val Arg Met Leu Glu Gly Asp Gly Leu Ala Glu Arg Trp Glu Glu Trp
                580                 585                 590

Gln Lys Val Glu Val Arg Ser Gln Glu Val Glu Leu Val Pro His
            595                 600                 605

Arg Asn Ser Glu Trp Ile Val Asp Ser Thr Asp Asn Leu His Ala Val
                610                 615                 620

Glu Leu Ser Gly Pro Arg
625                 630

<210> SEQ ID NO 72
<211> LENGTH: 910
<212> TYPE: PRT
<213> ORGANISM: Pinus radiata

<400> SEQUENCE: 72

Met Leu Leu Leu Ala Thr Leu Ser Phe Ile Leu Phe Leu Asn Pro Phe
1               5                   10                  15

Ala Phe Ser Thr Pro Ile Ala His Phe Pro His Pro Pro Arg Leu
                20                  25                  30

Thr Asn Ala Ser Asp Gln His Ala Leu Leu Ala Phe Lys Ser Ala Ile
            35                  40                  45

Thr Tyr Asp Pro Ser Gln Ser Leu Ala Thr Ser Trp Leu Pro Asn Val
50                  55                  60

Ser Phe Cys Gln Trp Thr Gly Ile Ile Cys Ser Arg Arg Gln Arg
65                  70                  75                  80

Val Ile Ser Leu Asn Val Ser Ser Met Gly Leu Gln Gly Thr Ile Ser
                85                  90                  95

Pro Leu Leu Ala Asn Leu Ser Phe Leu Thr Val Leu Asp Leu His Asn
                100                 105                 110

Asn Ser Phe Asp Cys His Ile Pro Tyr Gln Leu Gly Thr Leu Phe Arg
            115                 120                 125

Leu Lys Met Leu Arg Leu Ser Lys Asn Gln Leu Gln Gly Ser Ile Pro
130                 135                 140

Pro Thr Leu Ala Asn Cys Arg Ser Leu Arg Asn Leu Thr Leu Ser Phe
145                 150                 155                 160

Asn Asn Leu Thr Gly Asn Ile Pro Pro Gln Leu Cys Leu Leu Pro Asn
                165                 170                 175

Leu Ile Cys Met Ser Leu Gly Ile Asn Asn Leu Thr Gly Thr Ile Pro
            180                 185                 190

Asp Cys Leu Gly Asn Ile Ser Ser Leu Gln Tyr Leu Ser Leu Ser Gln
            195                 200                 205

Gly Asn Leu Gln Gly Ser Val Pro Ser Glu Leu Gly Arg Leu Ser Gln
            210                 215                 220

Leu Ile Val Leu Asp Leu Phe Gly Asn His Leu Thr Gly Cys Ile Pro
225                 230                 235                 240

Ser Ser Leu Ser Asn Cys Thr Asn Leu Glu Leu Leu Asp Ile Gly Asp
                245                 250                 255

Asn Gln Leu Val Gly His Ile Pro Ser His Leu Cys Thr Lys Lys Thr
                260                 265                 270
```

-continued

```
Thr Gln Leu Met Tyr Leu Arg Leu Gly Ala Asn Gln Leu Ser Gly Ser
        275                 280                 285

Val Pro Ser Ser Leu Phe Asn Cys Thr Lys Leu Gln Glu Ile Ala Leu
    290                 295                 300

Pro Tyr Asn Gln Leu Ser Gly Ile Val Pro Met Glu Leu Gly Lys Leu
305                 310                 315                 320

Thr His Leu Gln Arg Leu Phe Phe Gly Gly Asn Tyr Phe Ile Ser Gly
            325                 330                 335

Asn Thr Met Arg Cys Pro Ile Leu Thr Ala Leu Ser Asn Cys Ser Asp
                340                 345                 350

Leu Gln Tyr Val Asp Leu Ser Glu Asn Asn Phe Thr Gly Gln Leu Pro
        355                 360                 365

Phe Ser Ile Gly His Leu Ser Lys Lys Leu Tyr His Leu Asp Leu Gly
    370                 375                 380

Ser Asn Glu Leu Ala Gly Glu Ile Pro Pro Ala Ile Gly Asn Leu Ser
385                 390                 395                 400

Ser Leu Thr Phe Leu Asn Leu Gly Arg Asn Tyr Phe Thr Gly Ser Ile
            405                 410                 415

Pro Ser Ser Leu Ile Met Leu Gln Lys Leu Glu Arg Leu Tyr Met Asp
                420                 425                 430

Ser Asn Asn Leu Gln Gly Asn Ile Pro Met Glu Ile Gly Gln Leu Lys
        435                 440                 445

Ser Leu Gly Leu Leu Tyr Leu Ser Gly Asn Asn Leu Ser Gly Lys Ile
    450                 455                 460

Pro Asp Phe Val Ala Asn Leu Gln Gln Leu Arg Tyr Leu Tyr Leu Asn
465                 470                 475                 480

His Asn Gln Leu Ser Gly Asp Ile Asn Ala Asn Leu Gly Lys Cys Val
            485                 490                 495

Asn Leu Leu Leu Asp Leu Ser Tyr Asn Lys Leu Ser Gly His Ile
                500                 505                 510

Pro Gln Glu Leu Ala Gly Leu Ala Asn Leu Ala Phe Tyr Phe Asn Leu
        515                 520                 525

Ser Asn Asn Leu Leu Ser Gly His Val Pro Leu Glu Leu Gly Lys Phe
    530                 535                 540

Asp Met Leu Gln Ala Ile Asp Ile Ser Ala Asn Gln Ile Thr Gly Tyr
545                 550                 555                 560

Ile Pro Ser Ile Val Gly Ser Trp Lys Glu Val Ala Tyr Leu Asn Leu
            565                 570                 575

Ser Tyr Asn Ala Leu Glu Gly Pro Ile Pro Val Ser Ile Ser Glu Leu
        580                 585                 590

Leu Ser Leu Gln Asp Leu Asp Leu Ser Ser Asn Asn Leu Ser Gly Gly
    595                 600                 605

Ile Pro Ile Ser Leu Ala Asn Leu Thr Met Leu His His Leu Asn Phe
610                 615                 620

Ser Phe Asn Lys Leu Ser Gly Glu Val Pro Lys Glu Gly Val Phe Lys
625                 630                 635                 640

Asn Ile Gly Ala Thr Ala Phe Met Gly Asn Leu Gly Leu Cys Gly Pro
            645                 650                 655

Trp Val Asn Leu Pro Pro Cys Tyr Ala His Lys His Lys Ser Val Leu
                660                 665                 670

Asn Leu Lys Arg Val Ile Ile Leu Val Val Val Ala Ile Val Val
        675                 680                 685

Leu Cys Leu Phe Leu Ala Ile Leu Trp Arg Lys Asn Cys Arg Arg Asn
```

-continued

```
            690                 695                 700
Ile Gln Arg Asp Ile Gly Pro Ser Leu Asn Val Gly His Arg Arg Ile
705                 710                 715                 720

Ser Tyr Ala Glu Leu Val Ile Ala Thr Asn Glu Phe Ser Asp Ala Asn
                725                 730                 735

Leu Leu Gly Ile Gly Ser Phe Gly Lys Val Tyr Lys Gly Ile Leu Asn
                740                 745                 750

Asp Gly Thr Met Val Ala Val Lys Leu Leu Asn Leu Gln Asn Glu Gly
                755                 760                 765

Ala Gln Lys Ser Phe Asp Arg Glu Cys Lys Val Leu Gly Arg Val Arg
770                 775                 780

His Arg Asn Leu Ile Arg Val Ile Thr Cys Tyr Ser Asp Leu Gln Ile
785                 790                 795                 800

Lys Ala Leu Ile Phe Pro Leu Met Pro Lys Gly Ser Leu Glu Lys Trp
                805                 810                 815

Leu Tyr Pro Asp Asp Gly Glu Gln Ser Cys Leu Asn Leu Ile Gln Arg
                820                 825                 830

Leu Asn Ile Ala Ile Asp Ile Ala Gln Gly Met Thr Tyr Leu His His
                835                 840                 845

His Cys Phe Val Gln Val Ile His Cys Asp Leu Lys Pro Asn Asn Val
850                 855                 860

Leu Leu Gly Glu Asp Met Thr Ala Tyr Leu Ile Asp Phe Gly Ile Ala
865                 870                 875                 880

Thr Ile Cys Phe Ala Asn Asn Glu Asp Gly Ala Leu Thr Ser Thr Asn
                885                 890                 895

Ala Leu Lys Gly Ser Thr Gly Tyr Ile Pro Pro Gly Ile Ile
                900                 905                 910

<210> SEQ ID NO 73
<211> LENGTH: 947
<212> TYPE: PRT
<213> ORGANISM: Pinus radiata

<400> SEQUENCE: 73

Met Arg Tyr Ser Trp Thr Cys Ser Pro Phe Leu Ser Leu Leu Phe Ile
1               5                   10                  15

Leu Ser Cys Leu Asp Ser Gly Ile Cys Leu Asp Asn Gln Gln Thr Gln
                20                  25                  30

Val Met Lys Lys Leu Ser Ser Tyr Thr Pro Ser Trp Thr Thr Val Lys
                35                  40                  45

Ser Asp Asn Pro Cys Gly Trp Ser Gly Val Asn Cys Thr Ala Glu Glu
50                  55                  60

Ser Asn Val Thr Glu Leu His Met Ser Gly Phe Arg Met Lys Gly Asn
65                  70                  75                  80

Ala Trp Gln Thr Ile Cys Lys Leu Gln Ala Leu Gln Val Leu Asp Val
                85                  90                  95

Ser Asp Asn Leu Leu Ser Thr Pro Ser Asp Asn Asp Ile Gln Ala Cys
                100                 105                 110

Thr Asn Leu Phe Ser Leu Asn Ile Ser Ser Asn Phe Leu Pro Gly Ser
                115                 120                 125

Ser Leu Pro Ser Leu Ala Pro Met Arg Lys Leu His Phe Leu Asp Val
                130                 135                 140

Ser His Asn Gly Phe Ala Gly Glu Phe Gly Pro Gln Ile Gln His Leu
145                 150                 155                 160
```

-continued

```
Thr Asp Leu Arg Val Leu Asn Leu Thr Tyr Asn Asn Phe Ser Gly Pro
                165                 170                 175

Ile Pro Ser Phe Leu Gly Asn Leu Thr Thr Leu Glu Lys Ile Asp Phe
            180                 185                 190

Ser Gln Asn Tyr Phe Glu Gly Glu Phe Pro Lys Glu Leu Val Arg Cys
        195                 200                 205

Thr Ser Leu Thr Tyr Leu Asp Leu Ser Phe Asn Arg Leu Thr Gly Gln
    210                 215                 220

Ile Pro Asp Asn Ile Ser Asn Leu Ile His Leu Glu Thr Leu Ile Leu
225                 230                 235                 240

Ser Ser Asn Asn Leu Thr Gly Thr Ile Pro Lys Thr Leu Asp Arg Leu
                245                 250                 255

Val Asn Leu Thr His Phe Ala Ser Asn Lys Asn Gln Leu Ile Gly Arg
            260                 265                 270

Ile Pro Val Gln Leu Ala Lys Leu Thr Glu Leu His Phe Leu Asp Leu
        275                 280                 285

Ser Tyr Asn Gly Leu Asn Glu Thr Ile Pro Pro Glu Leu Phe Ala Leu
    290                 295                 300

Ser Asn Leu Gln Thr Leu Asp Leu Thr Lys Asn Leu Leu Thr Gly Glu
305                 310                 315                 320

Ile Pro Gln Asn Phe Ser Arg Lys Leu Ile Arg Leu Arg Ile Gly Gln
                325                 330                 335

Asn Leu Leu Lys Gly Asn Ile Pro Leu Thr Ile Gly Asn Trp Ser Asn
            340                 345                 350

Leu Thr Tyr Leu Glu Met Asn Asp Asn Ser Leu Asp Gly Gln Ile Pro
        355                 360                 365

Gln Gln Leu Val Asn Cys Ile Lys Leu Gln Leu Leu Asp Leu Gly Asn
    370                 375                 380

Asn Asn Leu Ser Gly Ser Leu Thr Asn Gln Leu Pro Ser Leu Leu Gln
385                 390                 395                 400

Leu Gln Val Leu Lys Leu His Asn Asn Asn Phe Val Gly Ser Ile Pro
                405                 410                 415

Tyr Ile Leu Ser Ser Phe Ser Asn Leu Ser Tyr Val Asp Leu Ser Asp
            420                 425                 430

Asn Thr Leu Asn Gly Ser Ile Pro Ser Asn Ile Phe Asn Leu Ser Lys
        435                 440                 445

Leu Gln Asn Leu Arg Leu Gln Asn Asn Lys Leu Thr Gly Ala Ile Pro
    450                 455                 460

Asn Thr Val Gly Gly Ser Gln Val Leu Leu Glu Leu Gln Leu Gly Gly
465                 470                 475                 480

Asn Asn Leu Thr Gly Thr Met Pro Leu Glu Ile Gly Phe Val Arg Lys
                485                 490                 495

Leu Gln Ile Gln Leu Asn Leu Ser Cys Asn Ser Leu Glu Gly Glu Ile
            500                 505                 510

Pro Asn Thr Leu Ser Gly Leu Tyr Met Leu Glu Ile Leu Asp Leu Ser
        515                 520                 525

Asn Asn Lys Leu Thr Gly Glu Val Pro Gly Ser Leu Thr Ala Met Leu
    530                 535                 540

Ser Leu Thr Leu Leu Asn Ile Ser Asn Asn Ser Leu Thr Gly Val Leu
545                 550                 555                 560

Pro Lys Phe Pro Asn Ser Thr Ser Ala Leu Ile Ile Asp Thr Gly
                565                 570                 575

Asn Pro Gly Leu Thr Ala Gly Gln Asn Gly Ser Ala Pro Ala Ala Ser
```

```
                    580                 585                 590
    Ala Arg Lys Lys Ile Ser Ala Ile Leu Ile Ile Gly Val Ala Val Ala
                595                 600                 605

Gly Ala Val Phe Ala Ile Val Ala Val Gly Leu Phe Ile Val Ala Ser
                610                 615                 620

Lys Tyr Phe Gly Arg Gly Asp Gln Gln Met Pro Glu Val Gln Leu Ala
    625                 630                 635                 640

Arg Lys Ile Glu Gly His Phe Ile His Pro Asp Ser Ile His Arg Leu
                    645                 650                 655

Arg Ile Asp Phe Glu Lys Gly Val Glu Ala Thr Leu Asp Pro Ala Asn
                660                 665                 670

Val Phe Leu Lys Asn Lys Phe Ser Thr Tyr Tyr Lys Ala Val Met Pro
                675                 680                 685

Ser Gly Ile Ser Tyr Ser Val Lys Lys Leu Asn Trp Ser Asp Arg Ile
                690                 695                 700

Phe Lys Ser Gly Ser Tyr Arg Lys Leu Gly Ala Glu Leu Glu Lys Gln
    705                 710                 715                 720

Gly Lys Leu Arg His Pro Asn Ile Leu Thr Pro Leu Ala His Val Leu
                    725                 730                 735

Asp Thr Asp Ser Ala Tyr Leu Phe Tyr Glu Tyr Val His Lys Gly Ser
                740                 745                 750

Leu Ser Glu Phe Leu His Thr Ser Asn Val Ser Val Leu Asp Trp Pro
                755                 760                 765

Ser Arg Cys Arg Ile Ala Ile Gly Val Ala Gln Gly Leu Ala Phe Leu
                770                 775                 780

His Gly Cys Gln His Pro Ile Phe His Leu Asp Leu Thr Thr Lys Asn
    785                 790                 795                 800

Ile Leu Leu Lys Ser Leu Thr Glu Pro Gln Ile Gly Asp Ile Glu Leu
                    805                 810                 815

Cys Lys Ile Val Asp Pro Ser Lys Ser Thr Gly Ser Ile Ser Ala Ile
                820                 825                 830

Ala Gly Ser Val Gly Tyr Val Pro Pro Glu Tyr Ala Tyr Thr Met Arg
                835                 840                 845

Val Thr Ala Ala Gly Asn Val Tyr Ser Phe Gly Val Ile Leu Leu Glu
                850                 855                 860

Leu Leu Thr Gly Arg Thr Pro Ile Thr Ser Gly Met Asp Leu Ala Lys
    865                 870                 875                 880

Trp Val Gln Ser Thr Leu Ser Gly Glu Glu Thr Trp Glu Gln Ile Leu
                    885                 890                 895

Asp Thr Gly Ile Arg Asn Phe Ser Val Gln Ile Gln Asn Glu Met Ile
                900                 905                 910

Ala Met Leu Lys Val Ala Leu Ser Cys Val Ser Ser Ser Pro Glu Ser
                915                 920                 925

Arg Pro Lys Met Arg Asn Val Val Gly Met Leu Gln Met Val Arg Gln
                930                 935                 940

Val Ala Glu
    945

<210> SEQ ID NO 74
<211> LENGTH: 638
<212> TYPE: PRT
<213> ORGANISM: Pinus radiata

<400> SEQUENCE: 74
```

-continued

```
Met His Phe Lys Ile Leu Phe Asp Ala Lys Glu Lys Ile Lys Ser
 1               5                   10                  15

Ser Phe Asp Met Leu Thr Ala Phe Leu Val Leu Cys Phe Thr Thr Thr
                20                  25                  30

Ala Ala Ser Ala Thr Gln Leu Ser Pro Ser Gly Leu Asn Tyr Glu Val
            35                  40                  45

Ala Ala Leu Met Ala Ile Lys Asn Ser Leu Asn Asp Pro His Asn Val
 50                  55                  60

Leu Glu Asn Trp Asp Ile Asn Ser Val Asp Pro Cys Gly Trp Arg Met
65                   70                  75                  80

Val Thr Cys Thr Leu Glu Gly Ser Val Ser Ile Leu Gly Ile Gln Cys
                85                  90                  95

Gln Asn Leu Ser Gly Ser Leu Ser Pro Ser Ile Arg Asn Leu Thr Asn
                100                 105                 110

Leu Gln Ser Val Leu Leu Gln Asn Asn Ala Ile Ser Gly Ser Ile Pro
            115                 120                 125

Ala Glu Leu Gly Lys Leu Asp Lys Leu Asp Thr Leu Asp Leu Ser Asn
130                 135                 140

Asn His Phe Asn Gly Leu Ile Pro Ser Ser Leu Gly Lys Leu Lys Asn
145                 150                 155                 160

Leu Asn Tyr Leu Arg Leu Asn Asn Asn Leu Ser Gly Pro Ile Pro
                165                 170                 175

Pro Ser Leu Ala Thr Ile Thr Gly Leu Thr Leu Leu Asp Leu Ser Cys
            180                 185                 190

Asn Asn Leu Ser Gly Ser Val Pro Arg Ile Ser Ala Arg Thr Phe Asn
            195                 200                 205

Ile Val Gly Asn Pro Leu Ile Cys Gly Pro Asn Ser Thr Tyr Lys Cys
        210                 215                 220

Pro Gly Gln Phe Pro Thr Pro Ile Pro Leu Val Val Glu Thr Pro Gln
225                 230                 235                 240

Gly Arg Val Pro Ser Arg Gln Ser Lys Thr Arg Lys Leu Ala Val Ala
                245                 250                 255

Leu Val Ala Ser Leu Gly Phe Val Phe Val Val Ser Ile Gly Leu Leu
            260                 265                 270

Leu Trp Trp Arg Lys Arg His Asn Gln Gln Ile Phe Ile Asp Val Asn
            275                 280                 285

Glu Gln His Asn Val Asp Ile Cys Leu Gly His Leu Lys Arg Phe Ser
290                 295                 300

Phe Lys Glu Leu Arg Val Ser Thr Asn Asn Phe Ser Ser Lys Asn Ile
305                 310                 315                 320

Leu Gly Val Gly Gly Tyr Gly Ile Val Tyr Lys Gly Phe Leu Gln Asp
                325                 330                 335

Gly Thr Ile Val Ala Ile Lys Arg Leu Lys Asp Gly Asn Val Gly Gly
                340                 345                 350

Gly Glu Ile Gln Phe Gln Thr Glu Val Glu Met Ile Ser Leu Ala Val
            355                 360                 365

His Arg Asn Leu Leu Arg Leu Tyr Gly Phe Cys Thr Thr Ser Arg Glu
370                 375                 380

Arg Leu Leu Val Tyr Pro Tyr Met Pro Asn Gly Ser Val Ala Ser Cys
385                 390                 395                 400

Leu Arg Asp His Ile Asn Gly Lys Leu Ala Leu Asp Trp Pro Thr Arg
                405                 410                 415

Lys Arg Ile Ala Leu Gly Ala Ala Arg Gly Leu Leu Tyr Leu His Glu
```

-continued

```
                420                 425                 430
Gln Cys Asp Pro Lys Ile Ile His Arg Asp Val Lys Ala Ala Asn Ile
            435                 440                 445
Leu Leu Asp Glu Tyr Phe Glu Ala Val Val Gly Asp Phe Gly Leu Ala
450                 455                 460
Lys Leu Leu Asp His Arg Asp Ser His Val Thr Thr Ala Val Arg Gly
465                 470                 475                 480
Thr Val Gly His Ile Ala Pro Glu Tyr Leu Ser Thr Gly Gln Ser Ser
                485                 490                 495
Glu Lys Thr Asp Val Phe Gly Phe Gly Ile Leu Leu Glu Leu Ile
            500                 505                 510
Thr Gly Gln Arg Ala Leu Asp Phe Gly Gln Ala Ala Lys Gln Lys Val
            515                 520                 525
Val Met Leu Asp Trp Val Lys Lys Leu His Gln Glu Lys Lys Leu His
    530                 535                 540
Leu Leu Ala Asp Lys Asp Leu Lys Gly Asn Phe Asp Arg Val Glu Leu
545                 550                 555                 560
Glu Glu Met Val Gln Val Ser Leu Leu Cys Thr Gln Phe Gln Pro Gly
                565                 570                 575
His Arg Pro Lys Met Cys Asp Val Leu Arg Met Leu Glu Gly Asp Gly
            580                 585                 590
Leu Thr Glu Arg Trp Glu Thr Leu Gln Lys Ile Glu Thr Pro Arg Tyr
    595                 600                 605
Arg Val Thr Glu Ile Pro Ile Thr Tyr Ser Glu Leu Val Glu Glu Asp
            610                 615                 620
Ser Ser Trp Leu Val Gln Ala Ile Glu Leu Ser Gly Pro Arg
625                 630                 635

<210> SEQ ID NO 75
<211> LENGTH: 659
<212> TYPE: PRT
<213> ORGANISM: Eucalyptus grandis

<400> SEQUENCE: 75

Met His Phe Arg Ile Leu Ala Leu Leu Gly Phe Phe Leu Ala Val
1               5                   10                  15
Leu Phe Pro Ser Ala Glu Pro Asp Leu Ala Ser Asp Arg Ala Ala Leu
                20                  25                  30
Leu Ala Leu Arg Ser Ala Val Gly Gly Arg Thr Leu Leu Trp Asn Ala
            35                  40                  45
Asn Leu Pro Ser Pro Cys Ser Trp Ala Gly Val Gln Cys Glu Gly Asn
    50                  55                  60
Arg Val Thr Ala Leu Arg Leu Pro Gly Val Ala Leu Ser Gly Gln Ile
65                  70                  75                  80
Pro Asp Gly Val Leu Gly Asn Leu Thr Gln Leu Arg Thr Leu Ser Leu
                85                  90                  95
Arg Phe Asn Ala Leu Ser Gly Thr Leu Pro Ser Asp Leu Ala Ser Cys
            100                 105                 110
Ala Asp Leu Arg Asn Leu Tyr Val Gln Gly Asn Leu Phe Ser Gly Pro
        115                 120                 125
Ile Pro Ala Ser Leu Phe Gly Leu Ser Asp Leu Val Arg Leu Asn Leu
    130                 135                 140
Ala Ser Asn Lys Phe Ser Gly Asp Phe Pro Ala Gly Phe Gly Asn Leu
145                 150                 155                 160
```

-continued

```
Thr Arg Leu Lys Thr Leu Leu Glu Asn Asn Gln Leu Ser Gly Ser
            165                 170                 175

Ile Pro Ala Asp Leu Lys Gln Leu Lys Leu Glu Gln Phe Asn Val Ser
            180                 185                 190

Asn Asn Leu Leu Asn Gly Ser Ile Pro Glu Gly Leu Gly Ala Phe Ala
            195                 200                 205

Thr Ser Ser Phe Ser Gly Asn Ser Leu Cys Gly Lys Pro Leu Ala Ser
            210                 215                 220

Cys Ser Gln Asp Ile Ala Leu Pro Ala Gly Glu Pro Ser Gly Ser Pro
225                 230                 235                 240

Gly Gln Pro Gly Gly Lys Lys Lys Leu Ser Gly Ala Val Val Ala
                245                 250                 255

Gly Ile Val Ile Gly Cys Val Phe Gly Phe Ile Phe Leu Val Ile Leu
                260                 265                 270

Leu Ile Tyr Leu Cys Arg Lys Lys Gly Ser Lys Lys Ser Arg Ser Val
            275                 280                 285

Asp Val Ala Thr Phe Lys His Gln Glu Leu Glu Ile Pro Gly Glu Lys
            290                 295                 300

Pro Val Gly Glu Val Glu Asn Gly Gly Phe Ser Asn Gly Tyr Ser Val
305                 310                 315                 320

Ala Ala Ala Ala Ala Ala Met Thr Gly Ser Gly Lys Gly Glu Val
                325                 330                 335

Asn Gly Ser Ala Gly Ala Ala Lys Lys Leu Ile Phe Phe Gly Asn
            340                 345                 350

Ser Ala Arg Ala Phe Asp Leu Glu Asp Leu Leu Arg Ala Ser Ala Glu
            355                 360                 365

Val Leu Gly Lys Gly Thr Phe Gly Thr Ala Tyr Lys Ala Val Leu Glu
            370                 375                 380

Ala Gly Ile Thr Val Ala Val Lys Arg Leu Lys Asp Val Asn Val Ala
385                 390                 395                 400

Ala Lys Glu Phe Lys Glu Lys Ile Glu Ala Val Gly Ala Met Asp His
                405                 410                 415

Gln Ser Leu Val Pro Leu Arg Ala Tyr Tyr Tyr Ser Asn Asp Glu Lys
            420                 425                 430

Leu Leu Val Tyr Asp Tyr Met Pro Met Gly Ser Leu Ser Ala Leu Leu
            435                 440                 445

His Gly Asn Lys Gly Ala Gly Arg Thr Pro Leu Asn Trp Glu Ile Arg
            450                 455                 460

Ser Ala Ile Ala Leu Gly Ala Ala Arg Gly Ile Glu Tyr Leu His Ser
465                 470                 475                 480

Gln Gly Pro Ile Val Ser His Gly Asn Ile Lys Ser Ser Asn Ile Leu
                485                 490                 495

Leu Thr Thr Ser Tyr Asp Ala Arg Val Ser Asp Phe Gly Leu Ala His
            500                 505                 510

Leu Val Gly Pro Ser Ser Thr Pro Asn His Val Ala Gly Tyr Arg Ala
            515                 520                 525

Pro Glu Val Thr Asp Pro Arg Lys Val Ser Gln Lys Ala Asp Val Tyr
            530                 535                 540

Ser Phe Gly Val Leu Leu Leu Glu Leu Leu Thr Gly Lys Ala Pro Ile
545                 550                 555                 560

His Ser Gln Leu Asn Glu Glu Gly Val Asp Leu Pro Arg Trp Val Gln
                565                 570                 575

Ser Ile Val Arg Glu Glu Trp Thr Ser Glu Val Phe Asp Leu Glu Leu
```

-continued

```
                      580                 585                 590
Leu Arg Tyr Gln Asn Ile Glu Glu Met Val Gln Leu Leu Gln Leu
                595                 600                 605

Ala Ile Asp Cys Ala Ala Gln Tyr Pro Asp Lys Arg Pro Ser Met Ser
            610                 615                 620

Glu Val Arg Ser Gln Ile Glu Glu Leu Cys His Ser Ser Ser Gln Lys
625                 630                 635                 640

Asp Arg Ala Pro Gln Leu Asp Gln Val Asn Glu Val Asn Asp Asp Thr
                645                 650                 655

Ser Ser Arg

<210> SEQ ID NO 76
<211> LENGTH: 968
<212> TYPE: PRT
<213> ORGANISM: Eucalyptus grandis

<400> SEQUENCE: 76

Met Glu Glu Ala Phe Leu Arg Leu Ile Phe Leu Val Ala Val Leu Leu
  1               5                  10                  15

Phe Gly Lys Asp Leu Gln Leu Val Phe Ser Phe Thr Asn Pro Asp Asp
             20                  25                  30

Ser Val Ala Leu Gln Ser Leu Lys Met Ser Trp Gln Asn Thr Pro Pro
         35                  40                  45

Ser Trp Glu Arg Ser Ser Asp Pro Cys Gly Leu Pro Trp Glu Gly Val
     50                  55                  60

Thr Cys Asn Ser Asn Ser Arg Val Thr Ser Leu Gly Leu Ser Thr Met
 65                  70                  75                  80

Gly Ile Lys Gly Gln Leu Ile Ser Glu Ile Ala Gly Leu Ala Glu Leu
                 85                  90                  95

Arg Ser Leu Asp Leu Ser Phe Asn Lys Glu Leu Thr Gly Pro Leu Ala
            100                 105                 110

Arg Gln Leu Gly Asn Leu Gln Lys Leu Asn Ile Leu Ile Leu Ala Gly
        115                 120                 125

Cys Ser Phe Thr Gly Ser Ile Pro Asp Glu Leu Gly Asn Leu Ala Glu
    130                 135                 140

Leu Ser Phe Leu Ala Leu Asn Ser Asn Asn Leu Thr Gly Asn Ile Pro
145                 150                 155                 160

Ala Ser Leu Gly Asn Leu Ser Lys Leu Tyr Trp Phe Asp Leu Ala Asp
                165                 170                 175

Asn Gln Leu Thr Gly Pro Ile Pro Ile Ser Thr Asp Thr Ser Pro Gly
            180                 185                 190

Leu Asp Leu Leu Leu Lys Ala Lys His Phe His Phe Asn Lys Asn Lys
        195                 200                 205

Leu Ser Gly Pro Ile Pro Glu Lys Leu Phe Asn Ser Ala Met Val Leu
    210                 215                 220

Ile His Val Leu Phe Asp Gly Asn Gln Leu Asn Gly Ser Ile Pro Ser
225                 230                 235                 240

Ser Val Gly Leu Leu Pro Asp Leu Glu Val Leu Arg Leu Asp Arg Asn
                245                 250                 255

Lys Leu Ser Gly Lys Val Pro Leu Asn Leu Asn Asn Leu Thr Asn Leu
            260                 265                 270

Ser Glu Leu Asn Phe Ala His Asn Ala Leu Thr Gly Pro Leu Pro Asp
        275                 280                 285

Leu Thr Asp Met Asn Ser Leu Asn Tyr Val Asp Leu Ser Asn Asn Phe
```

-continued

```
            290                 295                 300
Phe Asp Pro Ser Glu Ala Pro Asp Trp Phe Ser Thr Leu Pro Thr Leu
305                 310                 315                 320
Thr Thr Leu Val Ile Glu Tyr Gly Pro Leu Lys Gly Val Val Pro Gln
                325                 330                 335
Lys Leu Phe Ser Phe Pro Gln Leu Gln Gln Val Lys Leu Lys Asn Asn
                340                 345                 350
Glu Phe Asn Gly Thr Leu Asn Met Gly Asp Asn Ile Ser Pro Gln Leu
                355                 360                 365
Gln Leu Val Asp Leu Gln Asn Asn Gln Ile Ser Ser Val Thr Leu Gly
        370                 375                 380
Ser Ser Gly Tyr Ser Asn Thr Leu Met Leu Ile Gly Asn Pro Val Cys
385                 390                 395                 400
Thr Thr Glu Leu Ser Asn Thr Asn Tyr Cys Gln Leu Gln Gln Gln Thr
                405                 410                 415
Val Lys Pro Tyr Ser Thr Ser Leu Ala Ser Cys Gly Ser Lys Ser Cys
                420                 425                 430
Pro Pro Asp Glu Arg Leu Asn Pro Gln Ser Cys Glu Cys Ala Phe Pro
                435                 440                 445
Tyr Glu Gly Thr Leu Tyr Phe Arg Gly Pro Ser Phe Arg Glu Leu Ser
        450                 455                 460
Asn Val Thr Leu Phe His Met Leu Glu Met Asp Leu Trp Thr Lys Leu
465                 470                 475                 480
Asn Leu Thr Pro Gly Ser Val Ser Leu Gln Asn Pro Phe Phe Asn Leu
                485                 490                 495
Asp Asp Tyr Leu Gln Val Gln Leu Ser Leu Phe Pro Pro Ser Gly Lys
                500                 505                 510
Tyr Phe Ser Arg Ser Asp Ile Gln Ser Ile Gly Phe Asp Leu Thr Asn
                515                 520                 525
Gln Thr Phe Lys Pro Pro Lys Pro Phe Gly Pro Tyr Tyr Phe Ile Ala
        530                 535                 540
Ser Pro Tyr Ala Phe Pro Asp Asn Gly Gly Thr Ala Ile Ser Lys Gly
545                 550                 555                 560
Val Ile Val Gly Ile Ala Ile Gly Gly Thr Val Leu Val Leu Gly Leu
                565                 570                 575
Val Val Leu Gly Leu Tyr Ala Ile Arg Gln Lys Lys Arg Ala Glu Lys
                580                 585                 590
Ala Leu Glu Leu Ser Arg Pro Phe Ala Ser Trp Ala Pro Ser Gly Lys
                595                 600                 605
Asp Ser Gly Gly Ala Pro Gln Leu Lys Gly Ala Arg Trp Phe Ser Tyr
                610                 615                 620
Asp Glu Leu Lys Arg Cys Thr Asn Asn Phe Ser Asp Ser Asn Glu Leu
625                 630                 635                 640
Gly Phe Gly Gly Tyr Gly Lys Val Tyr Arg Gly Val Leu Pro Asp Gly
                645                 650                 655
His Ile Leu Ala Ile Lys Arg Ala Gln Gln Gly Ser Met Gln Gly Ala
                660                 665                 670
Thr Glu Phe Lys Thr Glu Ile Glu Leu Leu Ser Arg Val His His Lys
                675                 680                 685
Asn Leu Val Gly Leu Ile Gly Phe Cys Phe Glu Gln Gly Glu Gln Met
        690                 695                 700
Leu Val Tyr Glu Tyr Met Pro Asn Gly Thr Leu Arg Asp Ser Leu Thr
705                 710                 715                 720
```

```
Gly Lys Ser Gly Ile Tyr Leu Asp Trp Lys Arg Arg Leu Arg Ile Ala
                725                 730                 735
Leu Gly Ser Ala Arg Gly Leu Ala Tyr Leu His Glu Leu Ala Asn Pro
            740                 745                 750
Pro Ile Ile His Arg Asp Val Lys Ser Thr Asn Ile Leu Leu Asp Glu
        755                 760                 765
His Leu Thr Ala Lys Val Ala Asp Phe Gly Leu Ser Lys Leu Val Ser
    770                 775                 780
Asp Ser Gly Lys Gly His Val Ser Thr Gln Val Lys Gly Thr Leu Gly
785                 790                 795                 800
Tyr Leu Asp Pro Glu Tyr Tyr Met Ser Gln Gln Leu Thr Glu Lys Ser
                805                 810                 815
Asp Val Tyr Ser Phe Gly Val Val Met Leu Glu Leu Ile Thr Ala Lys
            820                 825                 830
Gln Pro Ile Glu Lys Gly Lys Tyr Val Val Arg Glu Ile Arg Thr Ala
        835                 840                 845
Met Asp Lys Asn Asp Gln Asp Tyr Tyr Gly Val Arg Glu Met Met Asp
    850                 855                 860
Pro Ser Met Arg Ser Met Gly Tyr Leu Val Gly Phe Ser Arg Phe Leu
865                 870                 875                 880
Asp Leu Ala Met Arg Cys Val Glu Ser Ala Ala Asp Arg Pro Thr
                885                 890                 895
Met Ser Glu Val Val Lys Ala Ile Glu Thr Met Leu Gln Asn Asp Gly
            900                 905                 910
Ile His Thr Asn Ser Thr Ser Ala Ser Ser Ala Thr Asp Phe Gly
        915                 920                 925
Ser Thr Lys Gly Ala Pro Arg His Pro Tyr Asn Asp Ala Leu Pro Lys
930                 935                 940
Lys Glu Val Ser Tyr Ser Asp Ser Phe Asp Tyr Ser Gly Gly Tyr Gly
945                 950                 955                 960
Leu Ser Thr Lys Ile Glu Pro Lys
                965
```

<210> SEQ ID NO 77
<211> LENGTH: 632
<212> TYPE: PRT
<213> ORGANISM: Pinus radiata

<400> SEQUENCE: 77

```
Met Leu Phe Pro Trp Arg Ser Leu Val Leu Ile Ala Phe Thr Ser Leu
 1               5                  10                  15
Val Val Gln Leu Ile Pro Ala Gln Ala Val Glu Asp Arg Arg His Asp
                20                  25                  30
Thr Thr Phe Leu Phe Asp Gly Phe Asn Gly Thr Asn Leu Ile Leu Glu
            35                  40                  45
Ala Asn Ala Ser Val Ile Gly Ser Glu Ser Val Leu Ser Leu Thr Asn
        50                  55                  60
His Ser His Glu Phe Met Leu Gly Arg Ala Leu Tyr Ala Ala Pro Val
65                  70                  75                  80
Gln Met Lys Asn Asn His Thr Val Ser Ser Phe Ser Thr Phe Val
                85                  90                  95
Phe Ser Ile Val Pro Pro Ser Asn Glu Gly Gly His Gly Leu Ala
            100                 105                 110
Phe Ile Met Thr Pro Tyr Thr Ser Pro Met Gly Ala Gln Pro Val Gln
```

-continued

```
            115                 120                 125
Tyr Leu Gly Leu Leu Asn Leu Thr Ser Asn Gly Gln Pro Tyr Asn His
            130                 135             140

Leu Phe Ala Val Glu Phe Asp Thr Ile Met Asn Val Glu Phe Lys Asp
145                 150                 155                 160

Pro Asp Arg Asn His Val Gly Val Asp Ile Asn Ser Leu Ile Ser Val
                165                 170                 175

Gln Thr Glu Thr Ala Gly Tyr Trp Asn Gly Glu Glu Phe His Glu Leu
            180                 185                 190

Asn Leu Arg Ser Gly Arg Asn Ile Gln Ala Trp Ile Asp Tyr Asp His
            195                 200                 205

Leu Glu Ser Ser Leu Asn Val Thr Ile Thr Val Ala Gly Leu Pro Arg
            210                 215                 220

Pro Gln Arg Pro Leu Ile Ser Leu Gln Ile Asp Leu Gln Asn Ile Val
225                 230                 235                 240

Glu Glu Lys Met Leu Val Gly Phe Ser Ala Ala Thr Gly Leu Leu Val
                245                 250                 255

Glu Asp His Tyr Ile Leu Ala Trp Ser Phe Thr Thr Glu Asp Thr Ala
            260                 265                 270

Pro Pro Leu Asp Val Ser Cys Leu Ser Ser Phe Ala Asn Met Tyr Ser
            275                 280                 285

Glu Pro Leu Ser Arg Gly Phe Ile Ala Gly Val Thr Val Ser Val
290                 295                 300

Val Leu Phe Trp Leu Val Ile Ala Ala Ala Met Phe Leu Arg Arg Thr
305                 310                 315                 320

Leu Asn Arg Glu Thr Val Glu Glu Trp Glu Gln Glu Tyr Trp Pro His
            325                 330                 335

Arg Phe Asp Tyr Lys Glu Leu Arg Ile Ala Thr Arg Gly Phe Arg Asp
            340                 345                 350

Glu Asn Leu Leu Gly Tyr Gly Gly Phe Gly Met Val Tyr Lys Gly Phe
            355                 360                 365

Leu Pro Arg Ser Gly Gln Glu Val Ala Val Lys Cys Ile Thr Thr Glu
            370                 375                 380

Phe Lys Glu Gly Ile Lys Gly Phe Val Ala Glu Ile Ser Ser Met Gly
385                 390                 395                 400

Arg Leu Gln His Arg Asn Leu Val Gln Leu Arg Gly Trp Cys Arg Arg
                405                 410                 415

His Thr Gln Leu Phe Ile Val Tyr Asp Tyr Met Pro Asn Gly Ser Leu
            420                 425                 430

His Lys Leu Ile Phe Gly Ser Pro Thr Thr Val Leu Pro Trp His Arg
            435                 440                 445

Arg Tyr Ala Ile Leu Lys Gly Val Ala Ala Gly Leu Leu Tyr Leu His
            450                 455                 460

Glu Gln Trp Glu Lys Arg Val Val His Arg Asp Ile Lys Ser Ser Asn
465                 470                 475                 480

Val Leu Leu Asp Ser Glu Phe Asn Gly Arg Leu Ser Asp Phe Gly Leu
                485                 490                 495

Ala Arg Leu Tyr Asp His Ser Glu Asn Pro Glu Thr Thr Tyr Val Val
            500                 505                 510

Gly Thr Leu Gly Tyr Ile Ala Pro Glu Leu Ile Gln Thr Gly Lys Ala
            515                 520                 525

Thr Pro Ser Ser Asp Val Phe Ser Phe Gly Val Leu Leu Leu Glu Val
530                 535                 540
```

```
Ala Cys Gly Lys Ser Pro Val Asp Ser Leu Glu Asp Ser Glu Arg Met
545                 550                 555                 560

Ile Leu Val Glu Trp Ala Trp Glu Leu Tyr Thr Glu Gly Arg Leu Leu
                565                 570                 575

Glu Ala Ser Asp Pro Lys Leu Ala Ala Lys Gly Gly Tyr Asp Glu Gly
            580                 585                 590

Glu Met Glu Lys Val Leu Lys Leu Gly Leu Leu Cys Ser His Pro Glu
        595                 600                 605

Pro Glu Ser Arg Leu Ser Met Arg Gln Val Cys Gln Val Leu Asn Gly
    610                 615                 620

Glu Ala Pro Val Pro Cys Arg Trp
625                 630

<210> SEQ ID NO 78
<211> LENGTH: 903
<212> TYPE: PRT
<213> ORGANISM: Eucalyptus grandis

<400> SEQUENCE: 78

Met Gly Leu Lys Ile Phe Ser Val Gly Phe Ala Leu Leu Cys Cys Phe
1               5                   10                  15

Cys Ser Leu Gly Phe Cys Asp Gln Asp Gly Phe Leu Ser Leu Ala Cys
            20                  25                  30

Gly Gly Thr Thr Asn Tyr Thr Asp Ser Ser Asn Ile Trp Trp Ile Thr
        35                  40                  45

Asp Ser Asp Phe Ile Ser Thr Gly Lys Thr Thr Tyr Val Asp Asn Ile
    50                  55                  60

Glu Gly Asn Ser Ser Gly Val Ser Leu Arg Phe Phe Pro Asp Ser Lys
65                  70                  75                  80

Val His Asn Cys Tyr Arg Leu Pro Val Arg Asn Ile Ser Ser Leu Ile
                85                  90                  95

Leu Val Arg Ser Gln Phe Val Tyr Lys Asn Tyr Asp Gly Arg Gly Lys
            100                 105                 110

Pro Pro Ala Phe Ser Val Ser Leu Gly Thr Ala Met Ala Ser Thr Ile
        115                 120                 125

Asn Leu Thr Thr Asn Asp Pro Trp Thr Glu Glu Phe Ile Trp Pro Val
    130                 135                 140

Asp Lys Asp Thr Leu Ser Phe Cys Leu His Arg Ile Arg Asn Gly Gly
145                 150                 155                 160

Thr Pro Val Ile Ser Leu Leu Glu Val Arg Pro Leu Pro Pro Glu Ala
                165                 170                 175

Tyr Lys Ser Gly Met Gly Asp Tyr Pro Asn Lys Leu Leu Arg Lys Ser
            180                 185                 190

Tyr Arg Ile Asp Ser Gly Tyr Thr Asn Gly Ser Leu Lys Tyr Pro Ala
        195                 200                 205

Asp Pro Tyr Asp Arg Ile Trp Asp Ala Asp Lys Ser Phe Thr Pro Phe
    210                 215                 220

His Val Thr Thr Gly Phe Lys Ile Gln Val Glu Phe Asn Leu Ser Gly
225                 230                 235                 240

Leu Ser Glu Ser Pro Pro Ala Val Leu Gln Thr Ala Arg Val Leu
                245                 250                 255

Ala Arg Lys Glu Val Leu Thr Tyr Asn Phe Pro Leu Asp Ser Leu Gly
            260                 265                 270

Asp Tyr Tyr Val Val Leu Tyr Phe Ala Gly Ile Leu Pro Ile Ser Pro
```

-continued

```
                   275                 280                 285
Ser Phe Asp Val Ile Ile Asn Gly Asp Ile Val Gln Ser Asn Tyr Thr
    290                 295                 300

Val Lys Thr Ser Ala Ala Ser Ala Leu Tyr Val Thr Arg Lys Lys Ile
305                 310                 315                 320

Lys Ser Leu Asn Val Thr Leu Lys Ser Lys Arg Phe Phe Pro Gln Val
                325                 330                 335

Asn Ala Ile Glu Val Tyr Glu Leu Val Asp Ile Pro Pro Glu Ala Ser
                340                 345                 350

Ser Thr Thr Val Ser Ala Leu Gln Val Ile Glu Gln Phe Thr Gly Leu
            355                 360                 365

Asp Leu Gly Trp Glu Asp Pro Cys Ser Pro Lys Pro Trp Asp His
370                 375                 380

Val Gly Cys Glu Gly Ser Leu Val Thr Ser Leu Asp Leu Ser Asp Ile
385                 390                 395                 400

Asn Leu Arg Ser Ile Ser Pro Thr Phe Gly Asp Leu Leu Asp Leu Lys
                405                 410                 415

Thr Leu Asp Leu His Asn Ala Ser Leu Ala Gly Glu Ile Gln Asn Leu
            420                 425                 430

Asp Ser Leu Gln Asn Leu Glu Lys Leu Asn Leu Ser Phe Asn Lys Leu
            435                 440                 445

Thr Ser Phe Gly Ser Asp Trp Glu Asn Leu Ile Ser Leu Gln Val Leu
450                 455                 460

Asp Val Gln Asn Asn Ser Leu Asp Gly Val Val Pro Asp Gly Leu Gly
465                 470                 475                 480

Glu Leu Lys Asp Leu His Leu Leu Asp Leu Glu Asn Asn Leu Leu Gln
                485                 490                 495

Gly Thr Leu Pro Asp Ser Leu Asn Arg Gln Ser Leu Glu Val Arg Thr
                500                 505                 510

Ser Gly Asn Leu Cys Leu Ser Phe Ser Thr Thr Ala Cys Gly Asp Ala
            515                 520                 525

Ser Ser Ser Pro Ser Ile Glu Ala Pro Gln Val Thr Ile Val Pro Glu
            530                 535                 540

Arg Asn Lys Gly Gly His Asn Arg Leu Ala Ile Ile Leu Gly Ala Val
545                 550                 555                 560

Gly Gly Val Ser Leu Ala Ile Leu Leu Ile Pro Leu Phe Val Phe Met
                565                 570                 575

Tyr Arg Arg Arg Gly Arg Thr Glu Met Ser Tyr Thr Glu Arg Ala Val
                580                 585                 590

Ala Asp Val Arg Asn Trp Asn Ala Ala Lys Ile Phe Ser Tyr Lys Glu
            595                 600                 605

Ile Lys Thr Ala Thr Asn Asn Phe Lys Glu Val Ile Gly His Gly Ser
            610                 615                 620

Phe Gly Ser Val Tyr Leu Gly Asn Leu Pro Val Gly Lys Leu Val Ala
625                 630                 635                 640

Val Lys Val Arg Phe Asp Lys Thr Gln Leu Gly Ala Asp Ser Phe Ile
                645                 650                 655

Asn Glu Val Arg Leu Leu Ser Gln Val Arg His Gln Asn Leu Val Ser
            660                 665                 670

Leu Glu Gly Phe Cys Tyr Glu Ser Gln Arg Gln Ile Leu Val Tyr Glu
            675                 680                 685

Tyr Leu Pro Gly Gly Ser Leu Ala Asp Gln Leu Tyr Gly Pro Asn Ser
            690                 695                 700
```

-continued

```
Arg Lys Phe Ser Leu Ser Trp Val Arg Leu Lys Ile Ala Val Asp
705                 710                 715                 720

Ala Ala Lys Gly Leu Asp Tyr Leu His Asn Gly Ser Asn Pro Arg Ile
            725                 730                 735

Ile His Arg Asp Ile Lys Cys Ser Asn Ile Leu Leu Asp Lys Glu Met
            740                 745                 750

Asn Ala Arg Leu Cys Asp Phe Gly Leu Ser Lys Gln Met Ile Gln Pro
            755                 760                 765

Asp Ala Thr His Val Thr Thr Val Val Lys Gly Thr Ala Gly Tyr Leu
    770                 775                 780

Asp Pro Glu Tyr Tyr Ser Thr Gln Gln Leu Thr Glu Lys Ser Asp Val
785                 790                 795                 800

Tyr Ser Phe Gly Val Val Leu Leu Glu Leu Ile Cys Gly Arg Glu Pro
                805                 810                 815

Leu Asn His Ser Gly Thr Pro Asp Ser Phe Asn Leu Val Leu Trp Ala
            820                 825                 830

Lys Pro Tyr Leu Gln Ala Gly Ala Phe Glu Ile Val Asp Glu Ser Leu
            835                 840                 845

Gly Gly Ser Phe Asp Val Glu Ser Met Arg Lys Val Ala Lys Ile Ala
    850                 855                 860

Val Arg Ser Val Glu Arg Asp Ala Ser Leu Arg Pro Thr Ile Ala Gln
865                 870                 875                 880

Ile Leu Ser Val Leu Lys Glu Ala Tyr Ser Ile Gln Leu Ser Tyr Leu
                885                 890                 895

Ala Ala Ser Gly His Val Asn
            900
```

<210> SEQ ID NO 79
<211> LENGTH: 711
<212> TYPE: PRT
<213> ORGANISM: Pinus radiata

<400> SEQUENCE: 79

```
Met Gly Cys Arg Lys Ala Val Arg Ser Val Ser Pro Gln Asn Pro Ser
1               5                   10                  15

Ser Ser Leu Met His Leu Arg Leu Leu Gly Val Leu Leu Met Leu His
            20                  25                  30

Cys Ile Asp Gly Leu Ile Leu Asn Pro Glu Val Ser Thr Leu Leu Thr
            35                  40                  45

Leu Lys Pro Thr Leu Ser Gly Thr Gly Val Asn Val Val Leu Ala Ser
    50                  55                  60

Trp Ser Ala Ser Arg Pro Leu Cys Gly Trp Lys Gly Val Met Trp Met
65                  70                  75                  80

Tyr Asn Gly Ile Pro Val Asn Cys Ser Val Pro Lys Phe Arg His Ser
                85                  90                  95

Val Ala Leu Ala Tyr Ser Arg Lys Val Ser Val Leu Gly Ile Asp Leu
            100                 105                 110

Glu Ala Thr Gly Leu Lys Gly Thr Val Pro Lys Glu Leu Gly Ser Phe
        115                 120                 125

Ile Tyr Leu Gln Gln Leu Asn Leu Asn Asn Ser Leu Thr Gly Gly
    130                 135                 140

Met Pro Pro Glu Leu Gly Asn Val Pro Asn Leu Ser Ser Leu Gln Leu
145                 150                 155                 160

Lys Asn Asn Gly Leu Asn Gly Gly Ile Pro Thr Ala Ile Trp Asn Leu
```

```
                    165                 170                 175
Cys Asp Asn Ile Thr Glu Leu Glu Leu Gly Phe Asn Glu Leu Ser Gly
                180                 185                 190

Ser Ile Pro Glu Pro Gly Asn Gly Ser Asn Ile Gly Cys Pro Gln Leu
            195                 200                 205

Arg Arg Phe Glu Val Asn Asn Asn Ser Leu Thr Gly Thr Ile Pro Ser
        210                 215                 220

Phe Leu Ala Asn Cys Ile Ser Leu Gln Glu Leu Asp Leu Ser Gly Asn
225                 230                 235                 240

Ser Phe Thr Gly Glu Ile Pro Asn Glu Leu Ala Asn Leu Pro Asn Leu
                245                 250                 255

Thr Thr Leu Asn Leu Ala His Asn Asn Leu Ser Gly Arg Ile Pro Ser
            260                 265                 270

Phe Arg Gln Lys Phe Asp Lys Asn Ser Phe Val Glu Asn Ser Gly Ser
        275                 280                 285

Leu Cys Gly Gln Pro Leu Leu Asn Pro Cys Gly Val Ala Pro Asn Ala
290                 295                 300

Ala Ser Ala Ala Ser Ala Asn Val Thr Ala Ala Gln Phe Asn Val Thr
305                 310                 315                 320

Lys Ala His Phe Lys Ser Met Ser Thr Gly Ala Ile Ala Gly Ile Ile
                325                 330                 335

Ile Gly Ser Ile Ala Val Val Val Ile Ala Ser Ser Leu Leu Ile Gly
            340                 345                 350

Cys Tyr His Arg Phe Ser Thr Asp Ala Thr Asp Lys Ser Ser Ser Ser
        355                 360                 365

Ser Ala Pro Ser Lys Lys Asp Lys Glu Asp Met Asp Asn Val Ser
370                 375                 380

Gly Lys Leu Ile Asn Phe Gln Gly Gly Glu His Leu Thr Val Asp Asp
385                 390                 395                 400

Val Leu Asn Ala Thr Gly Glu Val Leu Gly Lys Ser Ser Tyr Gly Thr
                405                 410                 415

Val Tyr Lys Ala Arg Leu Ser Ser Gly Cys Met Ile Ala Leu Arg Leu
            420                 425                 430

Leu Arg Asp Gly Cys Leu Arg Ser Thr Asp Glu Phe Met Pro Ala Ile
        435                 440                 445

Gln Glu Leu Gly Thr Ile Arg His Lys His Leu Val Ser Leu Arg Ala
450                 455                 460

Phe Tyr Ser Gly Thr Arg Gly Glu Lys Leu Leu Ala Tyr Asp Tyr Leu
465                 470                 475                 480

Pro Arg Gly Ser Leu Ala Glu Leu Leu His Ser Thr Asn Arg Pro Ala
                485                 490                 495

Pro Gly Trp Ala Arg Arg His Lys Ile Ala Leu Gly Ala Ala Arg Gly
            500                 505                 510

Leu Ala Tyr Leu His Thr Gly Phe His Lys Ser Ile Ile His Gly Asn
        515                 520                 525

Ile Lys Ser Lys Asn Ile Leu Val Asp Asp Asn Tyr Val Ala His Leu
530                 535                 540

Ser Asp Tyr Gly Leu Asn Lys Leu Met Asn Ser Thr Ala Asn Ile Glu
545                 550                 555                 560

Met Leu Glu Ala Ala Ala Ser Gln Gly Tyr Lys Ala Pro Glu Leu Ile
                565                 570                 575

Lys Met Lys Arg Ala Asn Ala Lys Thr Asp Ile Tyr Ser Phe Gly Ile
            580                 585                 590
```

```
Gly Leu Leu Glu Ile Leu Thr Gly Arg Arg Pro Gly Arg Thr Ser Ser
            595                 600                 605

Ser Asn His Ile Val Asp Leu Pro Thr Val Val Lys Asn Ala Val Leu
            610                 615                 620

Glu Glu Arg Ile Ser Glu Leu Phe Asp Leu Glu Leu Leu Arg Ala Met
625                 630                 635                 640

Arg Ser Pro Ala Asp Glu Gly Leu Leu Gln Val Leu Gln Leu Ala Met
                645                 650                 655

Gly Cys Cys Ala Pro Ser Pro Ser Val Arg Pro His Ile Lys Glu Val
                660                 665                 670

Val Arg Gln Leu Glu Glu Ile Arg Pro Lys Pro Gln Ser Pro His Leu
            675                 680                 685

Ala Leu Ser Pro Gln Tyr Asn Ser Asp Asp Lys Ser Ser Arg Glu Phe
            690                 695                 700

Leu Leu Asp Gly Gly Gln Asn
705                 710

<210> SEQ ID NO 80
<211> LENGTH: 707
<212> TYPE: PRT
<213> ORGANISM: Pinus radiata

<400> SEQUENCE: 80

Met Gly Lys Lys Ile Leu Gln Cys Leu Arg Leu Ile Ile Ala Ile Leu
1               5                   10                  15

Thr Ala Ser Ile Ala Ile Ser His Gly Thr Thr Asp Pro Asp Asp Val
            20                  25                  30

Ser Ala Leu Lys Gly Ile Tyr Ser Ser Leu Asn Ser Pro Gln Gln Leu
        35                  40                  45

Ser Gly Trp Ser Ala Asn Gly Gly Asp Pro Cys Gly Gln Ser Trp Lys
    50                  55                  60

Gly Val Ser Cys Ser Gly Ser Ser Val Thr Leu Ile Lys Leu Ser Gly
65                  70                  75                  80

Leu Gly Leu Ser Gly Ser Leu Tyr Tyr Gln Leu Ser Asp Leu Ser Ser
                85                  90                  95

Leu Thr Thr Leu Asp Leu Ser Asn Asn Ile Gln Gly Asn Ile Pro
            100                 105                 110

Tyr Ala Leu Pro Gln Lys Leu Gln Glu Leu Asn Leu Ala Ser Asn Gly
            115                 120                 125

Leu Ser Gly Thr Ile Pro Tyr Ser Ile Ser Asn Met Thr Gly Leu Thr
    130                 135                 140

Asp Leu Lys Leu Ser His Asn Gln Leu Ser Gly Gln Ile Gln Asp Ile
145                 150                 155                 160

Phe Gly Gln Leu Ser Ser Leu Ser Thr Leu Asp Leu Ser Phe Asn Thr
                165                 170                 175

Leu Thr Gln Asn Leu Pro Gln Ser Phe Ser Ser Leu Ser Ser Leu Ser
            180                 185                 190

Val Leu Tyr Leu Gln Asn Asn Gln Leu Ala Gly Ser Val Asn Val Leu
        195                 200                 205

Ala Asn Leu Pro Leu Thr Asp Leu Asn Ile Glu Asn Asn Arg Phe Ser
    210                 215                 220

Gly Trp Val Pro Asn Ala Trp Arg Ser Asn Gln Asn Phe Lys Tyr Ser
225                 230                 235                 240

Ser Gly Asn Ser Phe Ala Thr Gly Pro Ala Pro Pro Pro Pro Tyr
```

```
                  245                 250                 255
Thr Pro Pro Pro Ser Asn Asn Arg Pro Pro Lys Ser Ser Asn Val
            260                 265             270

Val Pro Ser Ser Gly Gly Ser Lys Gly Gly Asn Ser Asn Lys Lys Ser
        275                 280             285

Leu Ser Gly Gly Ala Ile Val Gly Ile Ile Phe Ala Val Ile Leu Thr
    290                 295                 300

Val Val Ala Ala Ile Leu Gly Val Ile Leu Tyr Ala Arg Lys Ser Pro
305             310                 315                 320

Arg Arg Glu Gln Asp Glu Glu Lys Leu Ser Asn Arg Val Ser Phe Thr
            325                 330                 335

Pro Leu Ser Pro Leu Asp Ala Glu Leu Leu Lys Glu Ser Pro Glu Gln
            340                 345                 350

Lys Val Ser Ser Ser Pro Leu Glu Ile Ala Leu Lys Pro Pro Pro Ser
            355                 360                 365

Glu Arg Asn Lys Ser Thr Gly Asp Lys Gly Phe Gly Ser Ile Phe Ser
            370                 375                 380

Ser Lys Arg Thr Lys Asn Pro Ile Ser Ala Thr Glu Tyr Ser Ile Ala
385             390                 395                 400

Asp Leu Gln Met Ala Thr Asn Ser Phe Ser Gln Asp Asn Leu Ile Ala
                405                 410                 415

Glu Gly Ala Leu Gly Arg Ile Tyr Arg Ala Glu Phe Pro Asp Gly Lys
            420                 425                 430

Ile Leu Ala Val Lys Lys Leu Asp Thr Ser Thr Leu Ser Leu Gln Arg
            435                 440                 445

Pro Glu Asp Phe Leu Asp Ala Val Ser Asn Ile Ser Arg Leu His His
    450                 455                 460

Pro Asn Ile Thr Glu Leu Val Gly Tyr Cys Thr Glu His Gln Tyr
465             470                 475                 480

Leu Leu Val Tyr Glu Tyr Phe Asp Asn Gly Ser Leu Tyr Asp Val Leu
                485                 490                 495

His Met Ala Asp Glu Thr Thr Arg Asn Leu Ser Trp Asn Ile Arg Val
                500                 505                 510

Lys Ile Ala Leu Gly Ser Ala Arg Val Leu Glu Tyr Leu His Glu Val
            515                 520                 525

Cys Ser Pro Ser Ile Val His Lys Lys Phe Lys Ser Ser Asn Ile Leu
530                 535                 540

Leu Asp Asp Asp Phe Asn Pro Arg Leu Ser Asp Cys Gly Ile Ala Ala
545                 550                 555                 560

Leu Asn Pro Asn Ser Glu Arg Gln Val Gln Val Leu Gly Ser Phe Gly
                565                 570                 575

Tyr Ser Ala Pro Glu Tyr Val Met Ser Gly Ile Tyr Thr Met Lys Ser
            580                 585                 590

Asp Val Tyr Ser Phe Gly Val Val Met Leu Glu Leu Leu Thr Gly Arg
            595                 600                 605

Lys Pro Leu Asp Ser Ser Arg Thr Arg Ser Glu Gln Ser Leu Val Arg
    610                 615                 620

Trp Ala Thr Pro Gln Leu His Asp Ile Asp Ala Leu Ala Lys Met Val
625                 630                 635                 640

Asp Pro Ala Leu Lys Gly Ser Tyr Pro Ala Lys Ser Leu Ser Arg Phe
                645                 650                 655

Ala Asp Ile Ile Ala Leu Cys Ile Gln Pro Glu Pro Glu Phe Arg Pro
                660                 665                 670
```

```
Pro Met Ser Glu Val Val Gln Ala Leu Val Arg Met Gln Arg Ala
        675                 680                 685
Ser Leu Asn Lys Arg Met Thr Gly Asp Glu Thr Ala Asp His Asp Pro
        690                 695                 700
Ala Asp Tyr
705

<210> SEQ ID NO 81
<211> LENGTH: 20
<212> TYPE: PRT
<213> ORGANISM: Pinus radiata

<400> SEQUENCE: 81

Met Gln Gln Pro Tyr Val Val Leu Ala Leu Trp Trp Ile Leu Val Leu
 1               5                  10                  15
Arg His Pro Leu
        20

<210> SEQ ID NO 82
<211> LENGTH: 89
<212> TYPE: PRT
<213> ORGANISM: Eucalyptus grandis

<400> SEQUENCE: 82

Met Arg Val Leu Phe Ile Val Leu Gly Val Val Leu Leu Cys Thr Val
 1               5                  10                  15
Ile Pro Gly Ser Ser Ser Val Ser Asp Val Asp Val Leu Leu Ala
                20                  25                  30
Leu Lys Gln Gly Phe Gln Ser Pro Glu Pro Ala Leu Ile Thr Trp Ser
                35                  40                  45
Ser Ser Asn Ser Ser Ser Val Cys Leu Trp Tyr Gly Ile Arg Cys Ser
        50                  55                  60
Arg Gly Arg Val Val Ser Leu Gln Leu Thr Asp Leu Asn Leu Gly Gly
65                  70                  75                  80
Ser Val Ser Pro Pro Val Ser Arg Leu
                85

<210> SEQ ID NO 83
<211> LENGTH: 153
<212> TYPE: PRT
<213> ORGANISM: Pinus radiata

<400> SEQUENCE: 83

Met Leu Leu Cys Phe Val Leu Val Ala Gly Thr Ser Ala Ala Val Asp
 1               5                  10                  15
Asp His Gln Tyr Leu Tyr His Pro Ser His Tyr Val Met Asn Glu Arg
                20                  25                  30
Gln Glu Ser Gly Ser Ser Met Ala Arg His Glu Lys Arg Asp Val Glu
                35                  40                  45
Ala Leu Leu Ser Phe Arg Asn Ala Ile Thr Ala Asp Pro His Gly Leu
        50                  55                  60
Leu Ser Asn Trp Thr Ala His Asn Ser Ala Asn Ile Cys Ser Trp Asn
65                  70                  75                  80
Gly Ile Gly Cys Arg Lys Gln Ser Arg Val Val Ser Ile Tyr Leu
                85                  90                  95
Arg Phe Ser His Leu Glu Gly Thr Leu Ser Pro Ser Val Gly Asn Ile
                100                 105                 110
```

```
Ser Leu Leu His Thr Phe Val Leu Thr Val Asn Lys Leu Thr Gly Arg
            115                 120                 125

Ile Pro Pro Glu Phe Gly Gln Leu Lys Ala Leu Gln Thr Leu Asp Leu
        130                 135                 140

Tyr Arg Asn Leu Leu Ser Ser Ser Gly
145                 150

<210> SEQ ID NO 84
<211> LENGTH: 154
<212> TYPE: PRT
<213> ORGANISM: Pinus radiata

<400> SEQUENCE: 84

Met Asp Leu Leu Leu Leu Leu Val Met Met Gly Val Ala Met Pro
 1               5                  10                  15

Thr His Ser Gln His Thr Gly Gly Phe Thr Ser Val Gln Arg Phe Pro
                20                  25                  30

Phe Asn Gly Arg Ser Met Met Gly Lys Pro Ser Ile Ala Gly Tyr His
            35                  40                  45

Glu Lys Arg Asp Val Glu Ala Leu Leu Ser Phe Arg Lys Gly Ile Thr
 50                  55                  60

Leu Asp Pro Tyr Gly Trp Leu Ser Asn Trp Thr Ala Asn Asn Ser His
65                  70                  75                  80

Asn Val Cys Leu Trp Asn Gly Ile Ser Cys Ser Pro Asn Thr Asn Arg
                85                  90                  95

Val Val Glu Ile Ser Leu Arg Tyr Gly Arg Leu Asn Gly Thr Leu Ser
            100                 105                 110

Pro Tyr Ile Gly Asn Leu Ser Leu Leu Arg His Leu Asp Leu Ser Ser
        115                 120                 125

Asn Ala Leu Ser Gly Arg Ile Pro Ala Lys Phe Gly Gln Leu Lys Ala
    130                 135                 140

Leu Arg Ile Leu Asp Leu Ser Asn Asn Ala
145                 150

<210> SEQ ID NO 85
<211> LENGTH: 82
<212> TYPE: PRT
<213> ORGANISM: Eucalyptus grandis

<400> SEQUENCE: 85

Met Val Phe Arg Arg Phe Val Val Met Leu Phe Ile Cys Thr Ala Ser
 1               5                  10                  15

Val Cys Ala Gly Leu Thr Asp Pro Arg Asp Val Ala Ala Ile Asn Ser
                20                  25                  30

Leu Tyr Val Ser Leu Gly Tyr Pro Pro Leu Arg Gly Trp Leu Leu Val
            35                  40                  45

Gly Gly Asp Pro Cys Val Asp Asn Trp Glu Gly Val Glu Cys Val Ile
 50                  55                  60

Ser Asn Ile Thr Gly Leu Asn Ser Gly Ala Asn Leu Gly Gly Glu
65                  70                  75                  80

Leu Gly

<210> SEQ ID NO 86
<211> LENGTH: 103
<212> TYPE: PRT
<213> ORGANISM: Eucalyptus grandis

<400> SEQUENCE: 86
```

```
Met Gly Phe Phe Tyr Gln Val Phe Leu Ile Phe Leu Ala Val Ala Pro
 1               5                  10                  15

Ser Ala Leu Cys Gln Val Thr Glu Phe Val Ser Ile Asp Cys Gly Gly
             20                  25                  30

Ser Ser Asn Tyr Thr Asp Pro Thr Gly Leu Ala Trp Ile Pro Asp
         35                  40                  45

Thr Gly Leu Met Ser Tyr Gly Gln Ser Ser Lys Val Gln Asn Pro Asn
         50                  55                  60

Val Ser Ser Val Gln Tyr Ser Thr Arg Arg Asp Phe Pro Ile Asp Gly
 65                  70                  75                  80

Gln Lys Tyr Cys Tyr Thr Leu Arg Thr Glu Glu Arg Arg Tyr Ile
                 85                  90                  95

Val Arg Thr Thr Phe Leu Tyr
                100
```

<210> SEQ ID NO 87
<211> LENGTH: 156
<212> TYPE: PRT
<213> ORGANISM: Pinus radiata

<400> SEQUENCE: 87

```
Met Ala Phe Pro Cys Phe Tyr Phe Pro Phe Arg Ile Leu Phe Phe Leu
 1               5                  10                  15

Phe Val Cys Ser Phe Ser Phe Ser Phe Ser Phe Ser Ala His Lys Phe
             20                  25                  30

His Asp Gly Arg Lys Trp Leu Leu Ser Phe Lys Ile Asp Ile Thr Asn
             35                  40                  45

Asp Pro His Ala Ser Met Ala Asn Trp Ser Pro Ala Val His Leu Cys
 50                  55                  60

Asn Trp Thr Ala Val Thr Cys Ser Arg Arg His Ala Asp Arg Val Val
 65                  70                  75                  80

Ser Leu Asp Leu Ser Gly Met Asp Leu Ser Gly Ser Ile Ser Pro Ser
                 85                  90                  95

Leu Gly Asn Leu Ser Phe Leu His Thr Leu Asn Leu Ser Ala Asn Ala
                100                 105                 110

Leu His Gly His Ile Pro Pro Gln Leu Gly Arg Leu Phe Arg Leu Arg
             115                 120                 125

Asn Leu Trp Leu Arg Asn Asn Phe Leu Gln Gly Asn Ile Pro Thr Glu
 130                 135                 140

Phe Ala Ser Leu Lys His Leu Gln Gln Leu Tyr Leu
 145                 150                 155
```

<210> SEQ ID NO 88
<211> LENGTH: 98
<212> TYPE: PRT
<213> ORGANISM: Eucalyptus grandis

<400> SEQUENCE: 88

```
Met Arg Phe Ser Ser Leu Lys Arg Arg Trp Ile Met Arg Thr Ala
 1               5                  10                  15

Ile Ile Ile Thr Ser Leu Met Cys Cys Ser Ser Ala Arg Asp Ser Met
             20                  25                  30

Thr Leu Ser Ser Pro Leu Ser Asp Glu His Gly Asp Thr Leu Val Ser
             35                  40                  45

Asp Gly Gly Thr Phe Gln Leu Gly Phe Phe Ser Pro Asn Gly Ser Ser
 50                  55                  60
```

-continued

Gly Ser Asp His Arg Arg Tyr Leu Gly Ile Trp Tyr Tyr Asp Ser Asp
65                  70                  75                  80

Pro Gln Thr Val Val Trp Val Ala Asn Arg Asp His Pro Val Leu Asp
                85                  90                  95

Val Thr

<210> SEQ ID NO 89
<211> LENGTH: 154
<212> TYPE: PRT
<213> ORGANISM: Eucalyptus grandis

<400> SEQUENCE: 89

Met Gly Leu Ala Arg Leu Leu Leu Val Gly Phe Val Leu Leu Val Leu
1               5                   10                  15

Gly Ser Arg Ala Leu Val Cys Gly Asn Ala Glu Leu Glu Ala Leu Met
                20                  25                  30

Glu Ile Lys Ala Ser Leu Asp Pro Glu Asn Lys Val Leu Thr Ser Trp
            35                  40                  45

Thr Ser Asn Gly Asp Pro Cys Gly Gly Ser Phe Asp Gly Val Ala Cys
    50                  55                  60

Asn Glu His Gln Lys Val Ala Asn Ile Ser Leu Gln Gly Lys Gly Leu
65                  70                  75                  80

Ser Gly Lys Val Pro Pro Ala Val Ala Gln Leu Lys Cys Leu Ser Gly
                85                  90                  95

Leu Tyr Leu His Tyr Asn Tyr Leu Thr Gly Glu Ile Pro Arg Glu Ile
            100                 105                 110

Ser Ser Leu Thr Glu Leu Thr Asp Leu Tyr Leu Asp Val Asn Asn Leu
        115                 120                 125

Thr Gly Ser Ile Pro Ser Glu Ile Gly Ser Met Ala Ser Leu Gln Gly
    130                 135                 140

Glu Phe Cys Leu Leu Leu Gln Gly Gln Gly
145                 150

<210> SEQ ID NO 90
<211> LENGTH: 157
<212> TYPE: PRT
<213> ORGANISM: Eucalyptus grandis

<400> SEQUENCE: 90

Met Gly Val Lys Arg Ala Asn Ser Ser Leu Cys Cys Val Val Leu Leu
1               5                   10                  15

Gly Leu Trp Ala Cys Val His Gly Leu Leu Ser Pro Ser Gly Val Asn
                20                  25                  30

Ile Glu Val Leu Ala Leu Met Asp Ile Arg Asn Leu Leu Val Asp Pro
            35                  40                  45

His Gln Val Leu Asn Asn Trp Asp Ala Asn Glu Val Thr Pro Cys Thr
    50                  55                  60

Trp Thr Ala Ile Thr Cys Glu Ala Asp Val Val Thr Asn Leu Glu Ile
65                  70                  75                  80

Pro Arg Gln Asn Leu Ser Gly Thr Leu Ser His Ser Ile Gly Asn Leu
                85                  90                  95

Ile Asn Leu Lys Tyr Leu Phe Leu Gln Asp Asn Asn Ile Ser Gly Phe
            100                 105                 110

Ile Pro Pro Glu Leu Gly Lys Leu Gln Lys Leu Glu Met Leu Asp Ile
        115                 120                 125

Ser Ser Asn Ser Phe Ser Gly Glu Ile Pro Thr Glu Leu Ser His Leu
            130                 135                 140

Lys Asn Leu Gln Gln Leu Arg Met Asn Tyr Asn Asn Leu
145                 150                 155

<210> SEQ ID NO 91
<211> LENGTH: 141
<212> TYPE: PRT
<213> ORGANISM: Eucalyptus grandis

<400> SEQUENCE: 91

Met Val Ser Ser Leu Leu Leu Ser Ser Gln Pro Asn Leu Val Val Gly
1               5                   10                  15

Phe Leu Phe Leu Leu Leu Val Asp Thr Thr Pro Phe His Gly Ala
            20                  25                  30

Gly Asp Met Ala Ser Ser Thr Ser Phe Phe Thr Ile Asn Met Thr Lys
            35                  40                  45

Ser Lys Asp Glu Val Glu Ala Leu Leu Asn Trp Lys Ser Thr Leu Asp
50                  55                  60

Asn Tyr Ser Gln Cys Leu Leu Ser Ser Trp His Asp Asn Asn Pro Cys
65                  70                  75                  80

Gly Phe Ser Gly Val Thr Cys Asp Asp Ser Lys Ala Val Asn Asn Leu
            85                  90                  95

Asn Leu Ser Asn Leu Gly Leu Arg Gly Thr Leu Asp Gly Leu Asp Phe
            100                 105                 110

Ser Cys Leu Thr Asn Leu Val Thr Phe Asp Leu Ser Tyr Asn Ala Ile
            115                 120                 125

Tyr Gly Ser Ile Pro Ser Ser Ile Gly Asn Leu Ser Lys
            130                 135                 140

<210> SEQ ID NO 92
<211> LENGTH: 90
<212> TYPE: PRT
<213> ORGANISM: Eucalyptus grandis

<400> SEQUENCE: 92

Met Glu Gly Lys His Leu Val Phe Leu Thr Ile Leu Leu Glu Ser
1               5                   10                  15

Ile Cys Ser Asn Val Ser Ala Ile Pro Asn Glu Asp Lys Gln Ala Leu
            20                  25                  30

Leu Asp Phe Leu Gly Asn Val Ser Leu Ser Arg Pro Leu Asn Trp Asn
            35                  40                  45

Lys Asp Ser Ser Val Cys Arg Ser Trp Thr Gly Val Lys Cys Asn Asn
50                  55                  60

Asp Gln Ser Arg Val Val Ala Leu Gln Leu Pro Gly Val Gly Ile Lys
65                  70                  75                  80

Gly Arg Ile Pro Pro Asn Thr Leu Ser Arg
            85                  90

<210> SEQ ID NO 93
<211> LENGTH: 198
<212> TYPE: PRT
<213> ORGANISM: Pinus radiata

<400> SEQUENCE: 93

Met Ala Tyr Lys Leu Leu Arg Phe Trp Leu Glu Phe Gln Ala Leu Leu
1               5                   10                  15

Val Leu Phe Pro Leu Ala Leu Ser Val Ser Gln Glu Gly Leu Val Leu

-continued

```
                    20                  25                  30
Leu Glu Val Lys Lys Glu Leu Ser Asp Pro Asn Gly Phe Leu Gly Asn
                35                  40                  45
Trp Lys Ala Glu Asp Ser Pro Cys Lys Trp Arg Gly Ile Ser Cys
 50                  55                  60
Asp Gln Arg Ser Lys Ser Val Val Gly Ile Asp Leu Ser Ser Gly Gly
 65                  70                  75                  80
Leu Val Gly Val Phe Pro Ser Val Val Cys Asn Leu Pro Gln Leu Lys
                85                  90                  95
Asn Leu Ser Leu Gly Asp Asn Ile Gly Ser Ile Leu Pro Arg Asn
                100                 105                 110
Leu Ser Met Cys Arg Gln Leu Gln Arg Leu Asn Leu Ser Gln Asn Leu
                115                 120                 125
Phe Val Gly Asn Leu Pro Asp Phe Ile Ser Glu Leu Ala Glu Leu Glu
                130                 135                 140
Tyr Leu Asp Leu Ser Ser Asn Asn Phe Ser Gly Ser Ile Pro Ala Gly
 145                 150                 155                 160
Ile Gly Lys Leu Pro Arg Leu Gln Val Leu Asn Leu Cys Cys Asn Leu
                165                 170                 175
Leu Asn Glu Thr Ile Pro Thr Phe Leu Gly Asn Leu Ser Asn Leu Gln
                180                 185                 190
Gln Leu Leu Leu Ala Tyr
                195

<210> SEQ ID NO 94
<211> LENGTH: 151
<212> TYPE: PRT
<213> ORGANISM: Pinus radiata

<400> SEQUENCE: 94

Met Gly Ser Ser Ala Ser Pro Phe Met Val Leu Leu Leu Ser Thr
 1               5                  10                  15
Leu Ile Leu Glu Ile Leu Pro Met Tyr Val Ala Thr Asn Arg Ser Glu
                20                  25                  30
Ala Asp Leu Gln Gly Leu Ile Ala Phe Lys Ala Ser Ile Thr Ser Asp
                35                  40                  45
Pro Leu Asn Ala Leu Ala Asp Trp Thr Ala Ser Ala His His Cys Asn
 50                  55                  60
Trp Ser Gly Val Ala Cys Asp Pro Leu His Asn Val Ile Ser Ile Ser
 65                  70                  75                  80
Leu Pro Glu Thr Gln Ile Gln Gly Leu Ile Ser Pro Phe Leu Ala Asn
                85                  90                  95
Ile Ser Tyr Leu Ala Ser Leu Asp Leu Arg Ser Asn Phe Phe His Gly
                100                 105                 110
Val Ile Pro Pro Gln Leu Ala Leu Cys Ser Gln Leu Ile Asp Leu Glu
                115                 120                 125
Leu Phe Asn Asn Ser Leu Thr Gly Ile Lys Leu Ile Asp Thr Val Asp
                130                 135                 140
Leu Glu Gly Gly Pro Gly Thr
 145                 150

<210> SEQ ID NO 95
<211> LENGTH: 151
<212> TYPE: PRT
<213> ORGANISM: Pinus radiata
```

```
-continued

<400> SEQUENCE: 95

Met Glu Val Arg Met Ile Thr Ile Met Ile Leu Cys Ala Ala Leu Leu
1               5                   10                  15

Cys Glu Gly Ser Gly Glu Val Asp Val Leu Met Glu Met Lys Ala Ala
            20                  25                  30

Leu Asp Pro Lys Gly Glu Ile Leu Tyr Ser Trp Val Lys Gly Gly Asp
        35                  40                  45

Pro Cys Ser Gly Thr Phe Asp Gly Val Ala Cys Asn Glu Gln Gly Lys
    50                  55                  60

Val Ala Asn Val Ser Leu Gln Gly Lys Gly Leu Ser Gly Ser Ile Pro
65                  70                  75                  80

Ser Thr Ile Gly Lys Leu Lys Cys Leu Thr Gly Leu Tyr Leu His Tyr
                85                  90                  95

Asn Ser Leu Gly Gly Glu Ile Pro Arg Glu Leu Ser Asn Leu Thr Glu
            100                 105                 110

Leu Leu Asp Leu Tyr Leu Asn Val Asn Gly Leu Ser Gly Pro Ile Pro
        115                 120                 125

Lys Glu Leu Gly Ala Met Ser Ser Leu Gln Ala Leu Gln Leu Cys Cys
    130                 135                 140

Asn Lys Leu Thr Gly Pro Ile
145                 150

<210> SEQ ID NO 96
<211> LENGTH: 116
<212> TYPE: PRT
<213> ORGANISM: Pinus radiata

<400> SEQUENCE: 96

Met Asp Leu Leu Leu Leu Leu Val Met Met Gly Val Ala Met Pro
1               5                   10                  15

Thr His Ser Gln Gln Thr Gly Gly Phe Thr Ser Val Gln Arg Phe Pro
            20                  25                  30

Phe Asn Gly Arg Ser Met Met Gly Lys Pro Ser Leu Phe Pro Ser Ser
        35                  40                  45

Ile Ala Gly Tyr His Glu Lys Arg Asp Val Glu Ala Leu Leu Ser Phe
    50                  55                  60

Arg Lys Gly Ile Ile Ser Asp Pro Val Gly Ser Leu Ser Asp Trp Thr
65                  70                  75                  80

Ala Asn Asn Ser His Asn Val Cys Leu Trp Asn Gly Ile Ser Cys Arg
                85                  90                  95

Pro Asn Thr Lys Arg Val Val Ser Ile Ser Leu Pro Glu Cys Leu Leu
            100                 105                 110

Asn Gly Thr Leu
        115

<210> SEQ ID NO 97
<211> LENGTH: 155
<212> TYPE: PRT
<213> ORGANISM: Pinus radiata

<400> SEQUENCE: 97

Met Arg Glu Arg Glu Thr Lys Val Cys Ile Phe Ile Phe Cys Ile Phe
1               5                   10                  15

Thr Ser Trp Ala Leu Val Asp Phe Gly Val Pro Ala Val Phe Ala Ala
            20                  25                  30

Gln Glu Thr Gln Ile Gln Ile Leu Leu Arg Met Lys Glu Ala Leu Glu
```

-continued

```
                35                  40                  45
Asp Pro Thr Asn Ala Leu Arg Asp Trp Asp Gly Ser Glu Asp Ser Pro
    50                  55                  60

Cys Arg Trp Arg Gly Ile Asp Cys Asn Asp Glu Gly Ala Val Thr Arg
 65                  70                  75                  80

Ile Gln Leu His Gly Ser Ser Leu Ser Gly Arg Ile Leu Pro Asp Ile
                85                  90                  95

Cys Asn Leu Gln Ser Leu Ile Ile Phe Glu Leu Asp Arg Asn Ser Leu
                100                 105                 110

Tyr Gly Asn Phe Pro Pro Glu Phe Ser Asn Cys Ser Arg Leu Glu Gln
            115                 120                 125

Leu Asn Leu Ser Ser Asn Leu Leu Asn Gly Ser Leu Pro Asp Leu Ser
        130                 135                 140

Lys Leu Lys Ala Leu Lys Tyr Leu Asp Leu Ser
145                 150                 155

<210> SEQ ID NO 98
<211> LENGTH: 96
<212> TYPE: PRT
<213> ORGANISM: Pinus radiata

<400> SEQUENCE: 98

Met Pro Thr His Ser Gln Arg Phe Pro Phe Asn Gly Trp Ser Met Met
  1               5                  10                  15

Gly Lys Pro Ser Leu Phe Pro Ser Ser Ile Ala Gly Tyr His Glu Lys
                20                  25                  30

Arg Asp Val Glu Ala Leu Leu Thr Phe Arg Lys Gly Ile Thr Leu Asp
            35                  40                  45

Pro Tyr Gly Trp Leu Ser Asn Trp Thr Ala Asn Asn Ser His Asn Val
    50                  55                  60

Cys Leu Trp Asn Gly Ile Ser Cys Ser Pro Asn Thr Asn Arg Val Val
 65                  70                  75                  80

Ser Ile Ser Leu Arg Tyr Gly Arg Leu Asn Gly Thr Leu Ser Pro Tyr
                85                  90                  95

<210> SEQ ID NO 99
<211> LENGTH: 154
<212> TYPE: PRT
<213> ORGANISM: Pinus radiata

<400> SEQUENCE: 99

Met Asp Leu Leu Leu Met Met Met Leu Val Met Met Gly Val Ala
  1               5                  10                  15

Met Pro Thr His Ser Gln Arg Phe Pro Phe Asn Gly Arg Ser Met Met
                20                  25                  30

Gly Lys Pro Ser Leu Phe Pro Ser Ser Ile Ala Gly Tyr His Glu Lys
            35                  40                  45

Arg Asp Val Glu Ala Leu Leu Thr Phe Arg Lys Gly Ile Thr Phe Asp
        50                  55                  60

Pro His Glu Trp Leu Ser Asn Trp Thr Ala Asn Asn Ser His Asn Val
 65                  70                  75                  80

Cys Leu Trp Asn Gly Ile Ser Cys Arg Pro Asn Thr Lys Arg Val Val
                85                  90                  95

Ser Ile Ser Leu Pro Gln Arg Ser Leu Asn Gly Thr Leu Ser Pro Tyr
                100                 105                 110

Ile Gly Asn Leu Ser Leu Leu Gln Gln Leu Asp Leu Ser Phe Asn Ala
```

```
                115                 120                 125
Leu Ser Gly Arg Ile Pro Ala Glu Phe Gly Gln Leu Lys Ala Leu Arg
    130                 135                 140

Thr Phe Glu Val Arg His Asn Ala Leu Ser
145                 150

<210> SEQ ID NO 100
<211> LENGTH: 126
<212> TYPE: PRT
<213> ORGANISM: Eucalyptus grandis

<400> SEQUENCE: 100

Met Ala Ser Cys Gly Gly Leu Val Ser Thr Phe Leu Leu Ala Ile Phe
1               5                   10                  15

Val Thr Gln Ile Val Glu Phe Ser His Ser Ile Ala Ser Thr Asn Val
                20                  25                  30

Ser Cys Ile Gly Val Glu Arg Glu Ala Leu Leu Lys Phe Lys His Gly
            35                  40                  45

Leu Thr Asp Pro Trp Lys Arg Leu Ser Ser Trp Thr Gly Glu Glu Cys
        50                  55                  60

Cys Lys Trp Glu Gly Val Glu Cys Asn Glu Lys Thr Gly His Val Leu
65                  70                  75                  80

Lys Leu Asp Leu His Asn Pro Cys Ile Glu Ile Asp Met Leu Glu
                85                  90                  95

Pro Ser Tyr Lys Cys Arg Leu Gly Gly Asn Ile Val His Ser Leu Thr
            100                 105                 110

Glu Leu Lys Tyr Leu Lys His Leu Asp Leu Ser Ile Asn Asn
        115                 120                 125

<210> SEQ ID NO 101
<211> LENGTH: 128
<212> TYPE: PRT
<213> ORGANISM: Eucalyptus grandis

<400> SEQUENCE: 101

Met Cys Ser Arg Arg Val Val Ser Ser Met Glu Thr Asn Pro Ile His
1               5                   10                  15

Leu Ile Tyr His Val Phe Phe Ile Val Ile Gly Leu Val Ser Val Ser
                20                  25                  30

Ala Ala Glu Gln Ser Ala Ser Ser Arg Lys Thr Asp Ala Glu Ala Leu
            35                  40                  45

Ile Leu Phe Lys Lys Met Ile Gln Lys Asp Pro Ser Gly Val Leu Ser
        50                  55                  60

Gly Trp Gln Leu Asp Gln Asp Leu Cys Ala Trp Tyr Gly Val Thr Cys
65                  70                  75                  80

Tyr Ser Gly Arg Val Thr Gln Leu Asp Leu His Gly Gln Ser Leu Glu
                85                  90                  95

Ala Thr Met Ser Phe Asp Pro Leu Ser Ser Leu Asp Met Leu Thr Val
            100                 105                 110

Ser Ile Cys His Gln Thr Arg Ser Pro Ser Ile Gln Leu Pro Cys Phe
        115                 120                 125

<210> SEQ ID NO 102
<211> LENGTH: 128
<212> TYPE: PRT
<213> ORGANISM: Pinus radiata

<400> SEQUENCE: 102
```

Met Asp Leu Leu Leu Leu Leu Val Met Met Gly Val Ala Met Pro
1               5                   10                  15

Thr His Ser Gln Arg Phe Pro Phe Asn Gly Arg Ser Met Met Gly Lys
                20                  25                  30

Pro Ser Leu Phe Pro Ser Ser Ile Ala Gly Tyr His Glu Lys Arg Asp
                35                  40                  45

Val Glu Ala Leu Leu Ser Phe Arg Lys Gly Ile Ile Ser Asp Pro His
        50                  55                  60

Gly Ser Leu Ser Asp Trp Thr Ala Asn Ser His Asn Val Cys Leu
65                  70                  75                  80

Trp Asn Gly Ile Ser Cys Arg Pro Asn Thr Asn Arg Val Val Ser Ile
                85                  90                  95

Ser Leu Pro Tyr Cys Arg Leu Ser Gly Thr Leu Ser Pro Tyr Ile Gly
                100                 105                 110

Asn Leu Ser Leu Leu Arg Tyr Leu Tyr Leu Ser Asn Asn Asp Leu Ser
                115                 120                 125

<210> SEQ ID NO 103
<211> LENGTH: 153
<212> TYPE: PRT
<213> ORGANISM: Pinus radiata

<400> SEQUENCE: 103

Met Arg Ser Val Phe Arg Ile Ser Ser Leu Leu Val Ile Ser Ile Leu
1               5                   10                  15

Val Leu Leu Thr Leu Ser Ser Ala Ile Asn Asp Asp Ala Glu Met Leu
                20                  25                  30

Leu Ala Phe Lys Ser Ala Met Ser Asp Pro Asp Gly Ala Leu Ala Gly
                35                  40                  45

Trp Thr Glu Ser Asp Ala Ala Asn Phe Cys Gly Trp Thr Gly Val Leu
        50                  55                  60

Cys Asn Glu Phe Asn Arg Thr Ser Ser Leu Asp Leu Thr Asn Met Asn
65                  70                  75                  80

Leu Ser Gly Ile Ile Pro Pro Arg Thr Leu Ser Ser Leu Asp Ser Leu
                85                  90                  95

Val Asn Leu Ser Leu Ala Leu Asn Lys Phe Ser Thr Pro Phe Pro Ser
                100                 105                 110

Ala Ile Leu Asp Ile Ser Thr Leu Arg Phe Leu Asn Ile Ser Asn Asn
                115                 120                 125

Asn Phe Ser Gly Glu Ile Pro Ala Asn Ile Ser Arg Leu Val Asn Leu
                130                 135                 140

Glu Leu Leu Asp Thr Tyr Asn Asn Asn
145                 150

<210> SEQ ID NO 104
<211> LENGTH: 173
<212> TYPE: PRT
<213> ORGANISM: Pinus radiata

<400> SEQUENCE: 104

Met Ala Pro Leu Leu Gly Ile Leu Leu Leu His Ala Leu Ile Phe Ser
1               5                   10                  15

Tyr Gly Glu Glu Ala His Val Ala Gly Ser Asn His Thr Glu Val Arg
                20                  25                  30

Ala Leu Met Ala Leu Lys Ala Gly Ile Val Asp Thr Ser Gly His Leu
                35                  40                  45

```
Ser Asp Trp Glu Val His Gly Asp Glu Leu Ser Ala Ser Pro Cys Ser
    50                  55                  60

Trp Thr Gly Val Phe Cys Asp Leu Glu Ser Glu Asn Val Thr Glu Leu
 65                  70                  75                  80

Asp Leu Ser Arg Met Asn Leu Thr Gly Thr Ile Ser Asp Glu Ile Arg
                 85                  90                  95

Glu Leu Gln His Leu Lys Val Leu Asn Ile Ser Phe Asn Gln Phe Ser
            100                 105                 110

Gly Ala Phe Pro Val Val Ile Phe Asn Leu Thr Arg Leu Arg Ser Leu
            115                 120                 125

Asp Ile Asn His Asn Ser Phe Glu Gly Tyr Phe Pro Ala Gly Ile Ser
130                 135                 140

Lys Met Lys Asn Leu Val Asn Phe Ile Ala Phe Ser Asn Ser Phe Lys
145                 150                 155                 160

Gly Pro Leu Pro Leu Glu Phe Val Glu Met Leu Phe Trp
                165                 170
```

<210> SEQ ID NO 105
<211> LENGTH: 247
<212> TYPE: PRT
<213> ORGANISM: Eucalyptus grandis

<400> SEQUENCE: 105

```
Met Ala Ala Pro Ser Ser Ala Ala Ser Ala Ala Val Phe Ala Leu
  1               5                  10                  15

His Ser Leu Leu Leu Leu Leu Leu Ala Ala Ala Val Glu Asp Asp
             20                  25                  30

Val Leu Cys Leu Glu Gly Val Lys Arg Ser Leu Gly Asp Pro Gln Gly
             35                  40                  45

Ser Leu Ala Asp Trp Thr Phe Ala Asn Thr Ser Ala Ser His Ile Cys
    50                  55                  60

Asn Leu Asn Gly Val Ala Cys Trp Asn Leu Asn Glu Asn Arg Ile Ile
 65                  70                  75                  80

Ser Leu Ser Leu Thr Gly Phe Gly Val Ser Gly Leu Pro Glu Ser
                 85                  90                  95

Leu Lys Asn Cys His Ser Leu Gln Thr Leu Asp Leu Ser Gln Asn Lys
            100                 105                 110

Leu Asp Gly Pro Ile Pro Ala Gln Ile Cys Glu Trp Leu Pro Tyr Leu
            115                 120                 125

Val Lys Leu Asp Leu Ser Ser Asn Ser Leu Ala Gly Pro Ile Pro Ser
130                 135                 140

Gln Ile Gly Asp Cys Lys Phe Leu Asn Asn Leu Ile Leu Asn Asp Asn
145                 150                 155                 160

Lys Leu Thr Gly Pro Ile Pro Tyr Glu Val Gly Arg Leu Asp Arg Leu
                165                 170                 175

Lys Val Phe Ser Val Arg Gly Asn Asp Leu Ser Gly Ile Pro Ser
                180                 185                 190

Glu Leu Ser Lys Phe Ser Ser Asp Phe Ser Asp Asn Asp Asp Leu
            195                 200                 205

Cys Gly Arg Pro Leu Gly Ser Cys Gly Leu Ser Lys Lys Ser Leu
    210                 215                 220

Ala Ile Ile Ile Ala Ala Gly Val Leu Gly Ala Ala Ser Leu Leu
225                 230                 235                 240

Leu Gly Phe Ala Leu Trp Trp
```

```
<210> SEQ ID NO 106
<211> LENGTH: 145
<212> TYPE: PRT
<213> ORGANISM: Pinus radiata

<400> SEQUENCE: 106

Met Asp Leu Leu Leu Leu Val Met Met Phe Val Cys Ser Val Met
1               5                   10                  15

Met Gly Val Ala Met Pro Thr Asp Gly Phe Thr Ser Val Glu Ser Val
            20                  25                  30

Pro Phe Asn Gly Arg Asn Arg His Lys Arg Asp Val Glu Ala Leu Leu
        35                  40                  45

Ser Phe Lys Glu Ser Ile Ile Ser Asp Pro Tyr Gly Ser Leu Thr Asn
    50                  55                  60

Trp Thr Ala Asn Asn Ser His Asn Val Cys Leu Trp Asn Gly Ile Ser
65                  70                  75                  80

Cys Arg Pro Asn Thr Lys Arg Val Val Ser Ile Ser Leu Pro Glu Cys
                85                  90                  95

Trp Leu Asn Gly Thr Leu Ser Pro Tyr Ile Gly Asn Leu Ser Leu Leu
            100                 105                 110

Arg His Leu Asp Leu Ser Trp Asn Ala Leu Ser Gly Arg Ile Pro Ala
        115                 120                 125

Glu Phe Gly Gln Leu Lys Ala Leu Arg Ile Leu Asp Leu Ser Ala Ser
    130                 135                 140

His
145

<210> SEQ ID NO 107
<211> LENGTH: 150
<212> TYPE: PRT
<213> ORGANISM: Pinus radiata

<400> SEQUENCE: 107

Met Ala Pro Ser Thr Asp Phe Ile Leu Ile Thr Ser Thr Leu Met Leu
1               5                   10                  15

Ile Phe Val Ser Ala Asn Ala His Leu Leu His His Tyr His Glu Lys
            20                  25                  30

Ser Arg Glu Arg Leu Gln Val Asp Ile Glu Ala Leu Gln Ala Phe Lys
        35                  40                  45

Ala Ser Leu Thr Tyr Asp Pro Ser His Ala Leu Ala Asn Trp Asp Phe
    50                  55                  60

Val Ala Asn His Val Cys Asn Trp Thr Gly Val Thr Cys Asn Pro His
65                  70                  75                  80

Lys Leu Arg Val Ser Ala Leu Asn Leu Tyr Asn Met Ser Leu Gln Gly
                85                  90                  95

Thr Ile Pro Pro His Leu Gly Asn Ile Ser Phe Leu Gly Val Leu Asn
            100                 105                 110

Leu Thr Leu Asn Ser Phe Ser Gly Ile Ile Pro Asn Glu Leu Gly Lys
        115                 120                 125

Leu Arg Arg Leu Lys Arg Leu Ser Leu Lys Gln Asn Gln Leu Ile Ser
    130                 135                 140

Ser Ile Pro Arg Leu Lys
145             150
```

```
<210> SEQ ID NO 108
<211> LENGTH: 126
<212> TYPE: PRT
<213> ORGANISM: Pinus radiata

<400> SEQUENCE: 108
```

Met Arg Met Phe Leu Leu Leu Val Tyr Leu Phe Pro Leu Val Thr Pro
 1               5                  10                  15

Phe Ala Phe Ser Thr Val Gln Leu Ser Asn Gly Ser Asn Ala Val Asp
                20                  25                  30

Gln Glu Ala Val Leu Gly Phe Leu Ser Ala Ile Thr Asn Asp Pro Tyr
            35                  40                  45

Gln Ser Leu Pro Thr Asn Trp Lys Ser Asn Val Ser Val Cys Glu Trp
        50                  55                  60

Thr Ile Ile Lys Cys Asn Gly Ser Arg Val Val Ser Leu Asn Val Ser
65                  70                  75                  80

Ser Met Gly Leu Glu Gly Thr Ile Ser Pro Leu Leu Gly Asn Leu Ser
                85                  90                  95

Phe Leu Glu Lys Leu Asp Leu Arg Asn Asn Asn Phe His Gly Pro Ile
            100                 105                 110

Pro Tyr Gln Leu Gly Ser Leu Val Arg Leu Gln Met Leu Ile
        115                 120                 125

```
<210> SEQ ID NO 109
<211> LENGTH: 118
<212> TYPE: PRT
<213> ORGANISM: Eucalyptus grandis

<400> SEQUENCE: 109
```

Met Glu Ser Cys Asn Cys Val Glu Pro Gln Trp Pro Ala Asp Glu Leu
 1               5                  10                  15

Leu Met Lys Tyr Gln Tyr Leu Ser Asp Phe Phe Ile Ala Leu Ala Tyr
                20                  25                  30

Phe Ser Ile Pro Leu Glu Leu Ile Tyr Phe Val Lys Lys Ser Ala Val
            35                  40                  45

Phe Pro Tyr Arg Trp Val Leu Val Gln Phe Gly Ala Phe Ile Val Leu
        50                  55                  60

Cys Gly Ala Thr His Leu Ile Asn Leu Trp Thr Phe Ala Ile His Ser
65                  70                  75                  80

Arg Thr Val Ala Tyr Val Met Thr Ile Ala Lys Val Leu Thr Ala Ala
                85                  90                  95

Val Ser Cys Ile Thr Ala Leu Met Leu Val His Ile Ile Pro Asp Leu
            100                 105                 110

Leu Ser Val Lys Thr Arg
        115

```
<210> SEQ ID NO 110
<211> LENGTH: 132
<212> TYPE: PRT
<213> ORGANISM: Pinus radiata

<400> SEQUENCE: 110
```

Phe Val Ser Asn Ala His Phe Tyr Leu Lys Val Gln Val Lys Asp Ser
 1               5                  10                  15

Gly Cys Gly Ile Gln Pro Gln Asp Ile Pro Gln Ile Phe Thr Arg Phe
                20                  25                  30

Ile His Pro Arg Ser Gly Ser Asn Arg Gly Asn Gly Ser Gly Gly Leu
            35                  40                  45

```
Gly Leu Ala Ile Cys Lys Arg Phe Ile Asn Leu Met Gly Gly His Ile
    50                  55                  60

Ser Ile Glu Ser Glu Gly His Asp Lys Gly Thr Ile Val Thr Phe Val
 65                  70                  75                  80

Val Lys Leu Gln Lys Cys Ser Asn Ala Asn Asp Ser Ala Ala His Glu
                 85                  90                  95

Ile Thr Ser Arg Ala Gln Ser Ile His Glu Ser Thr His Phe Ala Arg
                100                 105                 110

His Lys Pro Leu Ile Asp Thr Asp Arg Thr Val Pro Ser Ser Ser Gln
            115                 120                 125

Tyr Gln Arg Ser
            130

<210> SEQ ID NO 111
<211> LENGTH: 117
<212> TYPE: PRT
<213> ORGANISM: Pinus radiata

<400> SEQUENCE: 111

Ile Leu Ser Lys Arg Trp Tyr Ala Leu Met Val Leu Met Leu Pro Ser
  1               5                  10                  15

Asp Ser Ala Arg Arg Trp His Val His Glu Leu Glu Leu Val Glu Val
                 20                  25                  30

Val Ala Asp Gln Val Ala Val Ala Leu Ser His Ala Ala Ile Leu Glu
             35                  40                  45

Glu Ser Met Arg Ala Arg Asp Leu Leu Met Glu Gln Asn Val Ala Leu
 50                  55                  60

Glu Ile Ala Arg Gln Glu Ala Glu Thr Ala Ile Arg Ala Arg Asn Asp
 65                  70                  75                  80

Phe Leu Ala Val Met Asn His Glu Met Arg Thr Pro Met His Ala Ile
                 85                  90                  95

Ile Ala Leu Ser Ser Leu Leu Gln Glu Thr Glu Leu Thr Pro Glu Gln
                100                 105                 110

Arg Ser Met Val Glu
            115

<210> SEQ ID NO 112
<211> LENGTH: 232
<212> TYPE: PRT
<213> ORGANISM: Pinus radiata

<400> SEQUENCE: 112

Val Ala Thr Pro Ser Ser His Ser Cys Ser Ser Phe Pro Leu Leu Pro
  1               5                  10                  15

Ser Thr Thr Val Thr Thr Arg Asp Arg Ser Ala Ser Asn Ala Ser Ser
                 20                  25                  30

Ser Ser Gly Thr Ser Ser Thr Cys Val Ser Thr Ser Tyr Gly Ala Ile
             35                  40                  45

Ala Thr Gly Ser Asp Asn Ala Ile Glu Gly Ser Pro Pro Ala Ala
 50                  55                  60

Val Ala Ala Ala Ile Met Thr Pro Ser Ser Asp Gln His His Leu
 65                  70                  75                  80

His Ala Pro Gln Pro Ile Asn Val Gly Asn Thr Cys Ala Val Ala Met
                 85                  90                  95

Asp Thr Leu Ala Gln His Ser Cys Ser Ser Gly Met Ala Ser Pro Pro
                100                 105                 110
```

```
Ser Thr Pro Thr Gly Ile Thr Asn Val Ala Arg Leu Thr Met Arg Ala
        115                 120                 125

Gly Ala Gly Gly Asp Gly Asp Ser His Ala Leu Ala Leu Gly Ser Asp
130                 135                 140

Pro Ile Ala Thr Gln Ser Pro Ser Thr Lys Arg Arg Ala Ala Ser Ala
145                 150                 155                 160

Pro Trp Pro Trp Ala Tyr Thr Arg Val Pro Ile Val Ala Ala Thr Ala
                165                 170                 175

Gly Ala Leu Glu Glu Glu Gln Lys Glu Cys Ile Gln Ala Gly Met Asp
            180                 185                 190

Asp Val Leu Thr Lys Pro Ile Asp Arg Tyr Gln Leu Gln Arg Lys Leu
        195                 200                 205

Ala Arg Phe Ser Pro Arg Phe Thr Ser Leu Val Val Ala Ser Ser Ala
210                 215                 220

Pro Ala Ser Gln Gln Ala His Gln
225                 230

<210> SEQ ID NO 113
<211> LENGTH: 166
<212> TYPE: PRT
<213> ORGANISM: Pinus radiata

<400> SEQUENCE: 113

Thr Arg Val Leu Leu Ile Asp Asp His Pro Leu Phe Arg Glu Gly Leu
1               5                   10                  15

Ala Gly Ala Ile Gln Ala Glu Pro Asp Phe Glu Val Val Gly Gln Ala
            20                  25                  30

Gly Thr Val Asp Glu Leu Arg Gly Leu Ala Pro Gln Ile Glu Pro Asp
        35                  40                  45

Val Ala Ile Val Asp Leu Leu Met Pro Ser Val Ser Gly Ile Gly Val
    50                  55                  60

Thr Arg Glu Leu Cys Glu Leu Leu Pro Arg Cys Arg Val Leu Gly Leu
65                  70                  75                  80

Ser Ala Val Val Asp Ala Ala Ile Ala Glu Met Leu Arg Ala Gly
                85                  90                  95

Ala Ser Gly Phe Ala Leu Lys Thr Gln Pro Ala Pro Asp Ile Leu Asp
            100                 105                 110

Ala Val Arg Arg Thr Val Ala Gly Glu Ser Tyr Leu Pro Pro Ser Val
        115                 120                 125

Ser Arg Glu Ala Ile Asp Ala Glu Leu Ala Gly Gly Ala Pro Pro Ser
    130                 135                 140

Leu Ala Gln Leu Thr Lys Ala Arg Ala Arg Asp Leu Arg Ala Asp Asp
145                 150                 155                 160

Pro Arg Leu His Gln Ser
                165

<210> SEQ ID NO 114
<211> LENGTH: 762
<212> TYPE: PRT
<213> ORGANISM: Pinus radiata

<400> SEQUENCE: 114

Met Ile Cys Leu Gly Gly Ile Val Ile Ser Phe Leu Leu Gln Asn
1               5                   10                  15

Ile Ala Met Ala Ser Glu Asp Gly Gly Ser Arg Cys Asn Cys Asp Gly
            20                  25                  30
```

-continued

```
Glu Gly Trp Trp Asn Val Glu Asn Ile Met Gln Cys Gln Met Val Ser
         35                  40                  45
Asp Phe Leu Ile Ala Leu Ala Tyr Phe Ser Ile Pro Leu Glu Leu Leu
 50                  55                  60
Tyr Phe Leu Ser Cys Ser Asn Ser Leu Pro Phe Arg Trp Val Ile Val
 65                  70                  75                  80
Gln Phe Gly Ala Phe Ile Val Leu Cys Gly Leu Thr His Phe Ile Asn
                 85                  90                  95
Ile Trp Thr Tyr Gly Pro Gln Ser Phe His Val Met Leu Ala Leu Thr
                100                 105                 110
Ile Phe Lys Phe Leu Thr Ala Leu Val Ser Cys Ala Thr Ala Ile Thr
            115                 120                 125
Leu Val Thr Leu Ile Pro Glu Leu Leu Arg Val Lys Val Arg Glu Ile
        130                 135                 140
Phe Leu Lys Asn Lys Ala Arg Glu Leu Asp Arg Glu Val Asp Ile Val
145                 150                 155                 160
Lys Arg Lys Glu Glu Thr Ser Trp His Val His Met Leu Thr Gln Glu
                165                 170                 175
Ile Arg Ser Ser Leu Asp Arg His Thr Ile Leu Asn Thr Thr Leu Ile
                180                 185                 190
Ser Leu Ala Lys Thr Leu Asn Leu Glu Asn Cys Thr Ile Trp Met Pro
            195                 200                 205
Leu Ala Asp Gly Thr Ala Met Glu Val Ser His Glu Leu Lys Arg Arg
        210                 215                 220
His Leu Gln Val Pro Leu Thr Val Pro Thr Thr Asp Pro Asp Val Lys
225                 230                 235                 240
Lys Ile Met His Ser Glu Asp Ala Ile Leu Leu Ser Pro Asp Ser Ala
                245                 250                 255
Leu Gly Lys Glu Ser Asn His His Trp Ser Leu Ala Gly Pro Val Ala
                260                 265                 270
Ala Ile Arg Val Pro Leu Trp Lys Ala Ser Asn Phe Lys Ser Gly Ala
            275                 280                 285
Ser Val Asp Arg Glu Glu Ser Tyr Ala Ile Met Val Leu Val Leu Pro
        290                 295                 300
Cys Glu Asp Glu Arg Gln Trp Ser Ser Gln Glu Leu Tyr Ile Val Lys
305                 310                 315                 320
Asp Val Ala Glu Gln Val Ala Val Ala Leu Ser His Ala Ala Val Leu
                325                 330                 335
Glu Glu Ser Gln Lys Leu Lys Ala Pro Leu Ile Asp Lys Asn Lys Thr
                340                 345                 350
Leu Gln Gln Ala Lys Gln Asp Ala Leu Arg Ala Ser Lys Ala Arg His
            355                 360                 365
Ser Phe Gln Leu Ala Met Asn Arg Glu Met Arg Leu Pro Met His Ala
        370                 375                 380
Ile Ser Ala Leu Ser Ser Ile Leu Gln Ser Ala Arg Leu Asn Val Glu
385                 390                 395                 400
Gln Leu Ala Met Thr Asn Met Leu Ala Lys Ser Ser Ser Leu Leu Ser
                405                 410                 415
Thr Leu Ile Asn Asp Ile Met Asp Phe Ser Glu Leu Glu Asp Thr Ser
                420                 425                 430
Leu Val Leu Gln Leu His Pro Phe Gln Leu His Gly Met Leu Lys Asp
            435                 440                 445
```

```
Ala Ala His Leu Thr Glu Thr Met Ser Arg Ser Lys Gly Leu Leu Leu
        450                 455                 460

Asn Val Glu Ile Gly Asp Gly Met Pro Asp His Val Ile Gly Asp Glu
465                 470                 475                 480

Lys Arg Ile Leu Arg Ile Ile Leu His Met Val Gly Asn Ala Ile Asn
                    485                 490                 495

Ser Thr Lys Gln Gly Thr Ile Ser Ile Arg Ile Cys Val Glu Asp Arg
                500                 505                 510

Ala Glu Gly Trp Trp Asp Pro Asn Asn Arg Arg Trp Arg Pro Ser Leu
            515                 520                 525

Cys Glu Gly Phe Thr Tyr Leu Arg Phe Glu Ile Arg Thr Ser Gly Ser
        530                 535                 540

Gly Ser Ile Gln Asn Asp Asn Pro Ser Phe Leu Thr Val Val Gln Asp
545                 550                 555                 560

Gly Lys Ser Asp Ser Ser Ser Thr Gly Glu Gly Leu Gly Phe Ala
                565                 570                 575

Ile Cys Lys Lys Phe Val Gln Leu Met His Gly Asn Ile Trp Leu Glu
                580                 585                 590

Pro Asn Ser Lys Gly Glu Gly Ser Val Val Thr Phe Leu Ile Arg Val
            595                 600                 605

Gln Leu Gln Thr Ser Thr Ala Asn Lys His Trp Leu Ser Pro Asp Glu
        610                 615                 620

Lys Ile Tyr Lys Ser Ser Phe Lys Gly Leu Lys Val Leu Val Ala Asp
625                 630                 635                 640

Asp Asn Asn Val Ser Arg Ser Val Thr Arg Arg Leu Leu Gln Glu Leu
                    645                 650                 655

Gly Cys Gln Thr Thr Glu Val Asp Ser Gly Tyr Arg Cys Leu Met Thr
                660                 665                 670

Leu Leu Gln Ser Gly Ser Ala Phe Gln Leu Val Phe Leu Glu Val Cys
            675                 680                 685

Leu Ala Gln Met Asp Gly Tyr Glu Val Ala Phe Arg Ile Arg Gln Lys
        690                 695                 700

Phe Arg Ser Arg Asn Arg Pro Leu Val Val Ala Leu Thr Ala Ser Thr
705                 710                 715                 720

Asp Lys Glu Thr Met Glu Arg Cys Leu Gln Thr Gly Met Asp Gly Val
                725                 730                 735

Ile Arg Lys Pro Val Thr Leu Arg Glu Met Ser Asn Glu Leu Phe Lys
                740                 745                 750

Ile Val His Gln Thr Asn Asn Ile His Glu
            755                 760

<210> SEQ ID NO 115
<211> LENGTH: 158
<212> TYPE: PRT
<213> ORGANISM: Eucalyptus grandis

<400> SEQUENCE: 115

Thr Met Arg Ala Lys Gln Met Leu Ala Thr Met Ser His Glu Ile Arg
  1               5                  10                  15

Ser Pro Leu Ala Gly Val Val Ser Met Ala Glu Ile Leu Ala Gln Thr
                20                  25                  30

Arg Leu Asp His Glu Gln Arg Gln Leu Leu Asp Val Met Leu Ser Ser
            35                  40                  45

Gly Asp Leu Val Leu Gln Leu Ile Asn Asp Ile Leu Asp Leu Ser Lys
        50                  55                  60
```

-continued

Val Glu Ser Gly Val Met Lys Leu Glu Ala Thr Lys Phe Arg Pro Arg
65                  70                  75                  80

Glu Val Val Lys His Val Leu Gln Thr Ala Ala Ser Leu Arg Lys
                85                  90                  95

Ile Leu Thr Leu Glu Gly His Val Ala Asp Val Pro Ile Glu Val
                100                 105                 110

Ile Gly Asp Val Leu Arg Ile Arg Gln Ile Leu Thr Asn Leu Ile Ser
            115                 120                 125

Asn Ala Ile Lys Phe Thr His Glu Gly Lys Val Gly Ile Asn Leu Tyr
        130                 135                 140

Val Val Pro Glu Pro Ser Val Glu Lys Thr Glu Glu Cys Pro
145                 150                 155

<210> SEQ ID NO 116
<211> LENGTH: 170
<212> TYPE: PRT
<213> ORGANISM: Eucalyptus grandis

<400> SEQUENCE: 116

Lys Ile Glu Ile Glu Ala Val Gln Phe Asp Leu Arg Ala Ile Leu Asp
1               5                   10                  15

Asp Val Leu Ser Leu Phe Ser Gly Lys Ser Gln Glu Lys Arg Val Glu
                20                  25                  30

Leu Ala Val Tyr Ile Ser Glu Asn Val Pro Glu Lys Leu Ile Gly Asp
            35                  40                  45

Pro Gly Arg Phe Arg Gln Ile Ile Thr Asn Leu Met Gly Asn Ser Ile
        50                  55                  60

Lys Phe Thr Glu Lys Gly His Ile Leu Val Thr Val His Leu Val Asp
65                  70                  75                  80

Glu Val Met Asn Ser Thr Asp Ala Glu Met Glu Ser Ala Thr Arg Ser
                85                  90                  95

Thr Leu Ser Gly Phe Pro Val Pro Asp Arg Arg Leu Ser Trp Ala Lys
                100                 105                 110

Phe Arg Thr Phe Ser Gln Glu Gly Pro Ala Ser Pro Val Pro Ser Ser
            115                 120                 125

Phe Ser Asn Pro Ile Asn Leu Ile Ile Ser Val Glu Asp Thr Gly Ile
        130                 135                 140

Gly Ile Pro Pro Glu Ala Gln Pro Arg Val Phe Thr Arg Phe Met Gln
145                 150                 155                 160

Val Gly Pro Ser Ile Ser Arg Thr His Gly
                165                 170

<210> SEQ ID NO 117
<211> LENGTH: 599
<212> TYPE: PRT
<213> ORGANISM: Eucalyptus grandis

<400> SEQUENCE: 117

Leu Glu His Lys Ile Ser Ile Ser Ser Leu Lys Thr Lys Leu Lys Gln
1               5                   10                  15

His Gly Ser His Ala Arg Arg Ala Ser Lys Lys Asp Asn Lys Val Thr
                20                  25                  30

Leu Trp Phe Glu Val Asp Asp Thr Gly Cys Gly Ile Asp Pro Ser Lys
            35                  40                  45

Trp Glu Ser Val Phe Glu Ser Phe Glu Gln Ala Asp Pro Ser Thr Thr
        50                  55                  60

-continued

```
Arg Leu His Gly Gly Thr Gly Leu Gly Leu Cys Ile Val Arg Thr Leu
 65                  70                  75                  80

Val Asn Lys Met Gly Gly Glu Ile Lys Val Ile Lys Lys Asn Gly Pro
                 85                  90                  95

Gly Thr Leu Met Arg Leu Tyr Leu Leu Asn Ala Pro Val Asp Gly
                100                 105                 110

Thr Glu His Asn Cys Ser Val Asp Tyr Ala Val His Asn Ile Arg Val
            115                 120                 125

Leu Leu Ala Gln His Gly Ser Thr Gly Arg Phe Ile Met Ser Gly Trp
        130                 135                 140

Leu Arg Arg Asn Gly Val Ser Thr Leu Glu Ala Ser Gly Trp Asn Glu
145                 150                 155                 160

Leu Thr Gln Ile Leu Gln Glu Leu Tyr Gln Gly Arg Asn Ser Gly Ala
                165                 170                 175

Pro Tyr Arg Thr Val Asn Thr Glu His Ala His Glu Leu Pro Arg Ser
                180                 185                 190

Glu Val Thr Thr Phe Asp Asp Ile Gln Ser Glu Ile Leu Ile Ile Val
            195                 200                 205

Val Asp Ile Glu Leu Leu Asp Leu Asn Thr Asp Ile Trp Lys Glu Gln
210                 215                 220

Leu Asn Phe Leu Asp Lys Tyr His Arg Lys Ala Lys Phe Ala Trp Met
225                 230                 235                 240

Leu Asn His Asp Thr Phe Asn Ala Ile Lys Val Glu Leu Arg Arg Lys
                245                 250                 255

Gly His Met Leu Met Val Asn Lys Pro Leu Tyr Lys Ala Lys Met Ile
                260                 265                 270

Gln Ile Leu Asp Ala Ala Ile Lys Glu Arg Asn Ser Glu Leu Leu Lys
            275                 280                 285

Arg Ala Ser Asn Ser Ser Lys Ser Met Asn Lys Glu Glu Asp Leu His
290                 295                 300

Glu Cys Leu Glu Ile Asp Ser Glu His Tyr Glu Gly Ala Ser Ser Asp
305                 310                 315                 320

Glu Leu Asp Thr Val Glu Thr Ser Arg Ser Gly Cys Thr Asn Thr Ser
                325                 330                 335

Pro Gly Glu Gln Lys Gln Gln Glu Gly Ile Lys Thr Pro Pro Ala Leu
                340                 345                 350

Gln His Arg Thr Ser Asn Tyr His Ser Phe Asn Ser Thr Leu Leu Ser
            355                 360                 365

Ser Asp Tyr Asn Asn Leu Gly Asn Lys Glu Glu Ala Cys Pro Thr Ser
370                 375                 380

Pro Pro Leu Asp His Pro Asp Asn Ala Glu Gly Arg Phe Lys Cys Thr
385                 390                 395                 400

Arg Ser Val Phe Ser Ser Lys Glu Lys Glu Asp Gly Asn Ser Glu Ala
                405                 410                 415

Gln Glu Gln Leu Leu Ile Ser Lys Arg Pro Pro Ala Lys Val Asp Ser
            420                 425                 430

Cys Ser Ser Lys Glu Leu Asp Gln Lys Gly Ser Leu Glu Gly Leu Cys
        435                 440                 445

Ile Leu Leu Ala Glu Asp Thr Pro Val Leu Gln Arg Val Ala Thr Ile
        450                 455                 460

Met Leu Glu Lys Leu Gly Ala Lys Val Ile Ala Val Gly Asp Gly Leu
465                 470                 475                 480
```

```
Gln Ala Val Asn Ala Leu Asn Ser Ser Leu Asp Val Asp Ala Glu Asp
                485                 490                 495

Phe Arg Thr Thr Leu His Leu Gln Asn Ala Asn Arg Met Pro Gln Ala
                500                 505                 510

Gly Thr Arg Ser Trp Gln Pro Tyr Asp Leu Ile Leu Met Asp Cys Gln
                515                 520                 525

Met Pro Gln Met Asp Gly Tyr Glu Ala Thr Lys Ala Ile Arg Arg Ser
            530                 535                 540

Glu Ala Gly Ser Gly Leu His Ile Pro Ile Val Ala Leu Thr Ala His
545                 550                 555                 560

Ala Met Ser Ser Asp Glu Ala Lys Cys Leu Glu Val Gly Met Asp Ala
                565                 570                 575

Tyr Leu Thr Lys Pro Ile Asp Tyr Lys Leu Met Val Ser Thr Ile Leu
                580                 585                 590

Ser Leu Thr Lys Gly Val Asn
            595

<210> SEQ ID NO 118
<211> LENGTH: 153
<212> TYPE: PRT
<213> ORGANISM: Eucalyptus grandis

<400> SEQUENCE: 118

Leu Ser Thr Gly Ala Ser Ser Ala Thr Thr Gly Met Ala Ser Asn Gly
1               5                   10                  15

Leu Val Ser Pro Arg Arg Ser Ser Gly Gln Phe Asp Gly Ser Asp
                20                  25                  30

Pro Ser Pro Cys Gly Ser Glu Glu Val His Val Leu Ala Val Asp Asp
            35                  40                  45

Ser Leu Val Asp Arg Lys Val Ile Glu Arg Leu Leu Lys Ile Thr Ser
        50                  55                  60

Cys Lys Val Thr Ala Val Asp Ser Gly Leu Arg Ala Leu Arg Tyr Leu
65                  70                  75                  80

Gly Leu Asp Glu Glu Lys Thr Ala Gly Asp Phe Asn Gly Leu Lys Val
                85                  90                  95

Asp Met Ile Ile Thr Asp Tyr Cys Met Pro Gly Met Thr Gly Tyr Glu
            100                 105                 110

Leu Leu Lys Lys Ile Lys Glu Ser Ser Ala Leu Arg Glu Ile Pro Val
            115                 120                 125

Val Ile Met Ser Ser Glu Asn Val Leu Ala Arg Ile Asp Arg Cys Met
        130                 135                 140

Glu Glu Gly Ala Glu Asp Phe Ile Val
145                 150

<210> SEQ ID NO 119
<211> LENGTH: 190
<212> TYPE: PRT
<213> ORGANISM: Eucalyptus grandis

<400> SEQUENCE: 119

Ile Ile Ser Ser Cys Ala Ser Ser Val Lys Thr Gly Met Ala Arg Asn
1               5                   10                  15

Gly Val Ala Ser Trp Arg Arg Ser Ser Asp Gln Phe Asp Asp Pro
                20                  25                  30

Ser Pro Cys Gly Ser Glu Asp Val His Val Leu Ala Val Asp Asp Ser
            35                  40                  45
```

```
Leu Val Asp Arg Lys Val Ile Glu His Leu Leu Lys Ile Ser Ser Cys
     50                  55                  60

Lys Val Thr Ala Val Asp Ser Gly Ile Arg Ala Leu Gln Phe Leu Gly
 65                  70                  75                  80

Leu Asp Glu Glu Lys Ala Ala Gly Asp Phe Asn Gly Leu Lys Val Asp
                 85                  90                  95

Leu Ile Ile Thr Asp Tyr Cys Met Pro Gly Met Thr Gly Tyr Glu Leu
            100                 105                 110

Leu Lys Lys Ile Lys Glu Ser Ser Ala Leu Arg Glu Ile Pro Val Val
                115                 120                 125

Ile Met Ser Ser Glu Asn Val Leu Ala Arg Ile Asp Arg Cys Leu Glu
            130                 135                 140

Glu Gly Ala Glu Asp Phe Ile Val Lys Pro Val Lys Leu Ser Asp Val
145                 150                 155                 160

Lys Arg Leu Arg Asp Phe Met Thr Arg Asp Val Gly Asp Arg Val Arg
                165                 170                 175

Ser Asp Gly Glu Gly Thr Thr His Lys Arg Lys Leu Gln Glu
                180                 185                 190

<210> SEQ ID NO 120
<211> LENGTH: 206
<212> TYPE: PRT
<213> ORGANISM: Pinus radiata

<400> SEQUENCE: 120

Ala Ala Ala Ser Thr Glu Asp Thr Gly Ile Gly Ile Pro Leu Pro Ala
 1               5                  10                  15

Gln His Arg Val Phe Thr Pro Phe Met Gln Ala Asp Ser Ser Thr Ser
                 20                  25                  30

Arg Thr Tyr Gly Gly Thr Gly Ile Gly Leu Ser Ile Ser Arg Cys Leu
             35                  40                  45

Ile Glu Leu Met Gly Gly Glu Ile Arg Phe Ile Ser Arg Pro Gly Ile
         50                  55                  60

Gly Ser Thr Phe Ser Phe Thr Ala Leu Phe Lys Val Gly Gln Ala Gly
 65                  70                  75                  80

Ala Asp Gly Asp Gly Asp Leu Leu Arg Gly Ala Arg Leu Pro Thr His
                 85                  90                  95

Phe Lys Gly Met Lys Ala Leu Val Leu Asp Gly Asn Pro Val Cys Ser
            100                 105                 110

Leu Val Thr Lys Tyr His Leu Gln Arg Phe Gly Ile Glu Val Asp Ser
            115                 120                 125

Ile Thr Ser Ser Lys Val Ala Leu Ser Met Leu Asn Gly Met Asp Gly
            130                 135                 140

Phe Pro Thr Glu Gly Cys Ser Val Lys Asp Gly Ile Asp Met Val Leu
145                 150                 155                 160

Ile Glu Lys Asp Ala Trp Gly Ser Arg His Trp His Leu Ile Ser Phe
                165                 170                 175

Ala Ser Thr Ser Arg Ser Leu Ser Lys Arg Thr Leu Ser Thr Val Lys
                180                 185                 190

Gly Phe Ile Lys Asp Asp Ser Phe Gly Tyr Ile Ala Asp Ser
            195                 200                 205

<210> SEQ ID NO 121
<211> LENGTH: 123
<212> TYPE: PRT
<213> ORGANISM: Pinus radiata
```

<400> SEQUENCE: 121

Ser Lys Gly Leu Leu Lys Ile Ile Leu Leu Ala Thr Ser Leu Thr Ala
1               5                   10                  15

Glu Glu Thr Gln Lys Ala Lys Ala Ala Gly Phe Ala Glu Thr Val Ile
            20                  25                  30

Leu Lys Pro Leu Arg Ala Ser Val Phe Ala Val Arg Leu Gln Leu Ala
        35                  40                  45

Leu Gly Phe Cys Tyr Arg Arg Glu His Leu Arg Glu Pro Leu Lys Thr
    50                  55                  60

Ser Ser Pro Leu Ser Asn Val Leu Ser Gly Lys Gly Ile Leu Val Val
65                  70                  75                  80

Asp Asp Asn Ile Val Asn Arg Arg Val Ala Ala Gly Ala Leu Lys Lys
                85                  90                  95

Tyr Gly Ala Asn Val Ile Cys Thr Asp Gly Gly Lys Ser Ala Ile Ser
            100                 105                 110

Met Leu Arg Gln Pro His Asn Leu Ile Thr Ser
        115                 120

<210> SEQ ID NO 122
<211> LENGTH: 142
<212> TYPE: PRT
<213> ORGANISM: Eucalyptus grandis

<400> SEQUENCE: 122

Met Ala Ser Asn Gly Leu Val Ser Pro Arg Arg Ser Ser Asp Gln
1               5                   10                  15

Phe Asp Gly Ser Asp Pro Ser Pro Cys Gly Ser Glu Glu Val His Val
            20                  25                  30

Leu Ala Val Asp Asp Ser Leu Val Asp Arg Lys Val Ile Glu Arg Leu
        35                  40                  45

Leu Lys Ile Thr Ser Cys Lys Val Thr Ala Val Asp Ser Gly Leu Arg
    50                  55                  60

Ala Leu Arg Tyr Leu Gly Leu Asp Glu Glu Lys Thr Ala Gly Asp Phe
65                  70                  75                  80

Asn Gly Leu Lys Val Asp Met Ile Ile Thr Asp Tyr Cys Met Pro Gly
                85                  90                  95

Met Thr Gly Tyr Glu Leu Leu Lys Lys Ile Lys Glu Ser Ser Ala Leu
            100                 105                 110

Arg Glu Ile Pro Val Val Ile Met Ser Ser Glu Asn Val Leu Ala Arg
        115                 120                 125

Ile Asp Arg Cys Met Glu Glu Gly Ala Glu Asp Phe Ile Val
    130                 135                 140

<210> SEQ ID NO 123
<211> LENGTH: 146
<212> TYPE: PRT
<213> ORGANISM: Eucalyptus grandis

<400> SEQUENCE: 123

Cys Ser Phe Thr Leu Ser Ser Ser Ser Pro Leu Phe Leu Ala Val Val
1               5                   10                  15

Leu Gly Arg Ser Pro Ile Glu Met Gly Val Thr Ala Ala Ser Gln Phe
            20                  25                  30

His Val Leu Ala Val Asp Asp Ser Leu Ile Asp Arg Lys Leu Ile Glu
        35                  40                  45

```
Arg Leu Leu Lys Thr Ser Ser Tyr Gln Val Thr Ala Val Asp Ser Gly
         50                  55                  60

Ser Lys Ala Leu Glu Phe Leu Gly Leu Asn Glu Gln Gln Pro Arg Asn
 65                  70                  75                  80

Ala Asn Ala Thr Ser Val Ser Pro Ser Tyr His His Gln Glu Ile Glu
                 85                  90                  95

Val Asn Leu Ile Ile Thr Asp Tyr Phe Met Pro Glu Met Thr Gly Tyr
            100                 105                 110

Asp Leu Leu Arg Lys Ile Lys Glu Ser Asn Ser Tyr Lys Asp Val Pro
            115                 120                 125

Val Val Ile Met Ser Ser Glu Asn Val Pro Ser Arg Ile Ser Gln Cys
            130                 135                 140

Leu Glu
145

<210> SEQ ID NO 124
<211> LENGTH: 426
<212> TYPE: PRT
<213> ORGANISM: Eucalyptus grandis

<400> SEQUENCE: 124

Gly Lys Leu Ala Val Tyr Val Ser Asp Arg Val Pro Glu Ala Val Ile
  1               5                  10                  15

Gly Asp Pro Gly Arg Phe Arg Gln Ile Ile Thr Asn Leu Val Gly Asn
             20                  25                  30

Ser Ile Lys Phe Thr His Glu Gly His Ile Phe Val Ser Val His Leu
         35                  40                  45

Leu Glu Glu Gly Cys Ser Gln His Asp Phe Arg Asp Val Glu Lys Arg
     50                  55                  60

Leu Ser Ser Asn Leu Val Glu Asp Thr Ser Asp Lys Thr Phe Asn Thr
 65                  70                  75                  80

Leu Ser Gly Phe Gln Val Val Asp Arg Arg Lys Ser Trp Glu Arg Phe
                 85                  90                  95

Lys Lys Leu Asn Arg Ser Asp Gln Ile Asp Val Asn Glu Ser Val Glu
            100                 105                 110

Val Leu Val Thr Val Glu Asp Thr Gly Val Gly Ile Ala Arg Glu Ala
            115                 120                 125

Gln Ser Arg Ile Phe Thr Pro Phe Val Gln Ala Asp Ser Ser Thr Ser
            130                 135                 140

Arg Thr Tyr Gly Gly Thr Gly Ile Gly Leu Ser Ile Ser Lys Cys Leu
145                 150                 155                 160

Val Asp Leu Met His Gly Glu Ile Gly Phe Val Ser Glu Pro Gly Thr
                165                 170                 175

Gly Ser Thr Phe Ser Phe Thr Val Pro Phe Ala Lys Cys Glu Met Asn
            180                 185                 190

Cys Leu Glu Val Lys Gly Gln Asn Tyr Asp Ser Ile Ile Ser Glu Phe
        195                 200                 205

Arg Gly Leu Arg Ala Leu Val Ile Asp Lys Arg His Ile Arg Ala Glu
    210                 215                 220

Val Ala Arg Tyr His Leu Glu Arg Leu Arg Ile Ser Val Asp Val Ala
225                 230                 235                 240

Cys Ser Leu Lys Ser Ala Cys Thr Tyr Leu Ser Asn Ser Ser Ser Pro
                245                 250                 255

Arg Glu Leu Ser Asp Phe Asp Met Val Leu Ile Asp Lys Asp Val Trp
            260                 265                 270
```

-continued

```
Asp Arg Gln Thr Gly Leu Glu Leu Asn Ile Ser Leu Trp Lys His Arg
            275                 280                 285
Gln Asn Gly Ser Asn Gly Val Ser Ile Arg Pro Lys Ile Phe Leu Leu
        290                 295                 300
Ala Thr Ser Ile Ser Pro Ile Glu His Ser Glu Leu Lys Leu Ala Asn
305                 310                 315                 320
Leu Val Asp Asn Val Leu Ala Lys Pro Leu Arg Leu Ser Val Leu Ile
                325                 330                 335
Ser Phe Leu Gln Glu Ala Leu Gly Asn Gly Lys Lys Arg Leu Ser Asp
            340                 345                 350
Arg Arg Lys Val Ser Thr Leu Gly Ser Leu Leu Lys Gly Arg Arg Ile
        355                 360                 365
Leu Val Val Asp Asp Asn Leu Val Asn Arg Arg Val Ala Glu Gly Ala
370                 375                 380
Leu Lys Lys Tyr Gly Ala Ile Val Thr Cys Val Gly Ser Gly Lys Asp
385                 390                 395                 400
Ala Val Ala Lys Leu Gln Pro Pro His Asp Phe Ala Ala Cys Phe Met
                405                 410                 415
Asp Leu Gln Met Pro Glu Met Asp Gly Phe
            420                 425

<210> SEQ ID NO 125
<211> LENGTH: 107
<212> TYPE: PRT
<213> ORGANISM: Eucalyptus grandis

<400> SEQUENCE: 125

Met Met Glu Ser Ser Lys Gly Phe Ser Ser Pro Arg Ser Asn Gly Phe
1               5                   10                  15
Pro Ala Gly Leu Arg Val Leu Val Val Asp Asp Asp Pro Thr Trp Leu
            20                  25                  30
Lys Ile Leu Glu Lys Met Leu Lys Lys Cys Ser Tyr Glu Val Thr Thr
        35                  40                  45
Cys Gly Leu Ala Arg Asp Ala Leu Lys Leu Leu Arg Glu Arg Lys Gly
    50                  55                  60
Gly Tyr Asp Ile Val Ile Ser Asp Val Asn Met Pro Asp Met Asp Gly
65                  70                  75                  80
Phe Lys Leu Leu Glu Leu Val Gly Leu Glu Met Asp Leu Pro Val Ile
                85                  90                  95
Met Met Ser Val Asp Gly Glu Thr Ser Arg Val
            100                 105

<210> SEQ ID NO 126
<211> LENGTH: 121
<212> TYPE: PRT
<213> ORGANISM: Pinus radiata

<400> SEQUENCE: 126

Met Val Thr Ser Arg Met Ser Ser Ala Met Arg Met Lys Lys Glu Lys
1               5                   10                  15
Asn Ala Ala Cys Gly Glu His Gly Asp Glu Leu Val Arg Cys Asp Glu
            20                  25                  30
Met His Val Leu Ala Val Asp Asp Cys Leu Ile Glu Arg Lys Val Ile
        35                  40                  45
Glu Lys Leu Leu Lys Thr Asn Phe Phe Lys Val Thr Ser Val Asp Ser
    50                  55                  60
```

```
Ala Glu Arg Ala Leu Glu Val Leu Gly Phe His Glu Glu Gln Ser Thr
 65                  70                  75                  80

Cys Ala Thr Thr Asn Ala Phe Lys Val Asn Met Ile Ile Thr Asp Tyr
                 85                  90                  95

Cys Met Pro Gly Met Thr Gly Tyr Asp Leu Leu Lys Lys Val Lys Glu
            100                 105                 110

Thr Lys Cys Leu Lys Glu Ile Pro Gly
        115                 120
```

<210> SEQ ID NO 127
<211> LENGTH: 261
<212> TYPE: PRT
<213> ORGANISM: Pinus radiata

<400> SEQUENCE: 127

```
Met Ala Val Ser Gln His Leu Phe Leu Ser Ala Gln Arg Leu Asn Gly
 1               5                  10                  15

Arg Glu Asp Glu Gly Ser Leu Tyr Leu Leu Arg Ala Gly Val Asn Trp
             20                  25                  30

Asp Leu Leu Ile Met Gly Val Ala Leu Val Ala Cys Leu Ala Ile Leu
         35                  40                  45

Gly Met Val Trp Lys Arg Arg Thr Trp Ser Tyr Cys Glu Gly Leu
 50                  55                  60

Gln Glu Glu Asp Ala Gly Gln Arg Ala Gln Glu Thr Gln Cys Ser Lys
 65                  70                  75                  80

Gly Phe Met Thr Asn Val Phe His Asn Thr Arg Asp Cys Arg Ser Glu
                 85                  90                  95

Gln Ile Ile Trp Asp Asp Ile His Ile Ser Ser Gln Thr Glu Thr Arg
            100                 105                 110

Ser Gln Lys Val Arg Thr Val Lys Ser Lys Ser Ser Met Ile Ser Arg
            115                 120                 125

Asp Ser Cys Ser Ser Pro Arg Arg Ile Leu Leu Val Glu Asp Thr Gln
130                 135                 140

Ile Asn Arg Ile Ile Phe Gly Arg Val Leu Gln Ser Leu Asn Leu Tyr
145                 150                 155                 160

Cys Glu Glu Ala Glu Asn Gly Lys Val Ala Val Asp Tyr Phe Lys Gln
                165                 170                 175

Gly Arg Thr Tyr Asp Leu Val Leu Met Asp Lys Glu Met Pro Val Met
            180                 185                 190

Asp Gly His Glu Ala Thr Arg Gln Leu Arg Ser Met Gly Val Lys Thr
            195                 200                 205

Pro Ile Val Ala Leu Thr Ala Asn Thr Leu Gln Ser Asp Lys Asp Leu
210                 215                 220

Phe Phe Glu Ala Gly Val Asp Asp Phe Gln Ser Lys Pro Leu Ser Arg
225                 230                 235                 240

Asp Arg Leu Val Gln Leu Leu Asp Gln Tyr Gly Val Asp Gly Cys Ala
                245                 250                 255

Gly Asn Arg Arg Gly
            260
```

<210> SEQ ID NO 128
<211> LENGTH: 120
<212> TYPE: PRT
<213> ORGANISM: Pinus radiata

<400> SEQUENCE: 128

```
Gly Tyr Leu Gly Ser Thr Ser Ser Val Gln Pro Val Asn Phe Tyr Leu
 1               5                  10                  15

Phe Trp Phe Ile Glu Val Ala Val Pro Gln His Leu Val Leu Gly His
             20                  25                  30

Gln Tyr Leu Ser Gly Thr Glu Gly Gly Asp Gly Leu Tyr Phe Leu Arg
             35                  40                  45

Ala Gly Leu Asn Trp Val Leu Leu Ile Met Gly Val Ala Leu Val Ala
 50                  55                  60

Cys Leu Ala Ile Phe Gly Met Val Trp Lys Arg Arg Thr Trp Ser
 65              70                  75                  80

Tyr Cys Gly Ala Met Gln Lys Glu Asp Ala Ser Gln Arg Ala Gln Glu
                 85                  90                  95

Ala Gln Cys Ser Lys Gly Cys Met Thr Asn Val Leu Pro Asn Thr Arg
            100                 105                 110

Ala Cys Arg Gly Ala His Ile Ile
            115                 120
```

<210> SEQ ID NO 129
<211> LENGTH: 214
<212> TYPE: PRT
<213> ORGANISM: Pinus radiata

<400> SEQUENCE: 129

```
Lys Arg Phe Leu Glu Gly His Glu Leu Ser Tyr Leu Arg Ala Ile Gly
 1               5                  10                  15

Val Ile Ile Leu Ser Ala Val Leu Lys Arg Arg Met Ile Leu Ala Asp
             20                  25                  30

Lys Ala Lys Ser Leu Phe Ile Ser Asn Ile Ser His Glu Leu Arg Thr
             35                  40                  45

Pro Leu His Gly Ile Leu Ala Ala Ala Glu Leu Leu Gly Asp Ser Pro
 50                  55                  60

Leu Asn His Ser Gln Leu Ser Phe Leu Glu Thr Val Gln Ala Cys Gly
 65                  70                  75                  80

Thr Ser Leu Val Glu Thr Val Asn His Val Leu Asp Phe Thr Lys Leu
                 85                  90                  95

Ser Gly Asn Ser Lys Ala Gly Gly Val Glu Lys Val Ile Val Pro Thr
            100                 105                 110

Arg Val Asp Leu Met Gln Leu Ile Glu Glu Ala Val Asp Gly Cys Trp
            115                 120                 125

Ile Gly His Arg Ala Arg Thr Ala Ile Met Gly Asp Thr Gly Ile Gly
            130                 135                 140

Ser Val Tyr Ser Pro Pro Glu Asp Leu Ser Ser Pro Lys Gln Leu Val
145                 150                 155                 160

Glu Thr Val Val Asp Ile Gly Trp Arg Lys Lys Gly Trp Ser Leu Lys
                165                 170                 175

Cys Glu Lys Gly Gly Ile Arg Arg Val Leu Met Asn Val Phe Gly Asn
                180                 185                 190

Ser Leu Lys Phe Thr Thr Asn Gly Tyr Val His Val Ile Leu Arg Glu
            195                 200                 205

Leu Pro Arg Ser Gly Asp
    210
```

<210> SEQ ID NO 130
<211> LENGTH: 224
<212> TYPE: PRT

-continued

```
<213> ORGANISM: Eucalyptus grandis

<400> SEQUENCE: 130

Met Thr Met Ala Gly Glu Ile Leu Arg Arg Gln Ser Pro Ala Glu Val
 1               5                  10                  15

Asp Leu Cys Gly Gly Ser Gly Gln Glu Leu His Val Leu Ala Val Asp
            20                  25                  30

Asp Ser Leu Val Asp Arg Lys Val Ile Glu Lys Leu Leu Lys Arg Leu
        35                  40                  45

Ser Cys Lys Val Thr Ala Val Asp Ser Gly Leu Arg Ala Leu Gln Phe
    50                  55                  60

Leu Gly Leu Asp Gly Glu Lys Ser Ser Val Gly Leu Asp Asp Leu Lys
65                  70                  75                  80

Val Asn Leu Ile Met Thr Asp Tyr Ser Met Pro Gly Met Thr Gly Tyr
                85                  90                  95

Glu Leu Leu Lys Lys Ile Lys Glu Ser Ser Ala Phe Arg Glu Thr Pro
            100                 105                 110

Val Val Ile Met Ser Ser Glu Arg Ile Leu Ala Arg Ile Asn Arg Cys
        115                 120                 125

Leu Glu Glu Gly Ala Glu Glu Phe Leu Ala Lys Pro Val Gln Leu Ser
    130                 135                 140

Asp Val Gln Arg Leu Lys Asn Phe Val Met Gly Gly Gly Glu Val Cys
145                 150                 155                 160

Pro Asp Arg Arg Ile Asn Lys Arg Arg Leu Glu Glu Asn Asn Asp Asn
                165                 170                 175

Asp Asp Asn Glu Asn His Ala Pro Ser Pro Val Ser Pro Leu Cys Ser
            180                 185                 190

Arg Asp Trp Ala Val Cys Ser Ser Ser Ser Ser Asp Ser Ser Ser Pro
        195                 200                 205

Ser Ile Ala Val Ser Ser Ser Lys Arg Leu Lys Ile His His Gln Ala
    210                 215                 220
```